United States Patent
Chaves et al.

(10) Patent No.: US 10,053,452 B2
(45) Date of Patent: Aug. 21, 2018

(54) CRYSTALLINE FORMS OF N-(4-((3-(2-AMINO-4-PYRIMIDINYL)-2-PYRIDINYL) OXY)PHENYL)-4-(4-METHYL-2-THIENYL)-1-PHTHALAZINAMINE SALTS AND USES THEREOF

(71) Applicant: AMGEN INC., Thousand Oaks, CA (US)

(72) Inventors: Mary Chaves, Arlington, MA (US); Matthew Bio, Belmont, MA (US); Matthew Peterson, Hopkinton, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/101,373

(22) PCT Filed: Nov. 25, 2014

(86) PCT No.: PCT/US2014/067385
§ 371 (c)(1),
(2) Date: Jun. 2, 2016

(87) PCT Pub. No.: WO2015/084649
PCT Pub. Date: Jun. 11, 2015

(65) Prior Publication Data
US 2016/0304504 A1    Oct. 20, 2016

Related U.S. Application Data

(60) Provisional application No. 61/911,341, filed on Dec. 3, 2013.

(51) Int. Cl.
| | | |
|---|---|---|
| *C07D 409/14* | (2006.01) | |
| *A61K 31/506* | (2006.01) | |
| *C07C 309/04* | (2006.01) | |
| *C07C 309/30* | (2006.01) | |

(52) U.S. Cl.
CPC .......... *C07D 409/14* (2013.01); *C07C 309/04* (2013.01); *C07C 309/30* (2013.01); *C07B 2200/13* (2013.01)

(58) Field of Classification Search
None
See application file for complete search history.

(56) References Cited

U.S. PATENT DOCUMENTS

| | | | | |
|---|---|---|---|---|
| 3,609,152 | A | * | 9/1971 | Hess ................ C07D 491/04 540/600 |
| 4,337,341 | A | * | 6/1982 | Zimmerman .......... C07C 45/68 546/112 |
| 7,560,551 | B2 | | 7/2009 | Cee et al. |
| 8,022,221 | B2 | | 9/2011 | Cee et al. |
| 8,686,155 | B2 | | 4/2014 | Cee et al. |
| 8,921,367 | B2 | | 12/2014 | Friberg et al. |
| 2007/0185111 | A1 | | 8/2007 | Cee et al. |
| 2012/0028917 | A1 | | 2/2012 | Payton et al. |

FOREIGN PATENT DOCUMENTS

| | | |
|---|---|---|
| WO | 2011031842 A1 | 3/2011 |
| WO | 2013149026 A2 | 10/2013 |

OTHER PUBLICATIONS

Berge et al. J.of Pharmaceutical Sciences, vol. 66, p. 1-19 (1977).*
Coumar, Cheung, Chang & Hsieh, Advances in Aurora kinase inhibitor patents, Expert Opin. Ther. Patents (2009) 19(3) p. 321-356.
Friedberg et al., Phase II Study of Alisertib, a Selective Aurora A Kinase Inhibitor, in Relapsed and Refractory Aggressive B- and T-Cell Non-Hodgkin Lymphomas; J of Clin Onc; V32(1) 2014 p. 44-50.
Kalous et al., AMG 900, pan-Aurora kinase inhibitor, preferentially inhibits the proliferation of breast cancer cell lines with dysfunctional p. 53; Breast Cancer Res Treat (2013) 141:397-408.
Payton et al., "Preclinical Evaluation of AMG 900, a Novel Potent and Highly Selective Pan-Aurora Kinase Inhibitor with Activity in Taxane-Resistant Tumor Cell Lines", Cancer Research, vol. 70, No. 23, 2010, pp. 9846-9854.
Hilton et al., Aurora Kinase Inhibition As an Anticancer Strategy, Journal of Clinical Oncology, vol. 32, No. 1 (Jan. 1), 2014: pp. 57-59.
Huang, Liyue et al., "In vitro and in vivo pharmacokinetic characterizations of AMG 900, an orally bioavailable small molecule inhibitor of aurora kinases", Xenobiotica, vol. 41, No. 5, 2011, pp. 400-408.
ISR for WO2015084649 Search report 7 pages, dated Feb. 18, 2015.

* cited by examiner

*Primary Examiner* — Emily Bernhardt
(74) *Attorney, Agent, or Firm* — Richard V. Person

(57) ABSTRACT

The present invention relates to crystalline forms and co-crystal forms of pharmaceutically acceptable salts of the compound, N-(4-((3-(2-amino-4-pyrimidinyl)-2-pyridinyl) oxy)phenyl)-4-(4-methyl-2-thienyl)-1-phthalazinamine (AMG 900, and pharmaceutical compositions comprising said crystalline and co-crystal forms thereof. The invention further provides uses of the crystalline forms and compositions, to treat cancer, including various types of solid tumors and hematologic cancer including myeloma and leukemia.

13 Claims, 20 Drawing Sheets

Absolute Measure

% Change

Absolute Measure

% Change

Absolute Measure

% Change

Absolute Measure

% Change

Absolute Measure

% Change

CRYSTALLINE FORMS OF N-(4-((3-(2-AMINO-4-PYRIMIDINYL)-2-PYRIDINYL)OXY)PHENYL)-4-(4-METHYL-2-THIENYL)-1-PHTHALAZINAMINE SALTS AND USES THEREOF

RELATED APPLICATIONS

This application is a national stage application under 35 U.S.C. § 371 of International Application No. PCT/US2014/067385, having an international filing date of Nov. 25, 2014, which claims the benefit of, and priority to, U.S. Provisional Patent Application No. 61/911,341, filed on Dec. 3, 2013, which specification is hereby incorporated here in by reference in its entirety.

FIELD OF THE INVENTION

The present invention relates to solid state crystalline forms of salts of N-(4-((3-(2-amino-4-pyrimidinyl)-2-pyridinyl)oxy)phenyl)-4-(4-methyl-2-thienyl)-1-phthalazinamine, pharmaceutical compositions, methods of making and uses thereof.

BACKGROUND OF THE INVENTION

The compound, N-(4-((3-(2-amino-4-pyrimidinyl)-2-pyridinyl)oxy)phenyl)-4-(4-methyl-2-thienyl)-1-phthalazinamine, also chemically named as 4-((3-(2-amino-pyrimidin-4-yl)-pyridin-2-yl)oxy)phenyl-(4-(4-methyl-thiophen-2-yl)-phthalazin-1-yl)amine, and is referred to herein as "AMG 900" has a chemical structure of

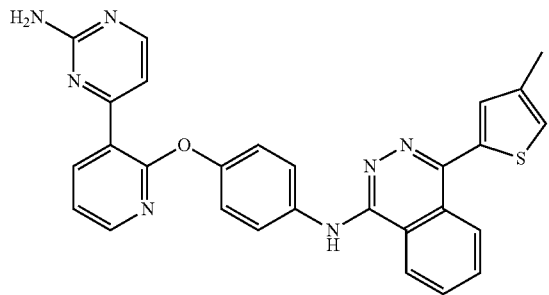

AMG 900 is an ATP competitive small molecule Aurora kinase inhibitor that is highly potent and selective for Aurora kinases A, B and C. AMG 900 is disclosed in US patent publication no. 20070185111, which published on Aug. 9, 2007 and issued as U.S. Pat. No. 7,560,551. AMG 900 is further disclosed in US patent publication no. 20090163501, now U.S. Pat. No. 8,022,221. Various uses and applications of AMG 900 are described in patent publications US20120028917 and WO2013149026. AMG 900 is being clinically evaluated primarily for its safety, tolerability and pharmacokinetic (PK) profile in human phase I trials for (1) advanced solid tumors (US Clinical Trial Id No. NCT00858377), and (2) for acute leukemias (US Clinical Trial Id No. NCT1380756).

Different solid state forms of a given compound are typically investigated to determine whether or not a particular form possesses and/or exhibits desirable properties allowing that compound to be clinically and/or commercially developed. Such beneficial and advantageous properties, by way of example, include without limitation, crystallinity, improved thermodynamic stability, non-hygroscopicity, high purity, minimal to total absence of moisture and/or residual solvents, chemical stability, high yielding synthetic process and/or manufacturability and reproducibility, desirable biopharmaceutical properties including improved dissolution characteristics and increased bioavailability, absence or reduced toxicities due to reduced or limited exposure, rate of exposure or release, or related to counter ions, good bulk and formulation properties including good flow, bulk density, desirable particle size and the like, or a combination of the aforementioned characteristic attributes.

Generally when a compound, also referred to herein as drug substance (DS), has been identified as a developmental candidate, the DS is screened to identify potentially beneficial polymorphic, crystalline or solid state forms of the compound and/or a pharmaceutically acceptable salt thereof. X-ray diffraction, Raman, solid state NMR and a melting point temperature and/or a melting point temperature range have been typically used to monitor or screen and identify the different polymorphic form of the DS. Different polymorphic forms of a given DS can have an impact on that compound's solubility, stability and bioavailability. Also, it is important to monitor possible changes in polymorphic forms of the DS during stability studies.

AMG 900 was previously isolated and identified as a free base compound. This compound exhibited rather lack-luster pharmacokinetic (PK) and/or pharmacodynamic (PD) properties, including poor aqueous solubility, poor bioavailability, poor absorption, poor target exposure and overall, a not-so-attractive in-vivo efficacy profile. Thus, there is a need to address and solve the technical problem of identifying alternative forms of AMG 900 to achieve substantially the same effect or an improved effect, including improved PK and PD profiles, as that of AMG 900 known in the art.

BRIEF DESCRIPTION OF THE DRAWINGS/FIGURES

BRIEF DESCRIPTION OF THE INVENTION

Figure 1:
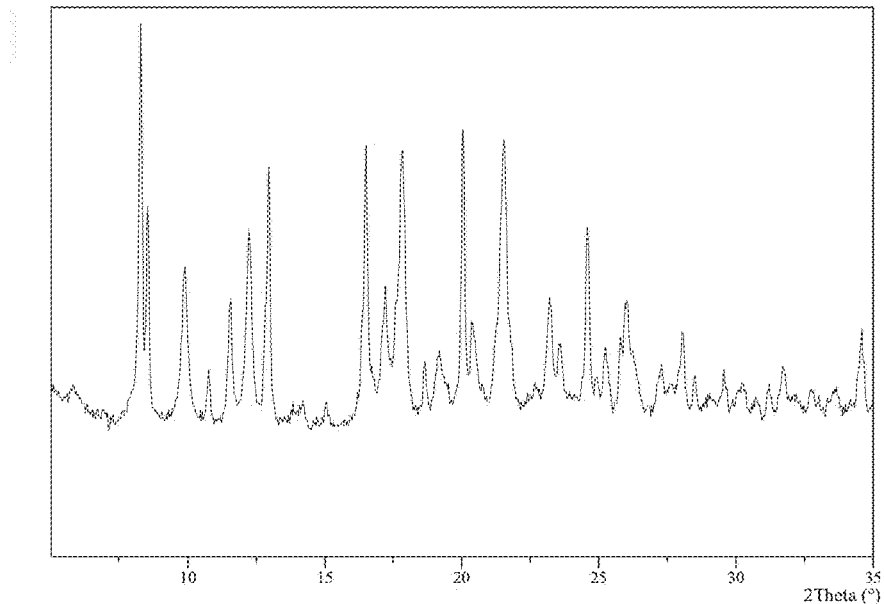
FIG. 1 is a graph depicting the X-ray powder diffraction (XRPD) pattern for the methanesulfonate salt (crystalline Form A) of AMG 900.

The present invention provides polymorphs or multiple crystalline forms of various salts of AMG 900, ie., solid state crystalline salt forms of N-(4-((3-(2-amino-4-pyrimidinyl)-2-pyridinyl)oxy)phenyl)-4-(4-methyl-2-thienyl)-1-phthalazinamine (AMG 900). Various of these crystalline salts possess unexpectedly beneficial properties, including improved solubility in water, improved (reduced) hygroscpicity properties, improved stability of DS, and improved in-vivo pharamcokinietic and pharmacodynamics properties. Such improved properties have enabled a pharmaceutically acceptable salt of AMG 900 to be tested in human clinical trials.

The invention further provides pharmaceutical compositions comprising the crystalline salt forms of AMG 900, methods for preparing them and uses thereof for the treatment of cancer, including treatment of solid tumors such as prostate, breast, ovarian tumors and the like, and myelogenous leukemias including myelodysplasia (MDS), chronic myelomonocytic leukemia (CMML), acute myeloid leukemia (AML), acute lymphocytic leukemia (ALL) and chronic myelogenous leukemia (CML).

The invention also provides uses of a pharmaceutical composition comprising one or more solid state crystalline forms of a pharmaceutically acceptable salt of AMG 900, for therapeutic, prophylactic, acute or chronic treatment of cancer and cancer cells in patients, including patients which have been previously treated with chemotherapeutic agents, including anti-mitotic agents. In one embodiment, the invention provides the use of AMG 900 in the manufacture of medicaments and pharmaceutical compositions for methods of treatment of cancer in subjects who have been previously treated with antimitotic agents, including mitotic spindle inhibitors and anti-microtubulin agents, or other drugs used in cancer chemotherapy (also referred to herein as chemotherapeutic agents), including doxorubicin, daunorubicin, dactinomycin, colchicine, vinblastine, vincristine, etoposide and mitoxantrone. In another embodiment, the invention provides a method of treating taxane-resistant tumor types, including non-small cell lung cancer, breast cancer, and hormone refractory prostate cancer in a subject, the method comprising administering to the subject an effective dosage amount of AMG 900 or a pharmaceutically acceptable salt thereof, to treat the taxane-resistant tumor.

DETAILED DESCRIPTION OF THE INVENTION

The present invention provides polymorphs or multiple crystalline forms of various salts, and co-crystals, of AMG 900, ie., solid state crystalline salt forms of AMG 900, and counter-ion co-crystals of AMG 900. The invention does not, however, provide or include crystalline forms of AMG 900 free base. The invention further provides pharmaceutical compositions comprising the crystalline salts, and co-cyrstal counter-ion, forms of AMG 900, methods for preparing them and uses thereof, as well as uses of these pharmaceutical compositions or medicaments to treat cancer, including, without limitation, specific types of cancer as described herein. Thus, the multiple embodiments provided hereinbelow are merely representative of the present invention. The invention should not be construed as being limited to the embodiments presented below.

In embodiment 1, the invention provides a crystalline form of a pharmaceutically acceptable salt of AMG 900 having the formula

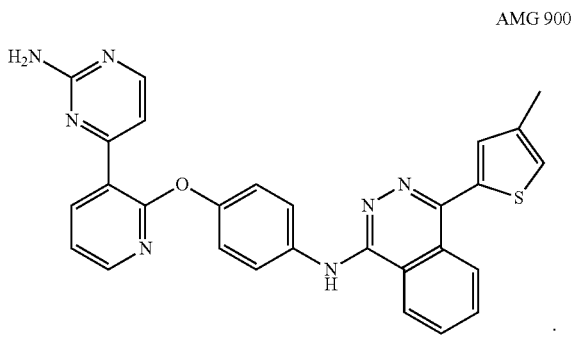 [SMILES: Cc1csc(-c2nnc(Nc3ccc(Oc4ncccc4-c4ccnc(N)n4)cc3)c3ccccc23)c1]

AMG 900

In embodiment 2, the invention provides the crystalline form of AMG 900 according to embodiment 1, wherein the pharmaceutically acceptable salt is selected from the group consisting of a mesylate salt, a bismesylate salt, a hydrochloride salt, a besylate salt, a tolsylate salt, an acetate salt, a sulfate salt and a fumarate salt.

In embodiment 3, the invention provides the crystalline form of AMG 900 according to any one of embodiments 1 and 2, wherein the pharmaceutically acceptable salt selected from a mesylate salt, a bismesylate salt, a besylate salt and a tosylate salt.

In embodiment 4, the invention provides the crystalline form of AMG 900 according to any one of embodiments 1-3, wherein the pharmaceutically acceptable salt selected from a mesylate salt or a bismesylate salt.

In embodiment 5, the invention provides the crystalline form of AMG 900 according to any one of embodiments 1-3, wherein AMG 900 is a pharmaceutically acceptable salt selected from a besylate salt and a tosylate salt.

In embodiment 6, the invention provides a crystalline form A of a mesylate salt of AMG 900 according to any one of embodiments 1-4 characterized by an X-ray powder diffraction (XRPD) diagram comprising peaks at the following angles of refraction 2 theta: 9.89+/−0.16°, 12.96+/−0.10°, 16.52+/−0.10°, 17.84+/−0.16°, 20.05+/−0.10° and 21.55+/−0.19°.

In embodiment 7, the invention provides a crystalline Form A of a mesylate salt of the AMG 900 according to any one of embodiments 1-4 and 6, characterized as providing an X-ray powder diffraction pattern substantially as shown in FIG. 1.

In embodiment 8, the invention provides a crystalline form of a bismesylate salt of AMG 900 according to any one of embodiments 1-4 characterized by an X-ray powder diffraction (XRPD) diagram comprising peaks at the following angles of refraction 2 theta: 10.7+/−0.2°, 12.7+/−0.2°, 15.17+/−0.20°, 20.7+/−0.2° and 24.8+/−0.2°.

In embodiment 9, the invention provides a crystalline form of a bismesylate salt of AMG 900 according to any one of embodiments 1-4, said form selected from Form A, Form B, Form C or Form D.

In embodiment 10, the invention provides a crystalline form A of a bismesylate salt of AMG 900 according to any one of embodiments 1-4 and 9 characterized by an X-ray powder diffraction (XRPD) diagram comprising peaks at the following angles of refraction 2 theta: 5.60+/−0.10°, 8.07+/−0.10°, 11.17+/−0.13°, 16.76+/−0.13° and 17.52+/−0.13°.

Figure 2:
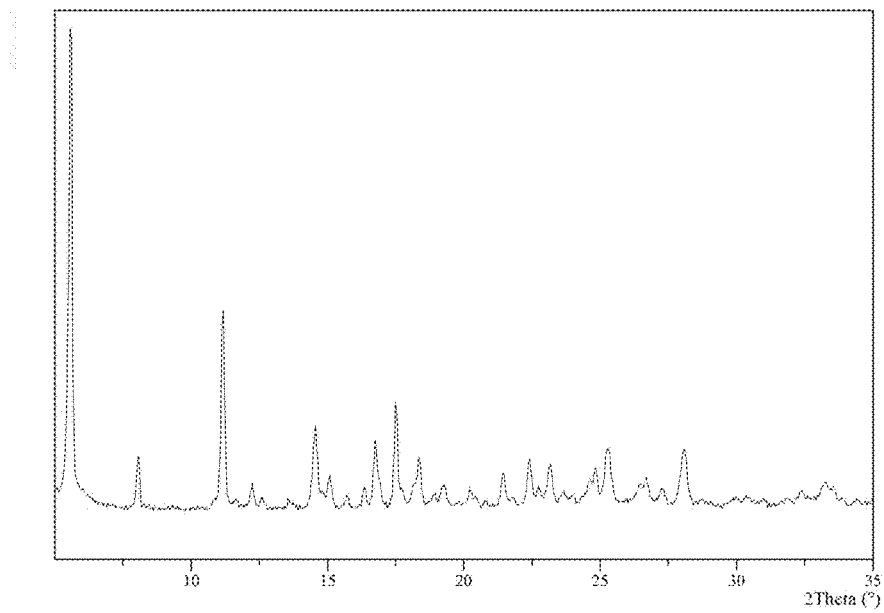
FIG. 2 is a graph depicting the X-ray powder diffraction (XRPD) pattern for the dimethanesulfonate salt (Form A) of AMG 900.

In embodiment 11, the invention provides a crystalline Form A of a bismesylate salt of the AMG 900 according to any one of embodiments 1-4, 9 and 10, characterized as providing an X-ray powder diffraction pattern substantially as shown in FIG. 2.

In embodiment 12, the invention provides a crystalline form B of a bismesylate salt of AMG 900 according to any one of embodiments 1-4 and 9 characterized by an X-ray powder diffraction (XRPD) diagram comprising peaks at the following angles of refraction 2 theta: 7.44+/−0.13°, 9.28+/−0.13°, 12.66+/−0.10°, 16.90+/−0.13° and 24.93+/−0.19°.

In embodiment 13, the invention provides a crystalline Form B of the bismesylate dihydrate salt of AMG 900 according to any one of embodiments 1-4, 9 and 12, characterized by an X-ray powder diffraction (XRPD) diagram comprising peaks at the following angles of refraction 2 theta: 7.44+/−0.13°, 9.28+/−0.13°, 12.66+/−0.10°, 16.90+/−0.13° and 24.93+/−0.19°, and wherein the strongest peak in the X-ray diffraction diagram is observed at an angle of refraction 2 theta of 24.93+/−0.19°.

Figure 3:
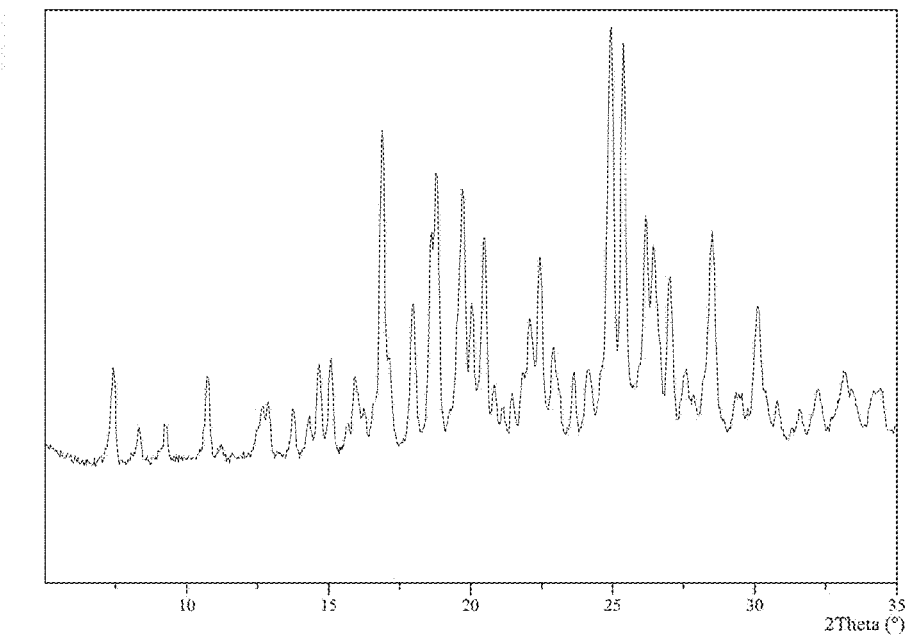
FIG. 3 is a graph depicting the X-ray powder diffraction (XRPD) pattern for the dimethanesulfonate salt (Form B) of AMG 900.

In embodiment 14, the invention provides a crystalline Form B of a bismesylate salt of the AMG 900 according to any one of embodiments 1-4, 8, 9, 12 and 13, characterized as providing an X-ray powder diffraction pattern substantially as shown in FIG. 3.

In embodiment 14a, the invention provides a crystalline Form B of a bismesylate dihydrate salt of the AMG 900 according to any one of embodiments 1-4, 8, 9 and 12-14, characterized as providing an X-ray powder diffraction pattern substantially as shown in FIG. 3.

In embodiment 15, the invention provides a crystalline form C of a bismesylate salt of AMG 900 according to any one of embodiments 1 to 4 and 9 characterized by an X-ray powder diffraction (XRPD) diagram comprising peaks at the following angles of refraction 2 theta: 8.29+/−0.10°, 8.55+/−0.10°, 12.96+/−0.10° and 16.51+/−0.23°.

Figure 5:
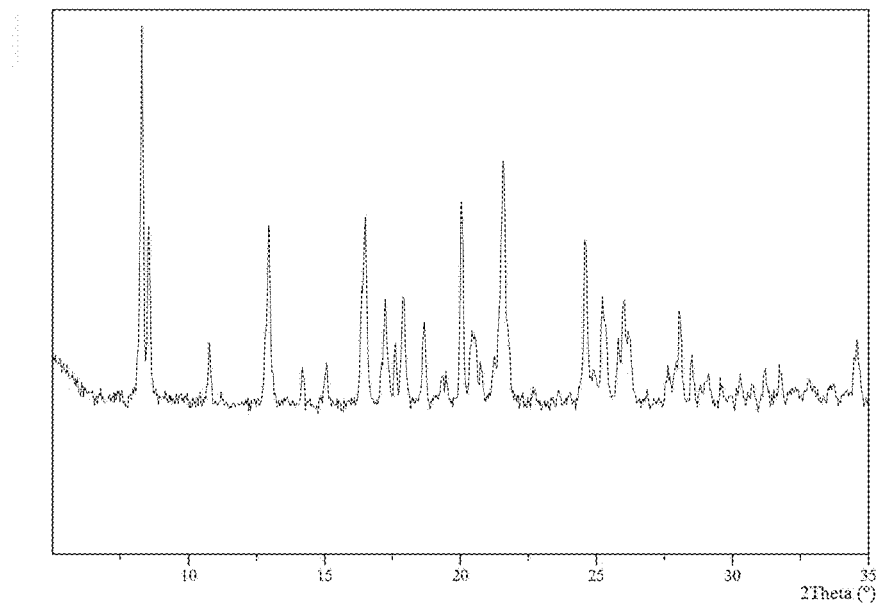
FIG. 5 is a graph depicting the dynamic vapor sorption (DVS) data for the dimethanesulfonate salt (crystalline Form C) of AMG 900.

In embodiment 16, the invention provides a crystalline Form C of a bismesylate salt of the AMG 900 according to any one of embodiments 1-4, 9 and 15, characterized as providing an X-ray powder diffraction pattern substantially as shown in FIG. 5.

In embodiment 17, the invention provides a crystalline form D of a bismesylate salt of AMG 900 according to any one of embodiments 1-4 and 9 characterized by an X-ray powder diffraction (XRPD) diagram comprising peaks at the following angles of refraction 2 theta: 6.88+/−0.16°, 8.89+/−0.13°, 9.59+/−0.13°, 13.46+/−0.13° and 13.80+/−0.13°.

Figure 7:
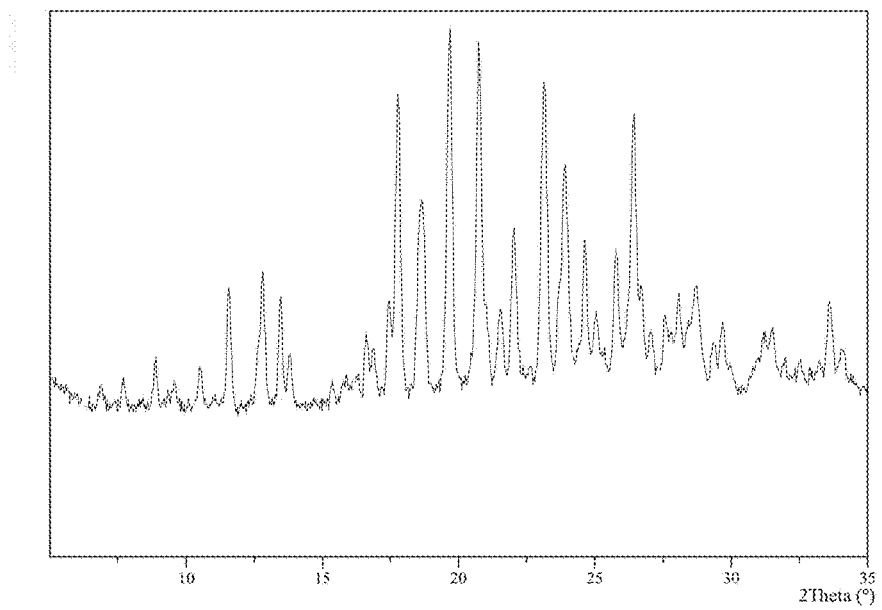
FIG. 7 is a graph depicting the X-ray powder diffraction (XRPD) pattern for the dimethanesulfonate salt (crystalline Form D) of AMG 900.

In embodiment 18, the invention provides a crystalline Form D of a bismesylate salt of the AMG 900 according to any one of embodiments 1-4, 9 and 17, characterized as providing an X-ray powder diffraction pattern substantially as shown in FIG. 7.

In embodiment 19, the invention provides a crystalline form E of a bismesylate salt of AMG 900 according to any one of embodiments 1-4 characterized by an X-ray powder diffraction (XRPD) diagram comprising peaks at the following angles of refraction 2 theta: 13.90+/−0.13°, 14.74+/−0.06°, 16.14+/−0.16° and 18.11+/−0.13°.

Figure 9:
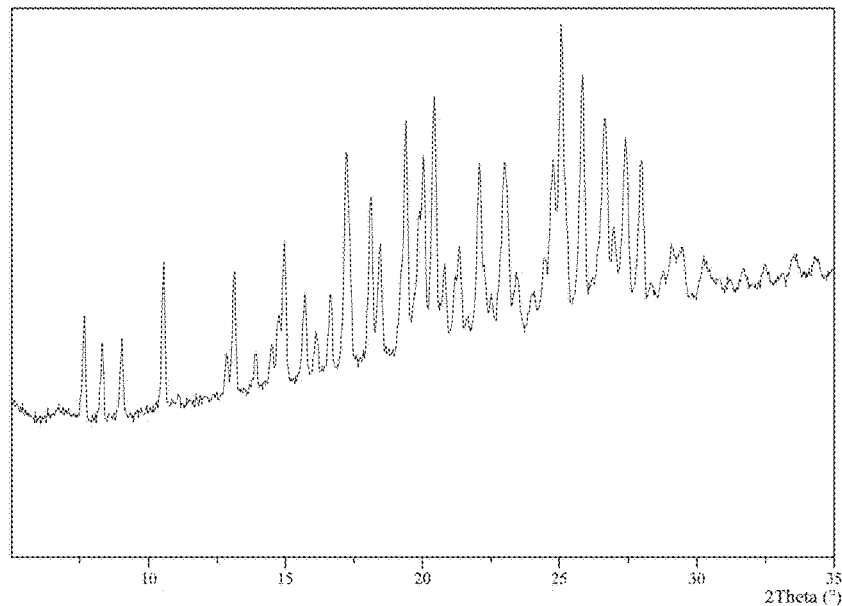
FIG. 9 is a graph depicting the X-ray powder diffraction (XRPD) pattern for the dimethanesulfonate salt (crystalline Form E) of AMG 900.

In embodiment 20, the invention provides a crystalline Form E of a bismesylate salt of the AMG 900 according to any one of embodiments 1-4 and 19, characterized as providing an X-ray powder diffraction pattern substantially as shown in FIG. 9.

In embodiment 21, the invention provides a crystalline form F of a bismesylate salt of AMG 900 according to any one of embodiments 1-4 characterized by an X-ray powder diffraction (XRPD) diagram comprising peaks at the following angles of refraction 2 theta: 10.23+/−0.10°, 13.32+/−0.10° and 15.40+/−0.10°.

Figure 10:
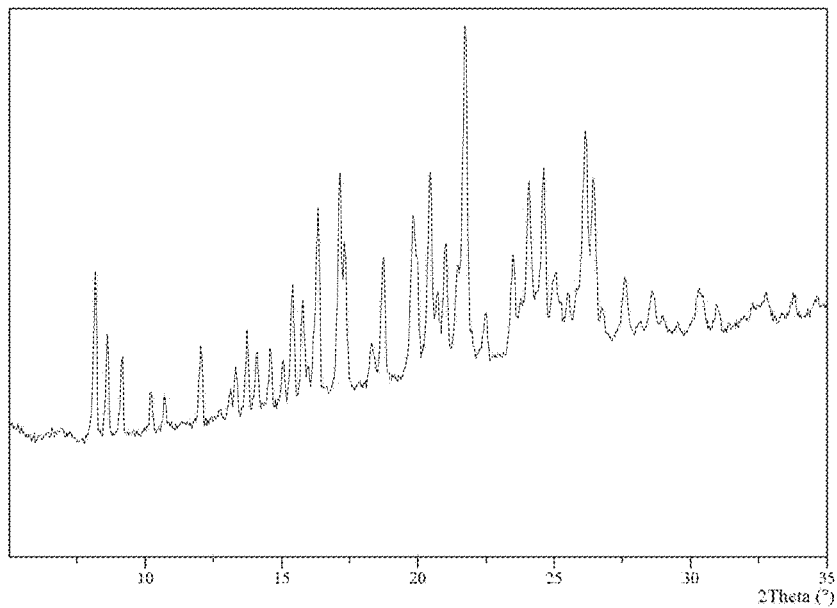
FIG. 10 is a graph depicting the X-ray powder diffraction (XRPD) pattern for the dimethanesulfonate salt (crystalline Form F) of AMG 900.

In embodiment 22, the invention provides a crystalline Form F of a bismesylate salt of the AMG 900 according to any one of embodiments 1-4 and 21, characterized as providing an X-ray powder diffraction pattern substantially as shown in FIG. 10.

In embodiment 23, the invention provides a crystalline form G of a bismesylate salt of AMG 900 according to any one of embodiments 1-4 characterized by an X-ray powder diffraction (XRPD) diagram comprising peaks at the following angles of refraction 2 theta: 18.99+/−0.10°, 19.47+/−0.10°, 23.97+/−0.10°, 25.16+/−0.10° and 25.34+/−0.10°.

Figure 11:
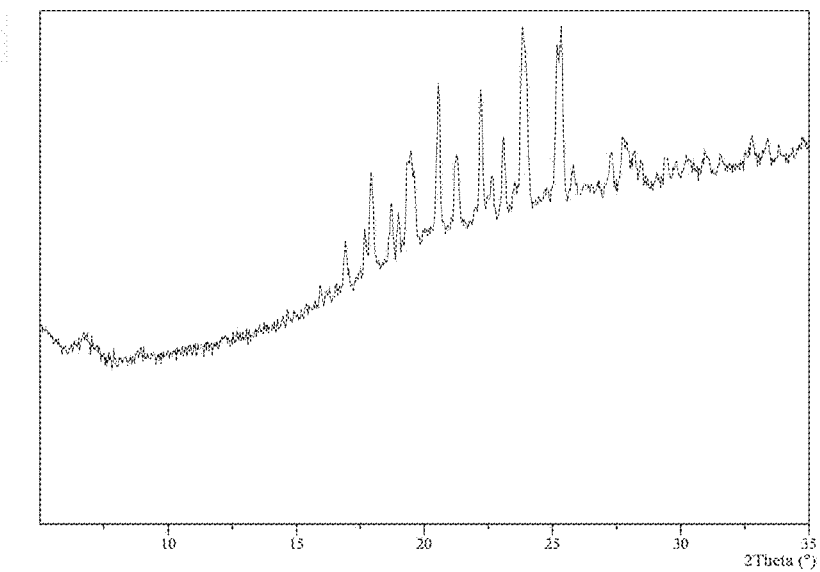
FIG. 11 is a graph depicting the X-ray powder diffraction (XRPD) pattern for the dimethanesulfonate salt (crystalline Form G) of AMG 900.

In embodiment 24, the invention provides a crystalline Form G of a bismesylate salt of the AMG 900 according to any one of embodiments 1-4 and 23, characterized as providing an X-ray powder diffraction pattern substantially as shown in FIG. 11.

In embodiment 25, the invention provides a crystalline Form A of a hydrochloride salt of AMG 900 according to any one of embodiments 1-2, characterized by an X-ray powder diffraction (XRPD) diagram comprising peaks at the following angles of refraction 2 theta: 6.72+/−0.10°, 9.16+/−0.10°, 13.03+/−0.13°, 13.34+/−0.06° and 15.76+/−0.10°.

In embodiment 26, the invention provides a crystalline Form A of a hydrochloride salt of the AMG 900 according to any one of embodiments 1-2 and 25, characterized as providing an X-ray powder diffraction pattern substantially as shown in FIG. 11.

In embodiment 27, the invention provides a crystalline Form B of a hydrochloride salt of AMG 900 according to any one of embodiments 1-2, characterized by an X-ray powder diffraction (XRPD) diagram comprising peaks at the following angles of refraction 2 theta: 8.74+/−0.13° and 22.06+/−0.19°.

Figure 12:
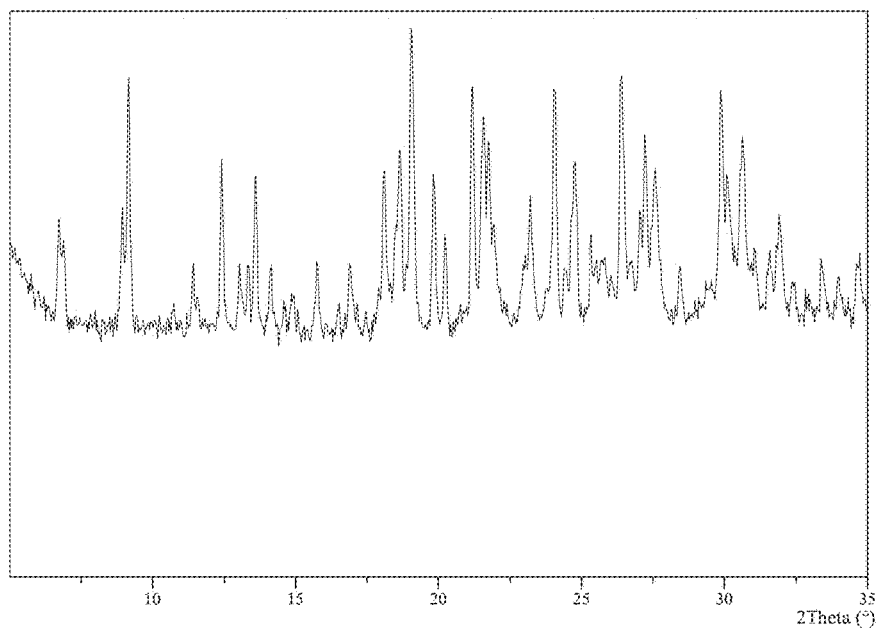
FIG. 12 is a graph depicting the X-ray powder diffraction (XRPD) pattern for the hydrochloride salt (crystalline Form A) of AMG 900.

In embodiment 28, the invention provides a crystalline Form B of a hydrochloride salt of AMG 900 according to any one of embodiments 1-2 and 27, characterized as providing an X-ray powder diffraction pattern substantially as shown in FIG. 12.

In embodiment 29, the invention provides a crystalline Form C of a hydrochloride salt of AMG 900 according to any one of embodiments 1-2 characterized by an X-ray powder diffraction (XRPD) diagram comprising peaks at the following angles of refraction 2 theta: 7.23+/−0.10°, 8.17+/−0.10°, 9.32+/−0.13°, 10.47+/−0.13° and 16.36+/−0.10°.

Figure 13:
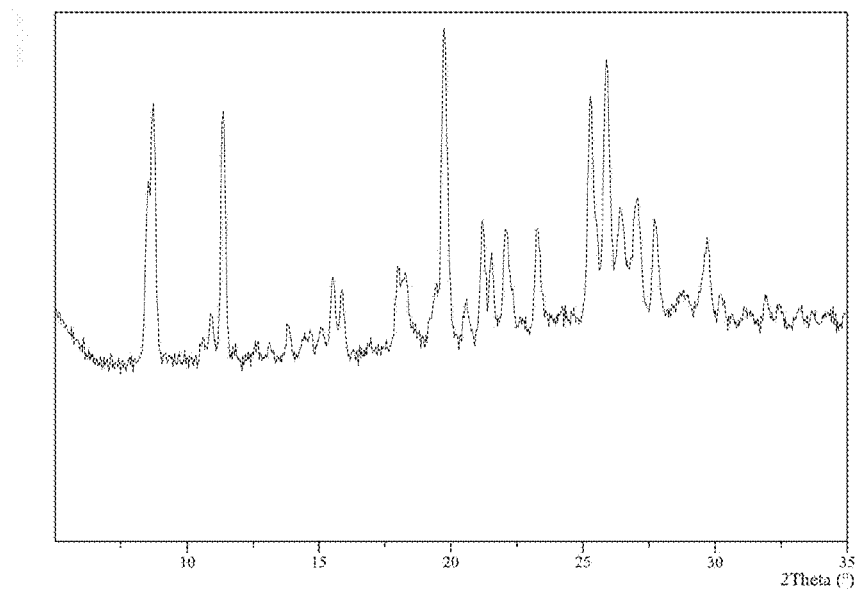
FIG. 13 is a graph depicting the X-ray powder diffraction (XRPD) pattern for the hydrochloride salt (crystalline Form B) of AMG 900.

In embodiment 30, the invention provides a crystalline Form C of a hydrochloride salt of the AMG 900 according to any one of embodiments 1-2 and 29, characterized as providing an X-ray powder diffraction pattern substantially as shown in FIG. 13.

In embodiment 31, the invention provides a crystalline Form D of a hydrochloride salt of AMG 900 according to any one of embodiments 1-2 characterized by an X-ray powder diffraction (XRPD) diagram comprising peaks at the following angles of refraction 2 theta: 9.56+/−0.13°, 10.26+/−0.13°, 12.72+/−0.16°, 17.61+/−0.10° and 22.45+/−0.16°.

Figure 14:
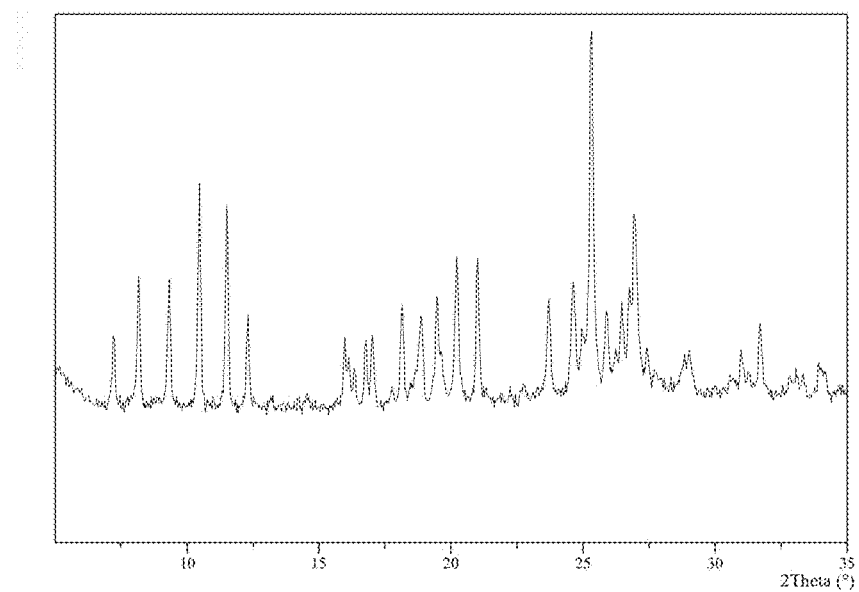
FIG. 14 is a graph depicting the X-ray powder diffraction (XRPD) pattern for the hydrochloride salt (crystalline Form C) of AMG 900.

In embodiment 32, the invention provides a crystalline Form D of a hydrochloride salt of the AMG 900 according to any one of embodiments 1-2 and 31, characterized as providing an X-ray powder diffraction pattern substantially as shown in FIG. 14.

In embodiment 33, the invention provides a crystalline Form E of a hydrochloride salt of AMG 900 according to any one of embodiments 1-2 characterized by an X-ray powder diffraction (XRPD) diagram comprising peaks at the following angles of refraction 2 theta: 8.35+/−0.16° and 20.70+/−0.13°.

Figure 15:
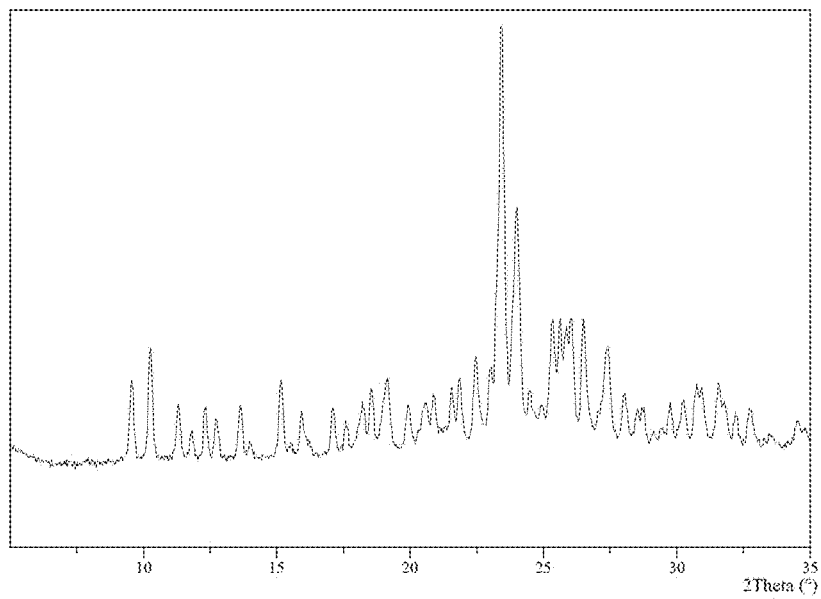
FIG. 15 is a graph depicting the X-ray powder diffraction (XRPD) pattern for the hydrochloride salt (crystalline Form D) of AMG 900.

In embodiment 34, the invention provides a crystalline Form E of a hydrochloride salt of the AMG 900 according to any one of embodiments 1-2 and 33, characterized as providing an X-ray powder diffraction pattern substantially as shown in FIG. 15.

In embodiment 35, the invention provides a crystalline form A of a besylate salt of AMG 900 according to any one of embodiments 1-3 and 5 characterized by an X-ray powder diffraction (XRPD) diagram comprising peaks at the following angles of refraction 2 theta: 7.16+/−0.13°, 9.87+/−0.19°, 12.23+/−0.16° and 13.20+/−0.23°.

Figure 17:
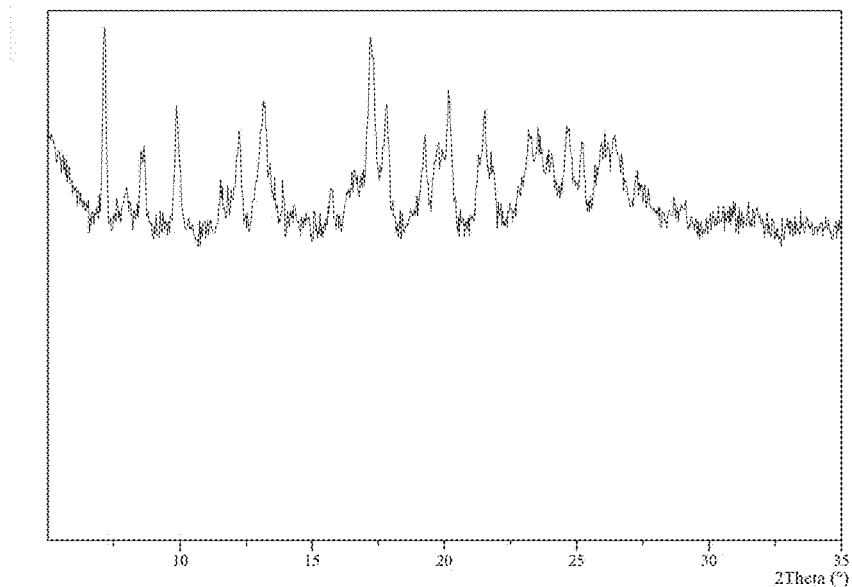
FIG. 17 is a graph depicting the X-ray powder diffraction (XRPD) pattern for the besylate (benzenesulfonate) salt (crystalline Form A) of AMG 900.

In embodiment 36, the invention provides a crystalline form A of a besylate salt of AMG 900 according to any one of embodiments 1-3, 5 and 35, characterized as providing an X-ray powder diffraction pattern substantially as shown in FIG. 17.

In embodiment 37, the invention provides a crystalline form A of a tosylate salt of AMG 900 according to any one of embodiments 1-3 and 5 characterized by an X-ray powder diffraction (XRPD) diagram comprising peaks at the following angles of refraction 2 theta: 6.26+/−0.16°, 10.10+/−0.13°, 11.35+/−0.13°, 12.49+/−0.16° and 13.51+/−0.16°.

Figure 18:
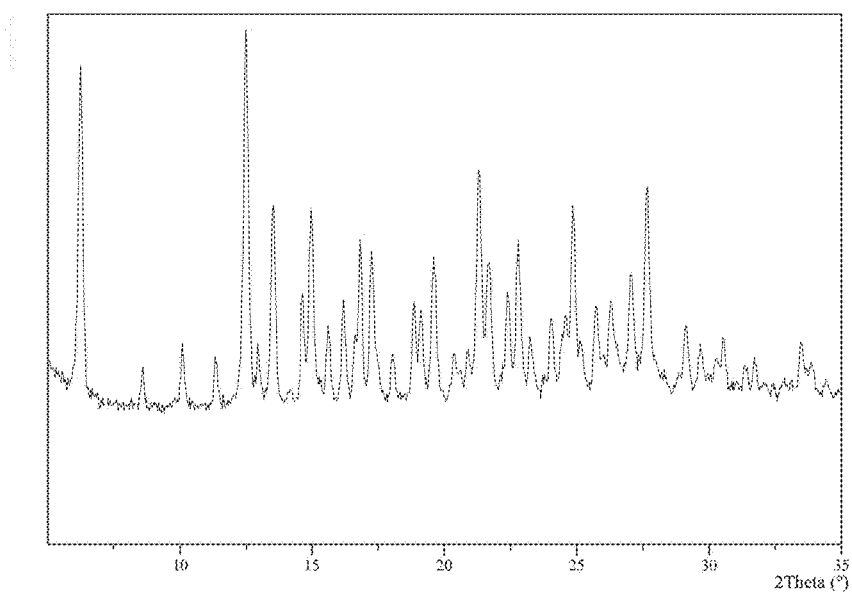
FIG. 18 is a graph depicting the X-ray powder diffraction (XRPD) pattern for the tosylate (tolueneulfonic acid) salt crystalline Form A of AMG 900.

In embodiment 38, the invention provides a crystalline form A of a tosylate salt of AMG 900 according to any one of embodiments 1-3, 5 and 37, characterized as providing an X-ray powder diffraction pattern substantially as shown in FIG. 18.

In embodiment 39, the invention provides a crystalline form A of an acetate salt of AMG 900 according to any one of embodiments 1-2 characterized by an X-ray powder diffraction (XRPD) diagram comprising peaks at the following angles of refraction 2 theta: 7.39+/−0.13°, 9.35+/−0.16°, 11.47+/−0.16° and 17.61+/−0.16°.

Figure 19:
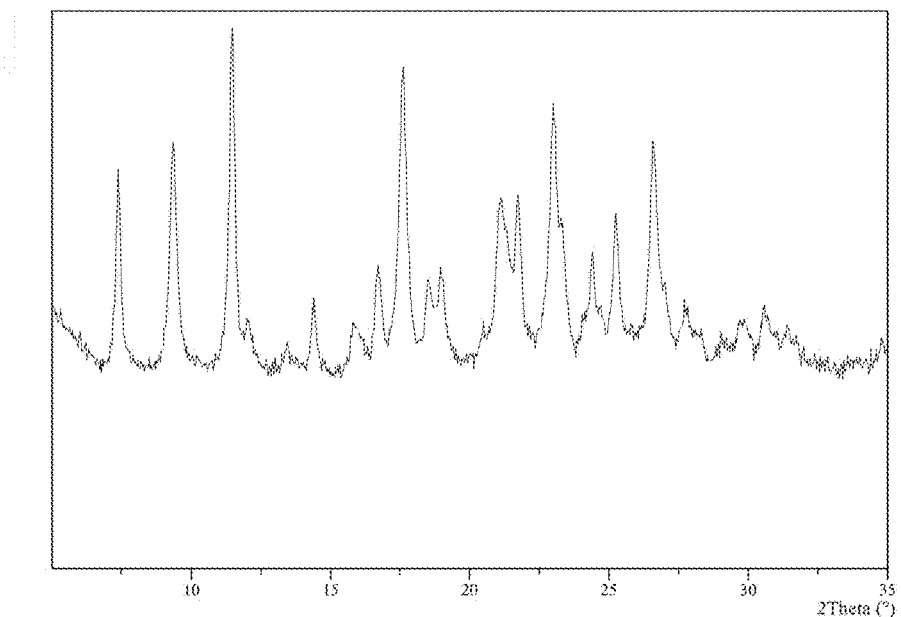
FIG. 19 is a graph depicting the X-ray powder diffraction (XRPD) pattern for the acetate salt crystalline Form A of AMG 900.

In embodiment 40, the invention provides a crystalline form A of an acetate salt of AMG 900 according to any one of embodiments 1-2 and 39, characterized as providing an X-ray powder diffraction pattern substantially as shown in FIG. 19.

In embodiment 41, the invention provides a crystalline Form A of a sulfate salt of AMG 900 according to any one of embodiments 1-2 characterized by an X-ray powder diffraction (XRPD) diagram comprising peaks at the following angles of refraction 2 theta: 22.84+/−0.16°, 24.97+/−0.19° and 28.96+/−0.16°.

Figure 20:
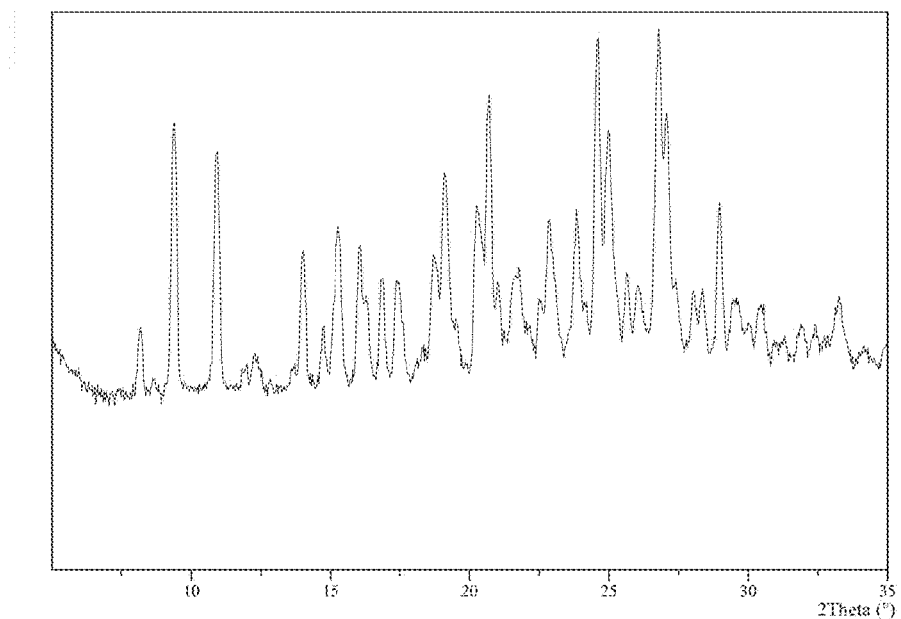
FIG. 20 is a graph depicting the X-ray powder diffraction (XRPD) pattern for the sulfate salt crystalline Form A of AMG 900.

In embodiment 42, the invention provides a crystalline Form A of a sulfate salt of the AMG 900 according to any one of embodiments 1-2, and 41, characterized as providing an X-ray powder diffraction pattern substantially as shown in FIG. 20.

In embodiment 43, the invention provides a crystalline Form B of a sulfate salt of AMG 900 according to any one of embodiments 1-2 characterized by an X-ray powder diffraction (XRPD) diagram comprising peaks at the following angles of refraction 2 theta: 11.32+/−0.13°, 17.26+/−0.16° and 23.41+/−0.13°.

Figure 21:
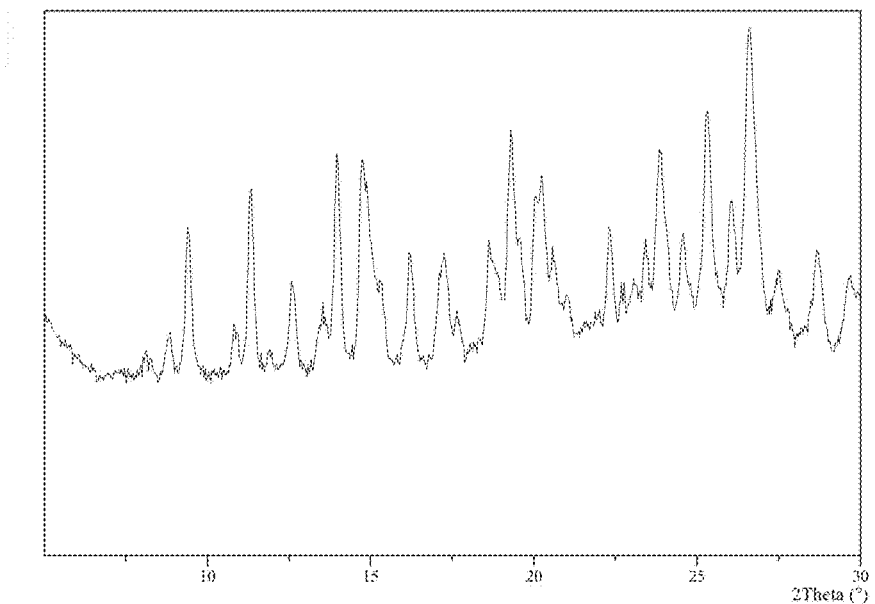
FIG. 21 is a graph depicting the X-ray powder diffraction (XRPD) pattern for the sulfate salt crystalline Form B of AMG 900.

In embodiment 44, the invention provides a crystalline Form B of a sulfate salt of the AMG 900 according to any one of embodiments 1-2 and 43, characterized as providing an X-ray powder diffraction pattern substantially as shown in FIG. 21.

In embodiment 45, the invention provides a crystalline Form C of a sulfate salt of AMG 900 according to any one of embodiments 1-2 characterized by an X-ray powder diffraction (XRPD) diagram comprising peaks at the following angles of refraction 2 theta: 6.53+/−0.19°, 7.43+/−0.10° and 13.03+/−0.19°.

Figure 22:
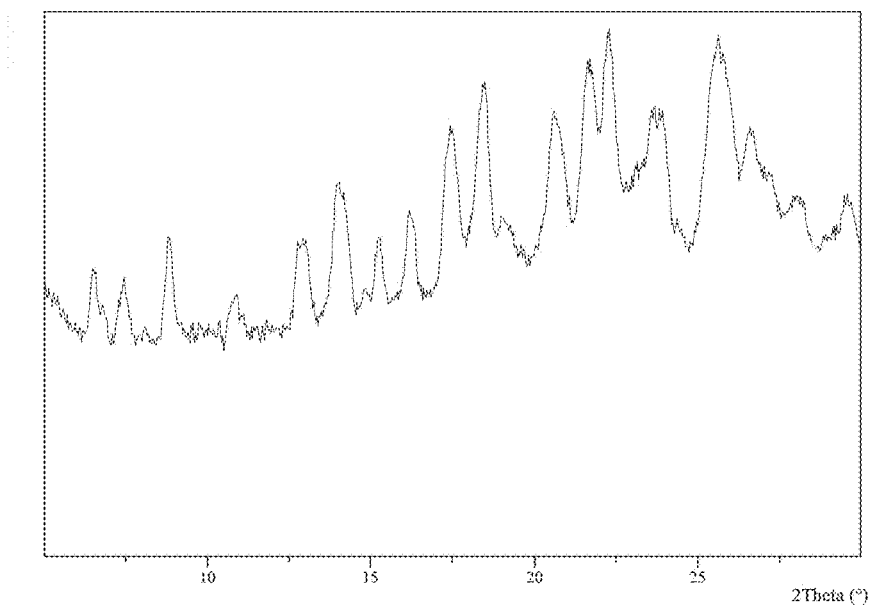
FIG. 22 is a graph depicting the X-ray powder diffraction (XRPD) pattern for the sulfate salt crystalline Form C of AMG 900.

In embodiment 46, the invention provides a crystalline Form C of a sulfate salt of the AMG 900 according to any one of embodiments 1-2 and 45, characterized as providing an X-ray powder diffraction pattern substantially as shown in FIG. 22.

In embodiment 47, the invention provides a crystalline Form D of a sulfate salt of AMG 900 according to any one of embodiments 1-2 characterized by an X-ray powder diffraction (XRPD) diagram comprising peaks at the following angles of refraction 2 theta: 8.31+/−0.13°, 11.97+/−0.16° and 21.94+/−0.23°.

Figure 23:
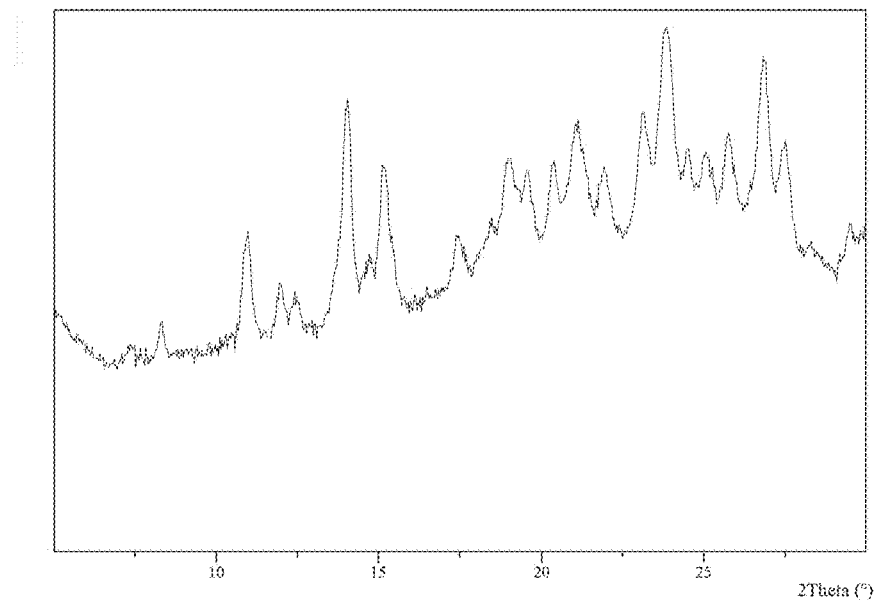
FIG. 23 is a graph depicting the X-ray powder diffraction (XRPD) pattern for the sulfate salt crystalline Form D of AMG 900.

In embodiment 48, the invention provides a crystalline Form D of a sulfate salt of the AMG 900 according to any one of embodiments 1-2 and 47, characterized as providing an X-ray powder diffraction pattern substantially as shown in FIG. 23.

In embodiment 49, the invention provides a crystalline Form E of a sulfate salt of AMG 900 according to any one of embodiments 1-2 characterized by an X-ray powder diffraction (XRPD) diagram comprising peaks at the following angles of refraction 2 theta: 9.89+/−0.13°, 11.15+/−0.19° and 19.94+/−0.16°.

Figure 24:
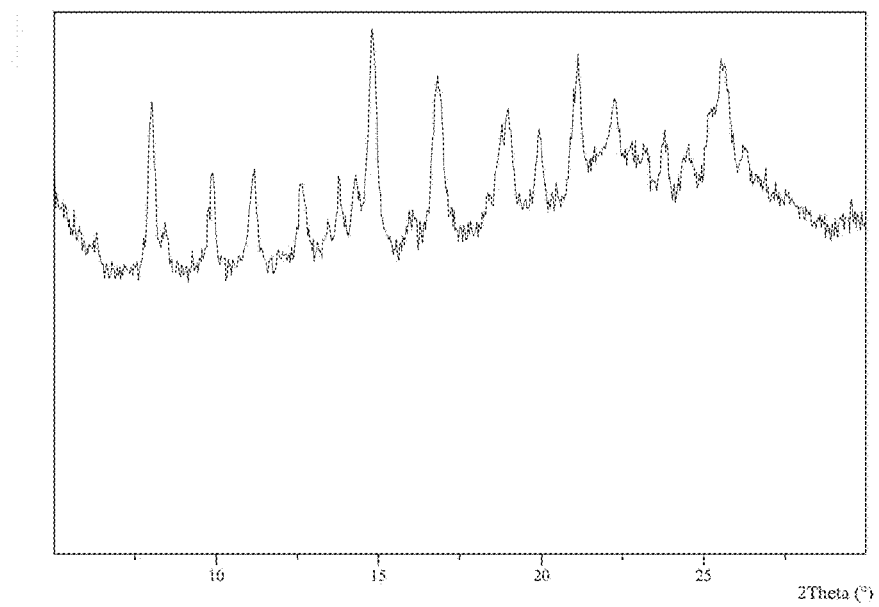
FIG. 24 is a graph depicting the X-ray powder diffraction (XRPD) pattern for the sulfate salt crystalline Form E of AMG 900.

In embodiment 50, the invention provides a crystalline Form E of a sulfate salt of the AMG 900 according to any one of embodiments 1-2 and 49, characterized as providing an X-ray powder diffraction pattern substantially as shown in FIG. 24.

In embodiment 51, the invention provides a crystalline Form A of a fumarate salt of AMG 900 according to any one of embodiments 1-2 characterized by an X-ray powder diffraction (XRPD) diagram comprising peaks at the following angles of refraction 2 theta: 6.95+/−0.16°, 8.70+/−0.23°, 12.87+/−0.19° and 14.47+/−0.10°.

Figure 25:
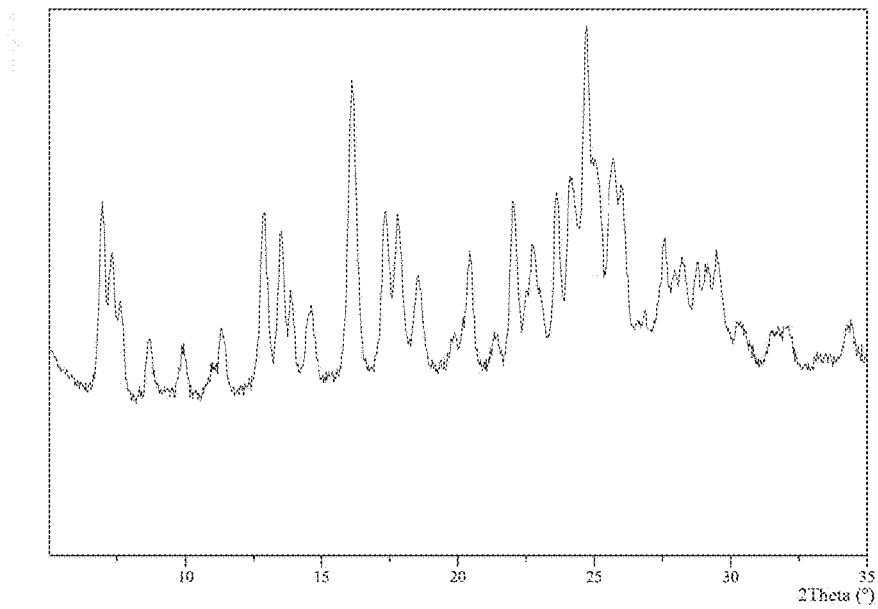
FIG. 25 is a graph depicting the X-ray powder diffraction (XRPD) pattern for the fumarate salt crystalline Form A of AMG 900.

In embodiment 52, the invention provides a crystalline Form A of a fumarate salt of the AMG 900 according to any one of embodiments 1-2 and 51, characterized as providing an X-ray powder diffraction pattern substantially as shown in FIG. 25.

In embodiment 53, the invention provides a co-crystal form A of mono-urea and AMG 900 according to any one of embodiments 1-2 characterized by an X-ray powder diffraction (XRPD) diagram comprising peaks at the following angles of refraction 2 theta: 5.34+/−0.16°, 10.66+/−0.19°, 11.33+/−0.16°, 12.06+/−0.16° and 16.14+/−0.13°.

Figure 27:
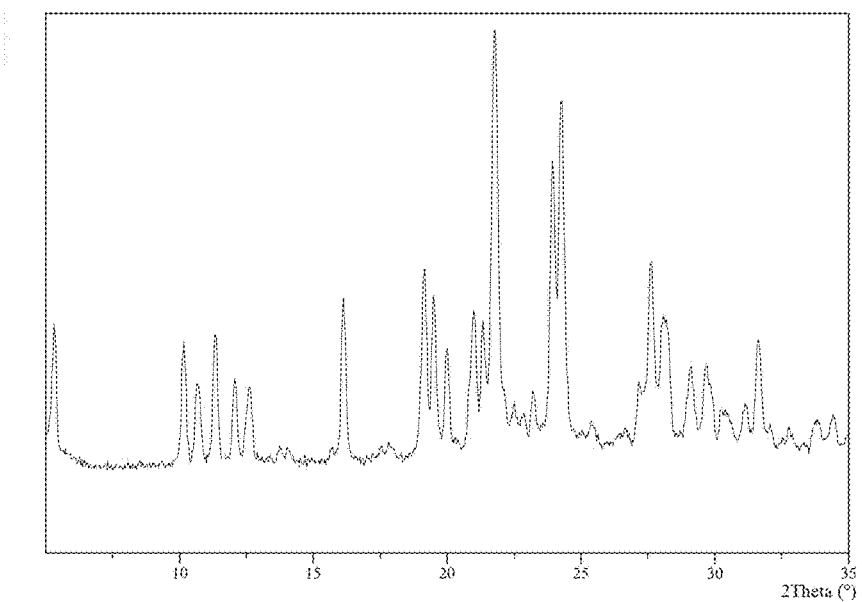
FIG. 27 is a graph depicting the X-ray powder diffraction (XRPD) pattern for the mono-urea salt crystalline Form A of AMG 900.

In embodiment 54, the invention provides a co-crystal form A of mono-urea and AMG 900 according to any one of embodiments 1-2 and 53, characterized as providing an X-ray powder diffraction pattern substantially as shown in FIG. 27.

In embodiment 55, the invention provides a co-crystal Form A of di-urea and AMG 900 according to any one of embodiments 1-2 characterized by an X-ray powder diffraction (XRPD) diagram comprising peaks at the following angles of refraction 2 theta: 6.32+/−0.13°, 8.23+/−0.13°, 15.42+/−0.13°, 18.95+/−0.16° and 20.31+/−0.19°.

Figure 28:
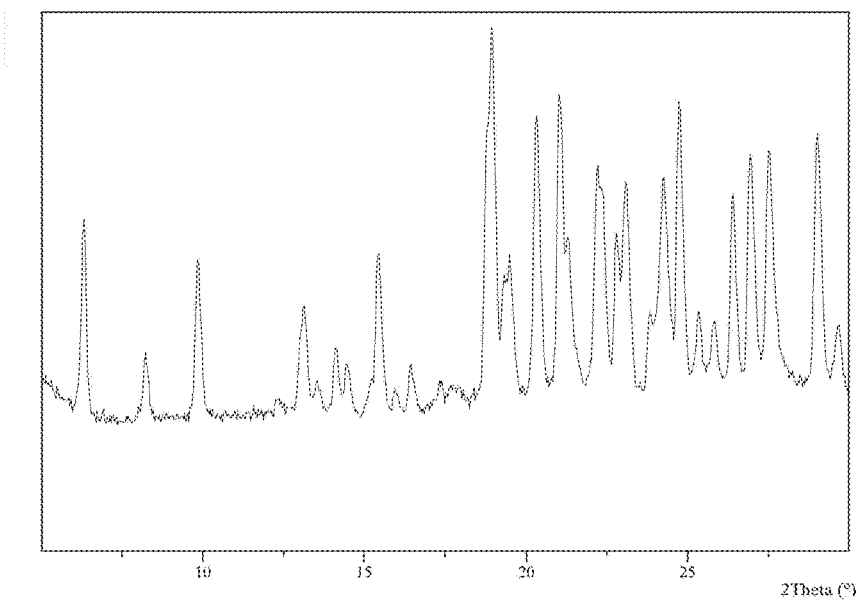
FIG. 28 is a graph depicting the X-ray powder diffraction (XRPD) pattern for the di-urea salt crystalline Form A of AMG 900.

In embodiment 56, the invention provides a co-crystal Form A of di-urea and AMG 900 according to any one of embodiments 1-2 and 55, characterized as providing an X-ray powder diffraction pattern substantially as shown in FIG. 28.

In embodiment 57, the invention provides a pharmaceutical composition (also referred to herein as a medicament) comprising a therapeutically effective dosage amount of a crystalline form of a pharmaceutically acceptable salt of AMG 900 according to any one of embodiments 1-55 and a pharmaceutically acceptable excipient, carrier or diluent.

In embodiment 58, the invention provides a pharmaceutical composition (also referred to herein as a medicament) comprising a therapeutically effective dosage amount of a crystalline form of AMG 900 according to any one of embodiments 9-24 and a pharmaceutically acceptable excipient, carrier or diluent.

In embodiment 59, the invention provides a pharmaceutical composition (also referred to herein as a medicament) comprising a therapeutically effective dosage amount of a crystalline form of AMG 900 according to any one of embodiments 11, 14, 14a, 16, 18, 20, 22 and 24 and a pharmaceutically acceptable excipient, carrier or diluent.

In embodiment 60, the invention provides a pharmaceutical composition (also referred to herein as a medicament) comprising a therapeutically effective dosage amount of a crystalline form of AMG 900 according to any one of embodiments 13, 14 and 14a and a pharmaceutically acceptable excipient, carrier or diluent.

DEFINITIONS

The following definitions should further assist in understanding the scope of the invention described herein.

The terms "cancer" and "cancerous" when used herein refer to or describe the physiological condition in subjects that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers, in a subject, which have become resistant in some degree to treatment with anti-cancer agents, including without limitation chemotherapeutic agents, antimitotic agents, anthracyclines and the like, and for cancers which have relapsed post treatment with such anti-cancer agents.

The term "chemotherapeutic agent" when used herein refers to the treatment of a cancer by killing cancerous cells. This term additionally refers to antineoplastic drugs used to treat cancer or a combination of these drugs into a standardized treatment regimen. Examples of chemotherapeutic agents include, without limitation, alkylating agents such as cisplatin, carboplatin, oxaliplatin; alkaloids including vinca alkaloids (examples include vincristine, vinblastine, vinorelbine and vindesine) and taxanes (examples include paclitaxel (Taxol®) and docetaxel); topoisomerase inhibitors such as irinotecan, topotecan, amsacrine, etoposide, etoposide phosphate and teniposide; and various antineoplastic agents such as dactinomycin, doxorubicin, epirubicin, bleomycin and others.

The term "comprising" is meant to be open ended, including the indicated component(s) but not excluding other elements. The term "comprising" as used herein is also meant to be synonymous with the terms "having" and "including."

The term "instructing" as used herein is intended to mean the directions provided on a pharmaceutical product label that has been approved by a regulatory authority. The term "instructing" also includes the language in an insert, otherwise indicated outside the scope of "indications" on an approved label, such as a US Food and Drug Administration (FDA) approved drug product label. Instructing as used herein, is also intended to include "directing." For instance, an accompanying pamphlet or brochure instruction how to take or administer the approved drug is also directing it's use.

The term "prescribing" as used herein is intended to mean the act of writing a prescription for a subject to administer or otherwise have administered the invention, ie. an amount of a crystalline form of a salt of AMG 900. The term "prescribing" may apply to licensed doctors and their authorized staff, including hospital physicians and related staff.

The term "refractory" when used here is intended to refer to not-yielding to, resistant or non-responsive to treatment, stimuli (therapy) or cure, including resistance to multiple therapeutic curative agents. "Refractory" when used herein in the context of characterizing a cancer or tumor is intended to refer to the cancer or tumor being non-responsive or having a resistant or diminished response to treatment with one or more anticancer agents. The treatment typically is continual, prolonged and/or repetitive over a period of time resulting in the cancer or tumor developing resistance or becoming refractory to that very same treatment.

The term "subject" as used herein refers to any mammal, including humans and animals, such as cows, horses, dogs and cats. Thus, the invention may be used in human patients as well as in veterinary subjects and patients. In one embodiment of the invention, the subject is a human.

The phrase "therapeutically-effective" is intended to quantify the amount of the compound (AMG 900), which will achieve a reduction in size or severity of the cancer or tumor over treatment of the cancer by conventional antimitotic cancer therapies, while reducing or avoiding adverse side effects typically associated with the conventional antimitotic cancer therapies. Therapeutically-effective amount is also intended to include amounts suitable and/or approved, by an authorized regulatory agency, for prophylactic use.

The terms "treat", "treating" and "treatment" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compound may be prepared from an inorganic acid or from an organic acid. Examples of such inorganic acids include, without limitation, hydrochloric, hydrobromic, hydroiodic, nitric, carbonic, sulfuric and phosphoric acid. Examples of organic acids include, without limitation, aliphatic, cycloaliphatic, aromatic, arylaliphatic, heterocyclic, carboxylic and sulfonic classes of organic acids, examples of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of the compound include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of the salts contemplated herein may be prepared by conventional means from the corresponding compound by reacting, for example, the appropriate acid or base with the compound.

Salt Terminology:

A "mesylate" salt is intended to refer to its commonly understood meaning, ie., a methansulfonate salt or a methane sulfonic acid salt. A mesylate salt includes, without limitation, a monomesylate salt (monomethanesulfonate salt, also simply referred to as methanesulfonate salt), a bismesylate salt (dimethanesulfonate salt), and the like.

A "bismesylate" salt is intended to refer to its commonly understood meaning, ie., a dimethansulfonate salt or a di-methanesulfonic acid salt.

A "besylate" salt is intended to refer to its commonly understood meaning, ie., a benzenesulfonate salt or a benzenesulfonic acid salt.

A "tosylate" salt is intended to refer to its commonly understood meaning, ie., a toluenesulfonate salt or a toluenesulfonic acid salt.

A "fumarate" salt is intended to refer to its commonly understood meaning, ie., a fumaric acid salt.

A "maleate" salt is intended to refer to its commonly understood meaning, ie., a maleic acid salt.

AMG 900, N-(4-((3-(2-amino-4-pyrimidinyl)-2-pyridinyl)oxy)phenyl)-4-(4-methyl-2-thienyl)-1-phthalazinamine, also chemically described as 4-((3-(2-amino-pyrimidin-4-yl)-pyridin-2-yl)oxy)phenyl-(4-(4-methyl-thiophen-2-yl)-phthalazin-1-yl)amine, may be prepared by the procedure analogous to that described in PCT publication WO2007087276, Example Methods A1 or A2 on pg 70 but using 1-chloro-4-(4-methyl-2-thienyl)phthalazine as the starting material, in conjunction with Examples 15 (pg 50), 25 (pg 55) and 30 (pg 59). These procedures are also described in U.S. Pat. No. 7,560,551, which specification is hereby incorporated herein by reference in its entirety. Specifically, AMG 900 may be prepared as described in Example 1 below.

Example 1

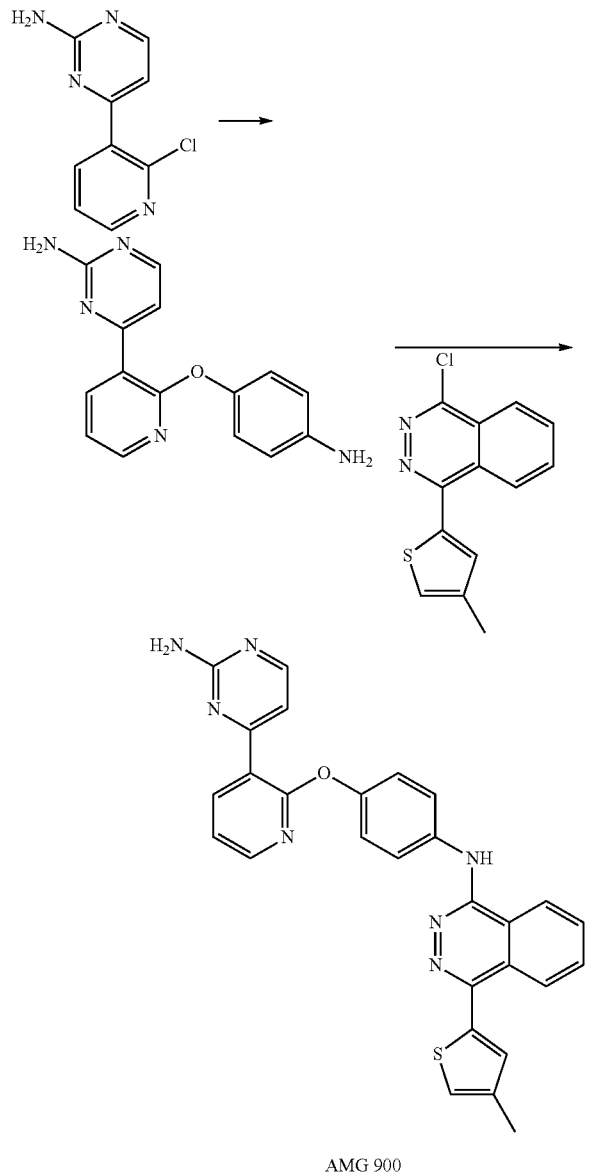

AMG 900

Synthesis of N-(4-((3-(2-amino-4-pyrimidinyl)-2-pyridinyl)oxy)phenyl)-4-(4-methyl-2-thienyl)-1-phthalazinamine (AMG 900)

Step 1: 4-(2-chloropyridin-3-yl)pyrimidin-2-amine

In an argon purged 500 mL round bottom flask placed in an isopropanol bath, was added sodium metal (3.40 g, 148 mmol) slowly to methanol (180 mL). The mixture was stirred at room temperature (RT) for about 30 minutes. To this was added guanidine hydrochloride (12.0 mL, 182 mmol) and the mixture was stirred at RT for 30 minutes, followed by addition of (E)-1-(2-chloropyridin-3-yl)-3-(dimethylamino)prop-2-en-1-one (12.0 g, 57.0 mmol), attached air condenser, moved reaction to an oil bath, where it was heated to about 50° C. for 24 hr. Approximately half of the methanol was evaporated under reduced pressure and the solids were filtered under vacuum, then washed with saturated sodium bicarbonate (NaHCO$_3$) and H$_2$O, air dried to yield 4-(2-chloropyridin-3-yl)pyrimidin-2-amine as off white solid. MS m/z=207 [M+1]$^+$. Calc'd for C$_9$H$_7$ClN$_4$: 206.63.

Step 2: 4-(2-(4-aminophenoxy)pyridin-3-yl)pyrimidin-2-amine

To a resealable tube was added 4-aminophenol (1.3 g, 12 mmol), cesium carbonate (7.8 g, 24 mmol), and DMSO (16 ml, 0.75 M). The mixture was heated to 100° C. for 5 minutes, and then 4-(2-chloropyridin-3-yl)pyrimidin-2-amine (2.5 g, 12 mmol) was added, and the reaction mixture was heated to 130° C. overnight. Upon completion, as judged by LCMS, the reaction mixture was allowed to cool to RT and diluted with water. The resulting precipitate was filtered, and the solid washed with water and diethyl ether. The solid was then taken up in 9:1 CH$_2$Cl$_2$:MeOH and passed through a pad of silica gel with 9:1 CH$_2$Cl$_2$:MeOH as eluent. The solvent was concentrated in vacuo to provide the desired product, 4-(2-(4-aminophenoxy)pyridin-3-yl)pyrimidin-2-amine MS m/z=280 [M+1]$^+$. Calc'd for C$_{15}$H$_{13}$N$_5$O: 279.30.

Step 3: 1-Chloro-4-(4-methylthiophen-2-yl)phthalazine 1,4-Dichlorophthalazine (1.40 g, 7.03 mmol), 4-methylthiophen-2-ylboronic acid (999 mg, 7.03 mmol), and PdCl$_2$ (DPPF) (721 mg, 985 μmol) were added into a sealed tube. The tube was purged with Argon. Then sodium carbonate (2.0 M in water) (7.74 ml, 15.5 mmol) and 1,4-dioxane (35.2 ml, 7.03 mmol) were added. The tube was sealed, stirred at RT for 5 min, and placed in a preheated oil bath at 110° C. After 1 hr, LC-MS showed product and byproduct (double coupling), and starting material dichlorophthalazine. The reaction was cooled to RT, filtered through a pad of celite with an aid of ethyl acetate (EtOAc), concentrated, and loaded onto column. The product was purified by column chromatography using Hex to remove the top spot, then 80:20 hexanes:EtOAc to collect the product. The product, 1-chloro-4-(4-methylthiophen-2-yl)phthalazine was obtained as yellow solid. LC-MS showed that the product was contaminated with a small amount of dichlorophthalazine and biscoupling byproduct. MS m/z=261 [M+1]$^+$. Calcd for C$_{13}$H$_9$ClN$_2$S: 260.12.

Step 4: N-(4-((3-(2-amino-4-pyrimidinyl)-2-pyridinyl)oxy)phenyl)-4-(4-methyl-2-thienyl)-1-phthalazinamine To 4-(2-(4-aminophenoxy)pyridin-3-yl)pyrimidin-2-amine and 1-chloro-4-(4-methyl-2-thienyl)phthalazine was added tBuOH. The resulting mixture was heated at 100° C. in a sealed tube for 16 hours. The reaction was diluted with diethyl ether and saturated sodium carbonate and vigorously shaken. The resulting solids were filtered and washed with water, diethyl ether and air dried to yield N-(4-((3-(2-amino-4-pyrimidinyl)-2-pyridinyl)oxy)phenyl)-4-(4-methyl-2-thienyl)-1-phthalazinamine as an off-white solid. MS m/z=504 [M+H]$^+$. Calc'd for C$_{28}$H$_{21}$N$_7$OS: 503.58.

Example 2

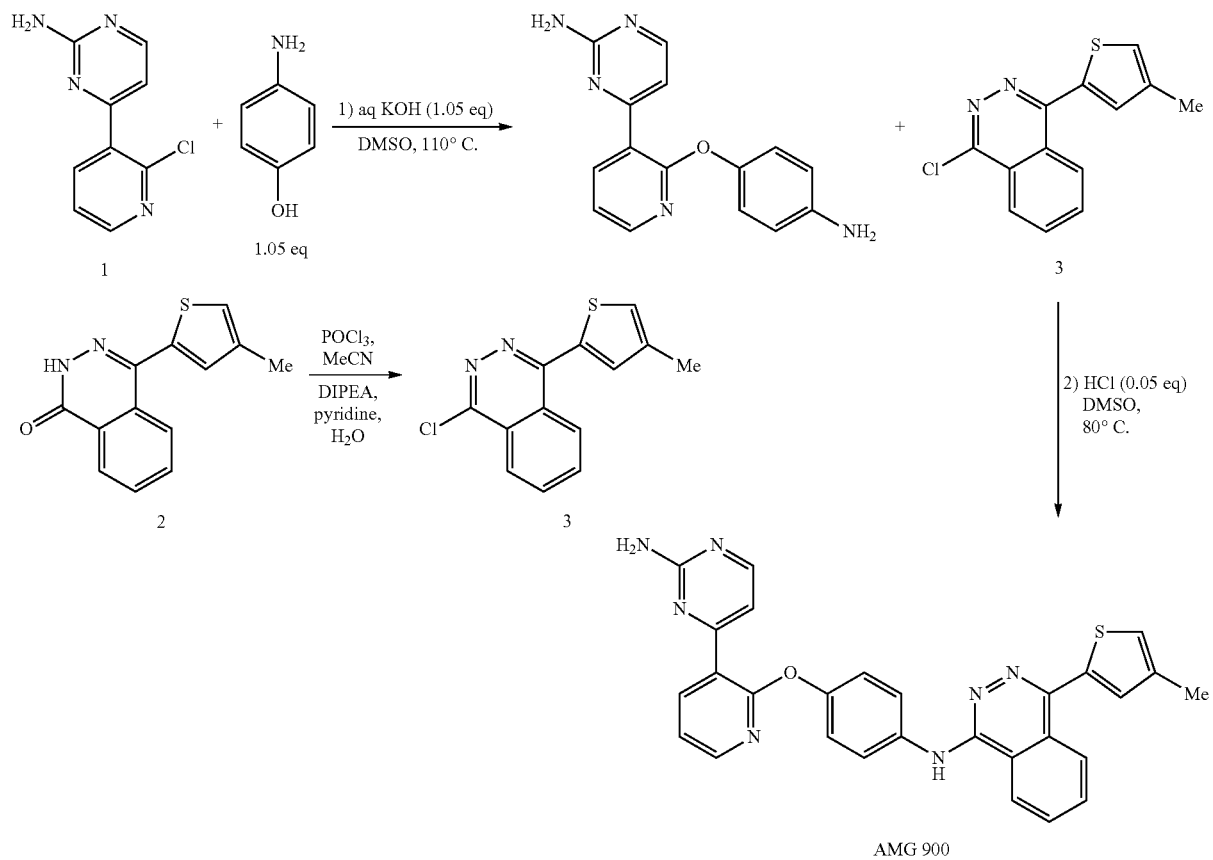

Alternative Synthesis of N-(4-((3-(2-amino-4-pyrimidinyl)-2-pyridinyl)oxy)phenyl)-4-(4-methyl-2-thienyl)-1-phthalazinamine (AMG 900)

Step 1: 4-(2-chloropyridin-3-yl)pyrimidin-2-amine

In an argon purged 500 mL round bottom flask placed in an isopropanol bath, was added sodium metal (3.40 g, 148 mmol) slowly to methanol (180 mL). The mixture was stirred at room temperature (RT) for about 30 minutes. To this was added guanidine hydrochloride (12.0 mL, 182 mmol) and the mixture was stirred at RT for 30 minutes, followed by addition of (E)-1-(2-chloropyridin-3-yl)-3-(dimethylamino)prop-2-en-1-one (12.0 g, 57.0 mmol), attached air condenser, moved reaction to an oil bath, where it was heated to about 50° C. for 24 hr. Approximately half of the methanol was evaporated under reduced pressure and the solids were filtered under vacuum, then washed with saturated sodium bicarbonate (NaHCO$_3$) and H$_2$O, air dried to yield 4-(2-chloropyridin-3-yl)pyrimidin-2-amine as off white solid. MS m/z=207 [M+1]$^+$. Calc'd for C$_9$H$_7$ClN$_4$: 206.63.

Step 2: 4-(2-(4-aminophenoxy)pyridin-3-yl)pyrimidin-2-amine

To a reaction vessel at ambient temperature was added 4-aminophenol (571 g, 5.25 mol, 1.05 equiv) followed by 4-(2-chloropyridin-3-yl)pyrimidin-2-amine (1064 g, 97 wt %, 5.00 mol, 1.0 equiv) and DMSO (7110 ml, 7820 g, 7× the volume of 4-(2-chloropyridin-3-yl)pyrimidin-2-amine). The reaction mixture was agitated and sparged with nitrogen gas for at least 10 minutes. Then a 50 weight % aqueous KOH solution (593 g, 5.25 mol, 1.05 equiv.) was added to the mixture while keeping the reaction mixture temperature below about 40° C. The mixture was sparged with nitrogen gas for more than 5 minutes, the sparging tube was removed, and the reaction mixture was heated to 110+/−10° C. for at least 1.5 hrs. Upon completion, as judged by HPLC, the reaction mixture was allowed to cool to RT and diluted with 6N HCl (42 mL, 0.25 mol, 0.05 equiv). The desired product, 4-(2-(4-aminophenoxy)pyridin-3-yl)pyrimidin-2-amine was not isolated. Rather, it was formed in-situ and combined with the product of step 3 below, in step 4 to form the desired product.

Step 3: 1-Chloro-4-(4-methylthiophen-2-yl)phthalazine

A separate reaction vessel was fitted with a reflux condenser and an addition funnel, and 4-(4-methylthiophen-2-yl)phthalazin-1(2H)-one (1,537 mg, 6.34 mol, 1.0 equivalent) was added to the reaction vessel. Acetonitrile (7540 mL, 5859 g, 5 V), was added and the reaction vessel was agitated to allow the starting material to dissolve. The vessel was then charged with phosphorus oxychloride (709 ml, 1166 g, 7.44 mol, 1.2 equivalents) and the reaction was heated to about 75+/−5° C. for a least 4 hrs. The reaction was cooled to about 25+/−5° C. and held there for more than 24 hrs. N,N-diisopropylethylamine (3046 g, 4100 mL, 3.8 equivalents) was added to the reaction vessel and the temperature was maintained at <30° C. Pyridine (97 g, 1.24 mol, 0.2 equiv) was added in a single portion followed by water (4100 g, 2.7V) over more than 30 minutes. The reaction mixture was stirred at ambient temperature of about 24 hrs. the mixture was filtered through a <25 uM polypropylene filter and the resulting mother liquor was diluted with 1:1 ACN:water (9000 mL total) and stirred for a minimum of 2 minutes. Filter off product solids as they precipitate. Collect mother liquor and washes to obtain additional product. Dry the filter cake, and additional product crops, under a constant stream of nitrogen gas for at least 14 hrs. Unlike the previous method, the present method avoids contamination of impurities, such as dichlorophthalazine and biscoupling byproduct, as seen via LC-MS. Yield: 1537 g (97.2 weight %). MS m/z=261 [M+1]+. Calcd for $C_{13}H_9ClN_2S$: 260.12.

Step 4: N-(4-((3-(2-amino-4-pyrimidinyl)-2-pyridinyl)oxy)phenyl)-4-(4-methyl-2-thienyl)-1-phthalazinamine To the reaction mixture was added 1-chloro-4-(4-methylthiophen-2-yl)phthalazine (1450 g, 97.2 wt %, 5.40 mol, 1.08 equiv) finding the addition port with DMSO (520 ml, 572 g, 0.5× the volume of 4-(2-chloropyridin-3-yl)pyrimidin-2-amine). The reaction mixture was again agitated and sparged with nitrogen gas for at least 10 minutes. The sparging tube was removed, and the reaction mixture was heated to 80+/−20° C. for at least 2 hrs. Upon completion, as judged by HPLC, the reaction mixture was allowed to cool to RT and N,N-diisopropylethylamine (776 g, 1045 mL, 6.0 mol, 1.2 equiv) was added and the mixture was kept at about 80+/−10° C. Filter the mixture at about 80° C. into a separate reactor vessel rinsing with DMSO (1030 mL, 1133 g, 1 V). Then adjust the reaction mixture temperature to about 70+/−5° C. and add 2-propanol (13200 mL, 10360 g, 12.75 V) over more than 15 minutes at about 70° C. As the reaction mistreu cools, the product begins to precipitate out of solution. Add more 2-propanol (8780 mL, 6900 g, 8.5V) to the solution slowly over more then 60 minutes at about 70° C. The reactor vessel was cooled to about 20° C. over more than 60 minutes and let sit for over 2 hrs. The product was filtered through an Aurora filter with a >25 uM polypropylene filter cloth. Additional crops were obtained from the mother liquors by diluting with additional 2-propanol. The filter cakes were dried under a constant stream of nitrogen gas for at least 14 hrs to provide the desired product, N-(4-((3-(2-amino-4-pyrimidinyl)-2-pyridinyl)oxy)phenyl)-4-(4-methyl-2-thienyl)-1-phthalazinamine as an off-white solid. Yield: 2831 g (88.8%); purity 99.7%. MS m/z=504 [M+H]+. Calc'd for $C_{28}H_{21}N_7OS$: 503.58.

The starting material 1 used/shown in Example 2 was prepared as follows:

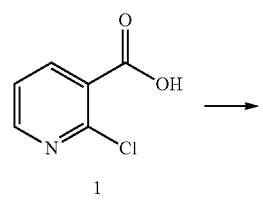

1

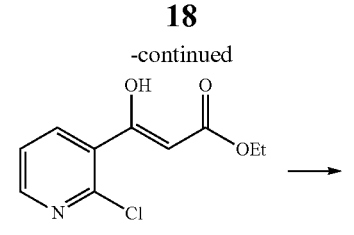

2

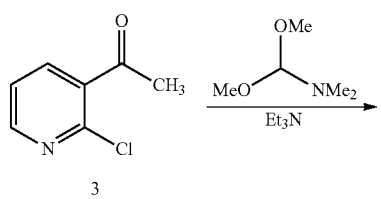

3

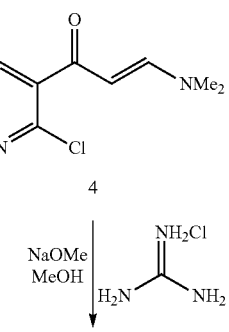

4

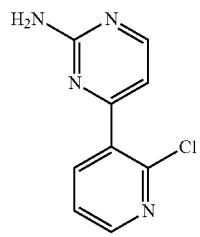

and starting material 3, thienyl substituted phthalazinone, shown in Example 2 was prepared as follows:

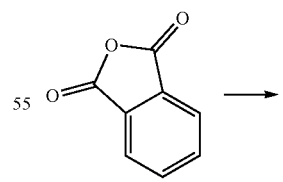

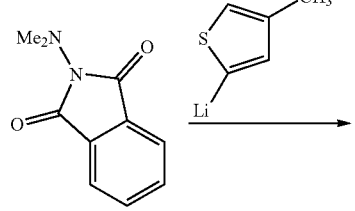

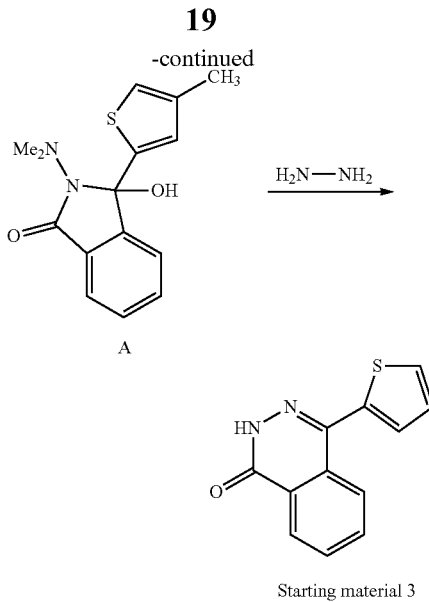

A

Synthesis of 4-(5-methylthiophen-2-yl)phthalazin-1(2H)-one

Step 1: 2-(Dimethylamino)isoindoline-1,3-dione

A solution of isobenzofuran-1,3-dione (5.00 g, 34 mmol) and N,N-dimethylhydrazine (2.9 ml, 37 mmol) in toluene (75 ml, 34 mmol) was added p-TsOH·H$_2$O (0.32 g, 1.7 mmol). The Dean-Stark apparatus and a condenser were attached. The mixture was refluxed. After 4 hr, LCMS showed mainly product. The reaction was cooled to rt. Toluene was removed under reduced pressure the crude was dissolved in DCM, washed with sat NaHCO$_3$, water, and brine. The organic was dried over MgSO$_4$, filtered, and concentrated. Light yellow solid was obtained. $^1$H NMR showed mainly product, 2-(dimethylamino)isoindoline-1,3-dione. MS Calcd for C$_{10}$H$_{10}$N$_2$O$_2$: [M]$^+$=190. Found: [M+H]$^+$=191.

Step 2: 2-(Dimethylamino)-3-hydroxy-3-(5-methyl-thiophen-2-yl)isoindolin-1-one A solution of 2-bromo-5-methylthiophene (0.60 mL, 5.3 mmol) in THF (11 mL) was purged with nitrogen and cooled to −78° C. n-Butyllithium (2.2 mL, 5.5 mmol; 2.5 M in THF) was added and the mixture was stirred under nitrogen for 30 min. This solution was cannulated into a flask containing a solution of 2-(dimethylamino)isoindoline-1,3-dione (1.5 g, 7.9 mmol) in THF (16 mL) at −78° C. under nitrogen. The reaction was allowed to warm to −30° C. over an hour, at which point LCMS showed complete conversion of 2-bromo-5-methylthiophene to product. The reaction was quenched by careful addition of saturated aqueous NH$_4$Cl. The reaction mixture was diluted with dichloromethane and water, and the layers were separated. The aqueous portion was extracted with additional dichloromethane, and the combined organic layers were dried with MgSO$_4$, filtered, concentrated, and purified by silica gel chromatography eluting with 0-2% MeOH in dichloromethane to provide intermediate A, as a light yellow solid, 2-(dimethylamino)-3-hydroxy-3-(5-methylthiophen-2-yl)isoindolin-1-one (1.2 g, 80% yield). $^1$H NMR (400 MHz, DMSO-d$_6$) δ 7.68-7.65 (m, 1H), 7.63-7.59 (m, 1H), 7.57-7.51 (m, 1H), 7.37 (d, 1H, J=8), 7.09 (s, 1H), 6.69-6.66 (m, 1H), 6.65-6.62 (m, 1H), 2.81 (s, 6H), 2.40 (s, 3H). $^{13}$C NMR (400 MHz, DMSO-d$_6$) δ 165.0, 147.3, 141.6, 139.3, 132.7, 129.49, 129.46, 125.0, 124.7, 123.0, 122.1, 88.4, 44.7, 14.9. FT-IR (thin film, cm$^{-1}$) 3347, 3215, 1673. MS Calcd for C$_{12}$H$_7$ClN$_2$S: [M]=288. Found: [M+H]$^+$=289. HRMS Calcd for C$_{15}$H$_{16}$N$_2$O$_2$S: [M+H]$^+$=288.1005, [M+Na]$^+$=311.0825. Found: [M+H]$^+$=289.1022, [M+Na]$^+$=311.0838. mp=138-140° C.

Step 3: 4-(5-Methylthiophen-2-yl)phthalazin-1(2H)-one 2-(Dimethylamino)-3-hydroxy-3-(5-methylthiophen-2-yl)isoindolin-1-one (1.1 g, 0.40 mmol), EtOH (4.0 mL), and hydrazine (0.19 mL, 59 mmol) were added into a RBF fitted with a reflux condenser. A nitrogen balloon was attached on top of the condenser. After refluxing overnight, the reaction was cooled to room temperature. An off-white solid precipitated. After cooling to 0° C., water was added. The solid was filtered off with an aid of water and dried under vacuum to afford a white solid, 4-(5-methylthiophen-2-yl)phthalazin-1(2H)-one (0.82 g, 85% yield).

$^1$H NMR (400 MHz, CDCl$_3$) δ 10.57 (s, 1H), 8.50-8.39 (m, 1H), 8.14-8.04 (m, 1H), 7.83-7.69 (m, 2H), 7.20-7.17 (m, 1H), 6.82-6.71 (m, 1H), 2.47 (s, 3H). $^{13}$C NMR (400 MHz, CDCl$_3$) δ 159.9, 142.5, 141.1, 134.3, 133.7, 131.7, 129.4, 128.8, 128.3, 127.1, 126.6, 125.8, 15.4. FT-IR (thin film, cm$^{-1}$) 2891, 1660, 1334. MS Calcd for C$_{13}$H$_{10}$N$_2$OS: [M]$^+$=242. Found: [M+H]$^+$=243. HRMS Calcd for C$_{13}$H$_{10}$N$_2$OS: [M+H]$^+$=243.0587. Found: [M+H]$^+$=243.0581. mp=191-194° C.

Alternatively, starting material 3 was prepared as follows:

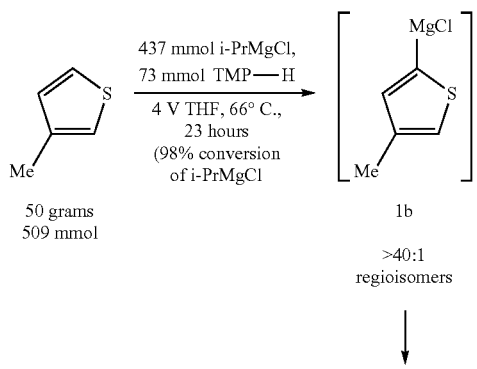

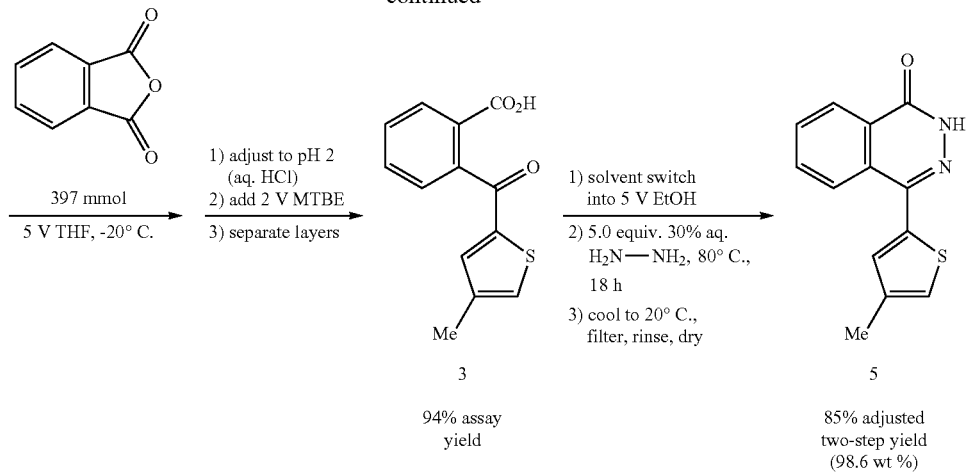

The above scheme depicts the process by which intermediate-scale synthesis of thiophene-phthalazinone 5 (shown above) was prepared. Treatment of 50 grams of 3-methylthiophene with i-PrMgCl at 66° C. in the presence of catalytic TMP-H resulted in 98% conversion to the reactive species 1b with a >40:1 regioisomeric ratio. After cooling to 20° C., this mixture was added dropwise to a −20° C. slurry of phthalic anhydride in THF to provide keto acid 3 in 94% assay yield. While this intermediate could be crystallized from toluene/heptane, the crude reaction mixture was taken directly in a through-process conversion to the phthalazinone 5. To that end, removal of THF, MTBE, and residual 3-methylthiophene was accomplished through a distillative solvent switch into ethanol. The resulting solution of 3 was exposed to aqueous hydrazine at 80° C. After 18 hours, the reaction was cooled and the precipitated product was filtered directly at 20° C. This process provided 82.7 grams of 98.6 wt % thiophene-phthalazinone 5 in a weight-adjusted 85% yield over the two steps.

LCMS Method:

Samples were run on a Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (AcCN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Other methods may also be used to synthesize AMG 900. Many synthetic chemistry transformations, as well as protecting group methodologies, useful in synthesizing AMG 900, are known in the art. Useful organic chemical transformation literature includes, for example, R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

AMG 900 was tested for its ability to reduce or inhibit tumor progression in various cell lines (in-vitro) and multiple solid tumor types (in-vivo), some of which have previously been exposed to and developed resistance to standard-of-care antimitotic agents, including taxanes and vinca alkaloids, as well as to other chemotherapeutic agents. The following Examples and resulting data will illustrate the ability of AMG 900 to treat cancer, including cancer resistant to the presently standard-of-care therapies, including antimitotic agents, such as paclitaxel, and other drugs used in conjunction with chemotherapy, such as doxorubicin. Unless otherwise indicated, the free base form of AMG 900 was used in the Examples described hereinbelow.

The following Examples describe the efforts of identifying and characterizing various crystalline solid state forms of various salts of AMG 900. Some attempts at forming a solid state crystalline form of a given salt failed, as shown in table 1 hereinbelow. To this end, synthesizing and/or forming &isolating a crystalline solid state form of AMG 900 was not, in any way, straightforward or routine. Rather, the ability to prepare and identify a crystalline solid state form of AMG 900 depended upon the particular salt of AMG 900 and/or the crystallization conditions employed.

Identification of an AMG 900 Crystalline Salt Form for Development

The stable anhydrous free base crystalline form A of AMG 900 was found to be poorly soluble in water and to possess low bioavailability in dogs. Accordingly, it was desirable to identify potential salt forms that possessed improved solubility, improved stability, improved bioavailability and/or other improved pharmacokinetic (pK) and/or pharmacodynamics (PD) properties of AMG 900. To this end, a various crystalline forms of different pharmaceutically acceptable salts of AMG 900 were investigated and made.

A number of acids (containing one pKa less than or equal to about 5) and urea were investigated, and used as potential counter-ions to form various crystalline and/or co-crystalline salts of AMG 900. Of the acid derived counterions investigated, the adipate, ascorbate, benzoate, glutamate, glutarate, glycolate, lactate, phosphate, sorbate, succinate and tartrate salts did not produce a single crystalline solid state form or any crystalline forms of AMG 900 in the conditions utilized. The remaining acid addition counter-ion salts investigated, ie., methanesulfonate, hydrochloride, besylate, tosylate, sulfate, acetate, fumarate, maleate, glucuronate, citrate, malate and malonate, did show distinct crystalline phases, ie. each counter ion salt did provide one or more crystalline forms of AMG 900. However, stability of many of the crystalline forms identified across the different counter ion salts were generally deemed not acceptable or did not meet the criteria set for clinical development. Of these crystalline salt forms of AMG 900 identified and characterized, the mesylate and bismesylate crystalline forms were found to possess the requisite stability, crystallinity and/or solubility properties deemed suitable for clinical development (See Table 1). The urea cocrystal was generally found to be stable, crystalline and soluble, however the urea co-crystalline salt was generally found to be less stable in the drug product formulation than the methanesulfonate salt(s).

TABLE 1

AMG 900 Salt Identification Results Summary

| Counterion | Results |
|---|---|
| methanesulfonate | Crystalline (Form B); stable, soluble |
| methanesulfonate | Crystalline (7 forms); metastable |
| hydrochloride | Crystalline (5 forms); low solubility |
| besylate | Crystalline; low solubility |
| tosylate | Crystalline; low solubility |
| sulfate | Crystalline (5 forms); solvated |
| acetate | Crystalline; low solubility |
| fumarate | Crystalline; low solubility |
| maleate | Crystalline; low solubility |
| urea | Crystalline (2 forms); stable, soluble, poor stability in drug product |
| glucuronate | Partially Crystalline; low solubility |
| citrate | Partially Crystalline |
| malate | Partially Crystalline |
| malonate | Partially Crystalline |
| adipate | No new crystalline form observed |
| ascorbate | No new crystalline form observed |
| benzoate | No new crystalline form observed |
| glutamate | No new crystalline form observed |
| glutarate | No new crystalline form observed |
| glycolate | No new crystalline form observed |
| lactate | No new crystalline form observed |
| phosphate | No new crystalline form observed |
| sorbate | No new crystalline form observed |
| succinate | No new crystalline form observed |
| tartarate | No new crystalline form observed |

The following Examples are representative of the present invention, and are not intended in any way to limit the scope of the present invention to the specific crystalline salt forms exemplified hereinbelow.

Abbreviations Used Herein and in the Examples

Soln solution
hr hour
rt or RT room temperature
MeOH methanol
EtOH ethanol
IPA isopropyl alcohol
MTBE methyl tert-butyl ether
2-BuOH 2-butanol
1-BuOH 1-butanol
EtOAc ethyl acetate
MeCN acetonitrile
MEK methyl ethyl ketone
THF tetrahydrofuran
DCM dichloromethane
TFE 2,2,2-trifluoroethanol Analytical Techniques Used to Characterize the Product Crystals Dynamic Vapor Sorption/Desorption (DVS)

Moisture uptake of a given AMG 900 salt crystalline form was assessed by dynamic vapor sorption (DVS). Moisture sorption/desorption data was collected on a Surface Measurement System (SMS) DVS-Advantage vapor sorption analyzer (SMS, Alperton, Middlesex, UK). The sorption and desorption data was collected over a range of 0 to 95% relative humidity (RH) at 25° C. with 5-10% RH intervals under a nitrogen purge. Equilibrium criteria used for analysis were less than 0.002% weight change in 5 minutes, with a maximum equilibrium time of 120 minutes if the weight criterion was not met.

X-Ray Powder Diffraction (XRPD)

X-ray diffraction patterns were obtained on a PANalytical X'Pert PRO X-ray diffraction system (Almelo, the Netherlands). Samples were scanned in continuous mode from 5-45° (2θ) or 5-30° (2θ) with step size of about 0.0334° on a spinning stage at 45 kV and 40 mA with CuKα radiation (1.54 Å). The incident beam path was equipped with a 0.02 rad soller slit, 15 mm mask, 4° fixed anti-scatter slit and a programmable divergence slit. The diffracted beam was equipped with a 0.02 rad soller slit, programmable anti-scatter slit and a 0.02 mm nickel filter. Detection was accomplished with an RTMS detector (X'Cellerator). The samples were sprinkled on zero background sample holder and analyzed at room temperature. Dimethanesulfonate Form E, Dimethanesulfonate Form F and Dimethanesulfonate Form G were analyzed on a TTK-450 stationary stage at the temperature noted.

It is noted that peak shifts of about +/−0.10 degrees can occur in XRPD patterns and could be caused by factors such as sample preparation and instrument alignment.

Stability Studies

Stability data was obtained for up to 3 months storage at the long term storage condition of 30° C./65% RH and at the accelerated condition of 40° C./75% RH for unmilled drug substance. The results of physical and chemical stability tests remain within specifications under these conditions. A provisional re-test period of 12 months is proposed for AMG 900 bis-mesylate dihydrate drug substance stored at the recommended condition of not more than 30° C. As additional stability data become available, the re-test period will be appropriately extended.

An Exemplary Method for Solid Stability Studies

Approximately 10 mg of a selected crystalline form of AMG 900 was weighed into a glass 100 mL volumetric flask and either capped or left open according to the preset conditions in a stability chamber or over. Another 10 mg was weighed into a 4 mL glass vial and placed under the same conditions. At each time point one flask was removed from the chamber or over, diluted with methanol to the 100 mL mark and analyzed by HPLC for purity and label claim % compared to the standard. Also at each time point one vial was removed from the chamber and the contents were analyzed by XRPD, TGA and/or DSC.

For photostability studies, enough sample was placed in a open 100 mL glass crystallization dish and exposed to 1×ICH dose for UV and visible light. Samples were weighed out for HPLC, XRPD, TGA and DSC analysis as above after the exposure to light.

Solubility Studies

An excess of solid material was stirred at 25° C. or 55° C. for 18-24 hrs in aqueous media, excipients or solvents as noted. At the appropriate time point, an aliquot of the sample was centrifuged. The supernatant was filtered through a PTFE syringe filter and analyzed by HPLC versus a standard curve. The solid was then analyzed by XRPD for identification of the form.

Solution stability studies were conducted according to the stability guideline (GL0037.00) at 0.05 mg·mL in 50% acetonitrile. The acid (300 mM HCl, pH 0.5), base (10 mM phosphate buffer, pH 12), neutral (10 mM phosphate buffer pH 8.0) and peroxide (10 mM phosphate buffer, pH 8.0, 0.1% $H_2O_2$) samples were stirred at 55° C. in crimped amber vials. The photostability samples were placed in capped quartz cuvettes and glass vials and placed in the photostability chamber for exposure to 1×ICH dose for UV and visible light. Samples were analyzed by HPLC for purity and label claim % compared to a standard.

Thermal Analysis

Differential scanning calorimetry was conducted on a Q100 (TA Instruments) from 30° C. to 300° C. at 10° C./minute in a crimped aluminum pan unless otherside specified. Thermogravimetric analysis (TGA) was performed on a Q500 (TA Instruments) from 30° C. to 300° C. at 10° C./minute in a platinum pan.

Melting Points:

Unless otherwise reported herein, the various crystalline forms of various salts of AMG 900 did not achieve a definitive melting point or temperature range. Instead, the material typically first desolvated resulting in a different, identified crystalline form, and then melted. To this end, such melting points are reported herein as "undefined."

Example 3

Preparation of Methanesulfonate Salt Crystalline Form A of AMG 900

To a flask containing a solution of AMG 900 freebase (1.0 gram, 1.99 mmol) in N,N-dimethylformamide (2 mL) was added methanesulfonic acid (0.13 mL, 1.99 mmol). Added tert-butyl methyl ether (2 mL) then immerse the mixture in a 70° C. oil bath or other heat source. Additional tert-butyl methyl ether (2 mL) followed by additional N,N-dimethylformamide (1 mL) was added to the mixture. The mixture began to precipitate and the forming solids formed needle shaped crystals. The mixture was cooled to 20° C. and stirred for 48 hours. Crystalline solid state Form A of the methanesulfonate salt of AMG 900 was isolated (0.56 grams).

NMR data for AMG 900 methanesulfonate salt crystalline Form A: $^1$H NMR (400 MHz, DMSO-$d_6$) δ ppm 8.85 (m, 1H), 8.51 (m, 1H), 8.41 (m, 2H), 8.30 (dd, 1H), 8.23 (m, 2H), 7.74 (d, 2H), 7.62 (d, 1H), 7.47 (s, 1H), 7.36 (m, 4H), 2.35 (d, 3H), 2.32 (s, 3H)

Melting Point for AMG 900 Methanesulfonate Salt Crystalline Form A: Undefined

TABLE 2

AMG 900 Methanesulfonate Salt Form A XRPD pattern data

| Pos. [°2Th.] | FWHM [°2Th.] | d-spacing [Å] |
|---|---|---|
| 8.29 | 0.13 | 10.67 |
| 8.55 | 0.10 | 10.34 |
| 9.89 | 0.16 | 8.94 |
| 10.76 | 0.13 | 8.22 |
| 11.55 | 0.13 | 7.66 |
| 12.24 | 0.16 | 7.23 |
| 12.96 | 0.10 | 6.83 |
| 14.20 | 0.13 | 6.24 |
| 15.04 | 0.13 | 5.89 |
| 16.52 | 0.10 | 5.37 |
| 17.22 | 0.19 | 5.15 |
| 17.84 | 0.16 | 4.97 |
| 18.66 | 0.10 | 4.76 |
| 19.18 | 0.16 | 4.63 |
| 20.05 | 0.10 | 4.43 |
| 20.39 | 0.19 | 4.36 |
| 21.55 | 0.19 | 4.12 |
| 23.21 | 0.16 | 3.83 |
| 23.56 | 0.16 | 3.78 |
| 24.58 | 0.13 | 3.62 |
| 25.22 | 0.10 | 3.53 |
| 25.77 | 0.06 | 3.46 |
| 25.99 | 0.13 | 3.43 |
| 27.30 | 0.13 | 3.27 |
| 28.07 | 0.10 | 3.18 |
| 28.51 | 0.13 | 3.13 |
| 29.08 | 0.26 | 3.07 |
| 29.58 | 0.13 | 3.02 |
| 30.29 | 0.16 | 2.95 |
| 31.19 | 0.13 | 2.87 |
| 31.74 | 0.13 | 2.82 |
| 32.77 | 0.16 | 2.73 |
| 33.68 | 0.19 | 2.66 |
| 34.59 | 0.13 | 2.59 |

The X-ray powder diffraction (XRPD) spectral/diagram/pattern data for the AMG 900 methanesulfonate salt crystalline Form A is set forth in FIG. 1.

Example 4

Preparation of Bismesylate (Dimethanesulfonate) Salt Crystalline Form A of AMG 900

Free base AMG 900 crystalline Form A (26 mg) was dissolved at about 0.6 mg/mL in MeCN at 55° C., the mixture to which about 4 uL (1 eq) of methanesulfonic acid was added. The mixture was stirred overnight at RT, then allowed to evaporate at RT, at which point crystalline solid state bismesylate salt Form A of AMG 900 formed.

NMR Data for the AMG 900 Bismesylate (Dimethatesulfonate) Salt Crystalline Form A: $^1$H NMR (400 MHz, DMSO-$d_6$) δ ppm 2.31-2.37 (m, 3H) 3.72 (br. s., 6H) 3.94 (br. s., 2H) 7.32-7.43 (m, 2H) 7.71 (d, J=8.80 Hz, 1H) 8.24-8.33 (m, 1H) 8.40-8.44 (m, 1H)

Melting Point for the AMG 900 Dimethanesulfonate Salt Crystalline Form A: Undefined

TABLE 3

AMG 900 Bismesylate (Dimethatesulfonate) Salt Crystalline Form A XRPD pattern data

| Pos. [°2Th.] | FWHM [°2Th.] | d-spacing [Å] |
|---|---|---|
| 5.60 | 0.10 | 15.79 |
| 8.07 | 0.10 | 10.96 |
| 11.17 | 0.13 | 7.92 |
| 12.24 | 0.13 | 7.23 |
| 12.58 | 0.10 | 7.03 |
| 13.64 | 0.19 | 6.49 |

TABLE 3-continued

AMG 900 Bismesylate (Dimethatesulfonate) Salt Crystalline Form A XRPD pattern data

| Pos. [°2Th.] | FWHM [°2Th.] | d-spacing [Å] |
|---|---|---|
| 14.55 | 0.16 | 6.09 |
| 15.06 | 0.13 | 5.88 |
| 15.72 | 0.10 | 5.64 |
| 16.36 | 0.13 | 5.42 |
| 16.76 | 0.13 | 5.29 |
| 17.16 | 0.52 | 5.17 |
| 17.52 | 0.13 | 5.06 |
| 18.37 | 0.13 | 4.83 |
| 19.27 | 0.16 | 4.61 |
| 20.24 | 0.13 | 4.39 |
| 20.80 | 0.13 | 4.27 |
| 21.45 | 0.13 | 4.14 |
| 21.80 | 0.13 | 4.08 |
| 22.40 | 0.13 | 3.97 |
| 22.74 | 0.10 | 3.91 |
| 23.16 | 0.13 | 3.84 |
| 23.63 | 0.13 | 3.77 |
| 24.01 | 0.13 | 3.71 |
| 24.59 | 0.10 | 3.62 |
| 24.83 | 0.10 | 3.59 |
| 25.28 | 0.19 | 3.52 |
| 26.45 | 0.10 | 3.37 |
| 26.72 | 0.13 | 3.34 |
| 27.28 | 0.19 | 3.27 |
| 28.09 | 0.19 | 3.18 |
| 29.94 | 0.32 | 2.98 |
| 30.40 | 0.26 | 2.94 |
| 31.02 | 0.13 | 2.88 |
| 31.88 | 0.26 | 2.81 |
| 32.37 | 0.16 | 2.77 |
| 33.25 | 0.19 | 2.69 |
| 33.58 | 0.13 | 2.67 |
| 33.92 | 0.16 | 2.64 |
| 34.40 | 0.19 | 2.61 |

The X-ray powder diffraction (XRPD) data for the bis-mesylate (dimethatesulfonate) salt crystalline Form A is set forth in FIG. 2.

Example 5

Preparation of Bismesylate (Dimethanesulfonate) Salt Crystalline Form B of AMG 900

A 4 mL glass vial was charged with 41 mg of AMG 900 freebase crystalline Form A. Methanesulfonic acid (4 mL) was added to the vial forming a solution. The solution was left uncapped at room temperature to evaporate, yielding crystalline solid state bismesylate salt Form B of AMG 900.

Alternatively, the titled compound was prepared by the following method: Acetic acid (12.3 mL), water (12.2 mL) and methanesulfonic acid (2.8 grams, 29.1 mmol) were combined to give a solution which was then added to a flask containing AMG 900 freebase (Form A anhydrous, 7.26 grams, 14.6 mmol). The resulting solution was stirred at about 20° C. till a homogeneous solution resulted. The solution was filtered through a 1 μm frit into a three-neck, 250 mL round bottom flask fitted with overhead stirring. The solution was heated to 50° C. internal temperature then 2-propanol (12.2 mL) was added maintaining internal temperature. The resulting homogeneous solution was cooled to 40° C. and then seeded with 5 wt % AMG 900 bismesylate dihydrate form B (0.74 grams, 1.0 mmol; spontaneous crystallization will occur in unseeded crystallizations upon cooling of the batch. Thus, a small amount of the homogenous solution can be removed and cooled to initiate such spontaneous crystallization and the resulting crystalline bis-mesylate Form B material is used as a seed, to initiate crystallization of the main batch solution). The resulting suspension was held at 40° C. for 45 minutes then cooled to 20° C. over 2 hours and maintained at 20° C. for an additional 30 minutes. 2-Propanol (68.8 mL) was then added to the reaction flask at a constant rate over 3 hours by syringe pump. The resulting slurry was aged 12-18 hours at 20° C. then filtered through a medium porosity filter. The product cake was displacement washed with 7.3 mL of 78:11:11 v/v IPA/AcOH/water. The filter cake was further displacement washed with 2.0 Vol (14.7 mL) 2-propanol then dried under humid nitrogen sweep to give crystalline AMG 900 bismesylate (dimethanesulfonate) dihydrate form B.

NMR Data for Bismesylate (Dimethanesulfonate) Salt Crystalline Form B: $^1$H NMR (CD$_3$OD, 400 MHz) δ 8.80 (d, 1H), 8.69 (d, 1H), 8.61 (d, 1H), 8.41 (d, 1H), 8.35 (m, 1H), 8.29 (m, 2H), 7.87 (m, 1H), 7.74 (m, 2H), 7.58 (s, 1H), 7.51 (m, 2H), 7.40 (m, 2H), 4.83 (s, ~14H, H$_2$O), 2.70 (s, 3H), 2.70 (s, 3H), 2.40 (d, 3H).

AMG 900 bis-mesylate dihydrate, $C_3H_{29}N_7O_7S_3 \cdot 2H_2O$, has a formula weight of 731.82 g/mole (503.58 g/mole as the free base). Form B is a the thermodynamically stable form, and is a white to brown in color non-hygroscopic crystalline material.

Melting Point for the Dimethanesulfonate Salt (Form B): Undefined. The product first desolvates then melts as dimethanesulfonate salt Form F.

TABLE 4

AMG 900 Bismesylate (Dimethanesulfonate) Salt Crystalline Form B XRPD pattern data.

| Pos. [°2Th.] | FWHM [°2Th.] | d-spacing [Å] |
|---|---|---|
| 7.44 | 0.13 | 11.89 |
| 8.34 | 0.10 | 10.60 |
| 9.28 | 0.13 | 9.53 |
| 10.75 | 0.16 | 8.23 |
| 11.22 | 0.19 | 7.89 |
| 12.66 | 0.10 | 6.99 |
| 12.88 | 0.10 | 6.88 |
| 13.75 | 0.13 | 6.44 |
| 14.29 | 0.13 | 6.20 |
| 14.66 | 0.13 | 6.04 |
| 15.07 | 0.13 | 5.88 |
| 15.67 | 0.10 | 5.65 |
| 15.92 | 0.16 | 5.57 |
| 16.28 | 0.10 | 5.44 |
| 16.90 | 0.13 | 5.25 |
| 17.17 | 0.10 | 5.16 |
| 17.98 | 0.16 | 4.93 |
| 18.59 | 0.10 | 4.77 |
| 18.82 | 0.13 | 4.72 |
| 19.74 | 0.16 | 4.50 |
| 20.05 | 0.10 | 4.43 |
| 20.49 | 0.16 | 4.34 |
| 20.85 | 0.10 | 4.26 |
| 21.13 | 0.10 | 4.21 |
| 21.46 | 0.10 | 4.14 |
| 21.81 | 0.10 | 4.08 |
| 22.08 | 0.16 | 4.03 |
| 22.44 | 0.13 | 3.96 |
| 22.90 | 0.13 | 3.88 |
| 23.62 | 0.13 | 3.77 |
| 24.10 | 0.23 | 3.69 |
| 24.93 | 0.19 | 3.57 |
| 25.37 | 0.16 | 3.51 |
| 26.18 | 0.13 | 3.40 |
| 26.45 | 0.13 | 3.37 |
| 27.02 | 0.16 | 3.30 |
| 27.58 | 0.19 | 3.23 |
| 27.87 | 0.10 | 3.20 |
| 28.51 | 0.19 | 3.13 |
| 29.32 | 0.13 | 3.05 |

TABLE 4-continued

AMG 900 Bismesylate (Dimethanesulfonate) Salt
Crystalline Form B XRPD pattern data.

| Pos. [°2Th.] | FWHM [°2Th.] | d-spacing [Å] |
|---|---|---|
| 29.53 | 0.10 | 3.03 |
| 30.12 | 0.19 | 2.97 |
| 30.80 | 0.13 | 2.90 |
| 31.60 | 0.16 | 2.83 |
| 32.22 | 0.23 | 2.78 |
| 33.17 | 0.16 | 2.70 |
| 33.44 | 0.13 | 2.68 |
| 34.14 | 0.19 | 2.63 |
| 34.47 | 0.19 | 2.60 |

Figure 4:
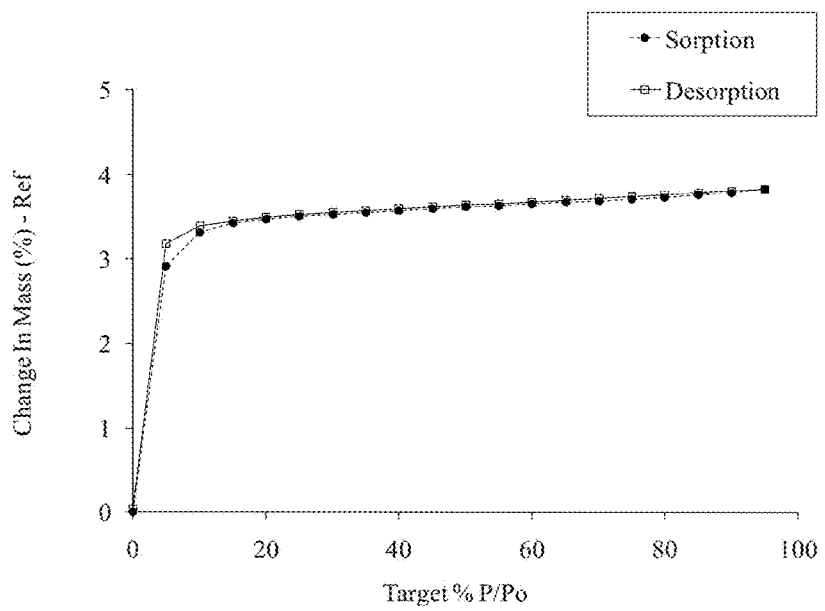
FIG. 4 is a graph depicting the dynamic vapor sorption (DVS) data for the dimethanesulfonate salt (crystalline Form B) of AMG 900.

The X-ray powder diffraction (XRPD) pattern data for the bismesylate (dimethanesulfonate) salt crystalline Form B is set forth in FIG. 3, and dynamic vapor sorption (DVS) data for the Dimethanesulfonate Salt crystalline Form B is set forth in FIG. 4.

Stability data for AMG 900 bismesylate (dimethanesulfonate) salt crystalline Form B was obtained for up to 3 months storage at the long term storage condition of 30° C./65% RH and at the accelerated condition of 40° C./75% RH for unmilled drug substance. This solid state Form B was found to be stable. The results of physical and chemical stability tests remain within desired specifications under these conditions. Table 4-A presents 12 month stability data for AMG 900 bis-mesylate dihydrate crystalline Form B when tested at 30° C./65% RH.

TABLE 4-A

| | | Test | | | | |
|---|---|---|---|---|---|---|
| | Acceptance Criteria | Initial Period Time 0 | 3 months | 6 months | 9 months | 12 months |
| Description | White to brown powder | conforms | conforms | conforms | conforms | conforms |
| Assay (% w/w) | 97.0-103.0 | 98.1 | 99.2 | 99.1 | 101.2 | 100.1 |
| Total Impurities (%) | < or = 2.0 | 0.35 | 0.21 | 0.16 | 0.25 | 0.26 |
| 4-aminophenol content (ppm) | < or = 500 | <20 | <20 | <20 | <20 | <20 |
| Intermediate* content (ppm) | < or = 500 | | | | | 171 |
| Water content (%) | Report | 5.0 | 5.1 | 5.2 | 5.2 | 5.2 |

*Intermediate is 4-(2-(4-aminophenoxy)pyridin-3-yl)pyrimidin-2-amine

Further, the bismesylate dehydrate crystalline form B of AMG 900 provided acceptable physiochemical properties and exposure in a dog pK study.

Example 6

Preparation of Bismesylate (Dimethanesulfonate) Salt Crystalline Form C of AMG 900

AMG 900 freebase crystalline Form A (4.7 grams, 9.3 mmol) was dissolved in DMSO to give a homogeneous solution. Water (0.42 mL, 23.3 mmol) and methanesulfonic acid (1.3 mL, 20.5 mmol) were added to the reaction. Tetrahydrofuran (43 mL) was then added and the mixture became a cloudy solution. The solution was seeded with AMG 900 bismesylate salt Form C (50 mg; where seed material is not available, a small aliquot of the cloudy solution will spontaneously crystallize upon further aging at room temperature. This bismesylate crystalline From C material can serve as seed material in order to initiate crystallization of larger batches/solutions) to initiate crystallization. After about 10 min a thick slurry formed. The slurry was heated to about 70° C. and to it was added 15 ml of THF to result in a thin slurry of crystals with needle-like shape, as viewed by microscopy. The slurry was cooled to 20° C. The supernatant was assayed and provided an about 1.2 mg/mL concentration of AMG 900. The slurry was filtered and the filter cake product was washed with THF to give AMG 900 bismesylate (dimethanesulfonate) salt crystalline Form C.

NMR Data for AMG 900 Bismesylate (Dimethatesulfonate) Salt Crystalline Form C: $^1$H NMR (400 MHz, DMSO-$d_6$) δ ppm 8.90 (m, 1H), 8.54 (m, 1H), 8.49 (d, 1H), 8.44 (dd, 1H), 8.36 (dd. 1H), 8.30 (m, 2H), 7.79 (m, 2H), 7.66 (d, 1H), 7.56 (d, 1H), 7.53 (m, 1H), 7.42 (m, 3H), 2.36 (m, 9H)

Melting Point for the Dimethanesulfonate Salt (Form C): Undefined

TABLE 5

AMG 900 Bismesylate (Dimethatesulfonate) Salt
Crystalline Form C XRPD pattern data

| Pos. [°2Th.] | FWHM [°2Th.] | d-spacing [Å] |
|---|---|---|
| 8.29 | 0.10 | 10.66 |
| 8.55 | 0.10 | 10.34 |
| 10.78 | 0.10 | 8.21 |
| 12.96 | 0.10 | 6.83 |
| 14.20 | 0.13 | 6.24 |
| 15.05 | 0.10 | 5.89 |
| 16.51 | 0.23 | 5.37 |
| 17.25 | 0.10 | 5.14 |
| 17.62 | 0.10 | 5.03 |
| 17.91 | 0.10 | 4.95 |
| 18.67 | 0.13 | 4.75 |
| 19.40 | 0.19 | 4.58 |
| 20.05 | 0.10 | 4.43 |
| 20.40 | 0.10 | 4.35 |

TABLE 5-continued

AMG 900 Bismesylate (Dimethatesulfonate) Salt
Crystalline Form C XRPD pattern data

| Pos. [°2Th.] | FWHM [°2Th.] | d-spacing [Å] |
|---|---|---|
| 20.55 | 0.10 | 4.32 |
| 21.58 | 0.13 | 4.12 |
| 22.71 | 0.16 | 3.92 |
| 23.60 | 0.10 | 3.77 |
| 24.59 | 0.13 | 3.62 |
| 25.21 | 0.16 | 3.53 |
| 26.00 | 0.10 | 3.43 |
| 26.24 | 0.13 | 3.40 |
| 27.62 | 0.13 | 3.23 |
| 28.08 | 0.13 | 3.18 |
| 28.52 | 0.10 | 3.13 |
| 29.13 | 0.16 | 3.07 |
| 29.58 | 0.10 | 3.02 |
| 30.30 | 0.19 | 2.95 |
| 30.73 | 0.19 | 2.91 |
| 31.20 | 0.13 | 2.87 |
| 31.76 | 0.16 | 2.82 |
| 32.81 | 0.19 | 2.73 |
| 33.66 | 0.19 | 2.66 |
| 34.59 | 0.19 | 2.59 |

Figure 6:
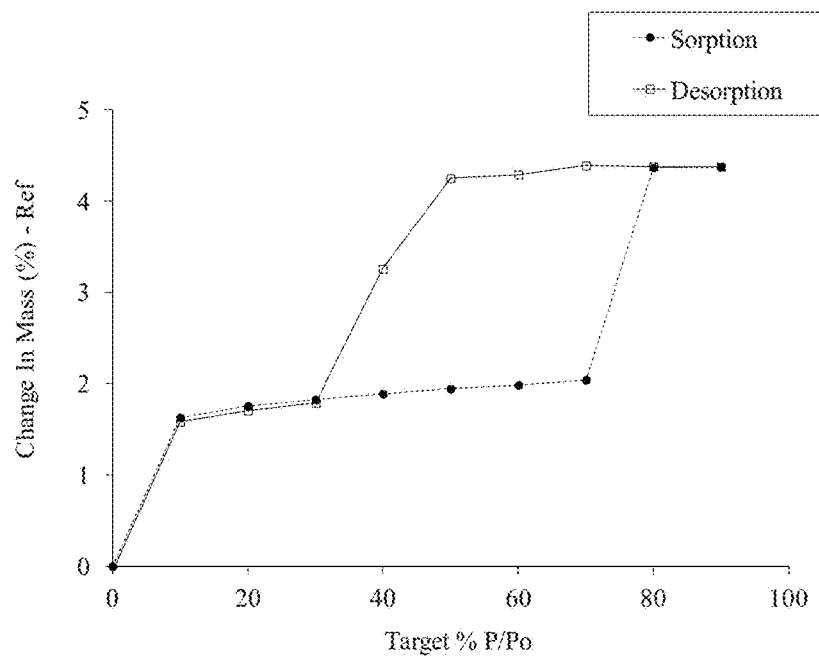
FIG. 6 is a graph depicting the dynamic vapor sorption (DVS) data for the dimethanesulfonate salt (crystalline Form C) of AMG 900.

The X-ray powder diffraction (XRPD) pattern data for AMG 900 bismesylate (dimethatesulfonate) salt crystalline Form C is set forth in FIG. 5, and dynamic vapor sorption (DVS) data for the Dimethatesulfonate Salt (Form C) is set forth in FIG. 6.

Example 7

Preparation of Bismesylate (Dimethanesulfonate) Salt Crystalline Form D of AMG 900

A slurry of 200 mg of crystalline AMG 900 dimethanesulfonate crystalline Form B and 20 mg AMG 900 dimethansulfonate crystalline Form A was stirred in MeCN for 24 hrs at room temperature. The resulting slurry/mixture was filtered, then allowed to air dry to provide the product, crystalline AMG 900 bismesylate (dimethylsulfonate) salt Form D.

Melting Point for the Dimethanesulfonate Salt (Form D): Undefined

TABLE 6

AMG 900 Bismesylate (dimethatesulfonate) Salt
Form D XRPD pattern data

| Pos. [°2Th.] | FWHM [°2Th.] | d-spacing [Å] |
|---|---|---|
| 6.88 | 0.16 | 12.84 |
| 7.70 | 0.10 | 11.48 |
| 8.89 | 0.13 | 9.95 |
| 9.59 | 0.13 | 9.22 |
| 10.52 | 0.10 | 8.41 |
| 11.57 | 0.13 | 7.65 |
| 12.81 | 0.13 | 6.91 |
| 13.46 | 0.13 | 6.58 |
| 13.80 | 0.13 | 6.42 |
| 15.35 | 0.13 | 5.77 |
| 16.61 | 0.10 | 5.34 |
| 16.89 | 0.13 | 5.25 |
| 17.44 | 0.10 | 5.08 |
| 17.79 | 0.16 | 4.99 |
| 18.70 | 0.26 | 4.74 |
| 19.69 | 0.19 | 4.51 |
| 20.74 | 0.16 | 4.28 |
| 21.53 | 0.16 | 4.13 |
| 22.02 | 0.16 | 4.04 |
| 23.14 | 0.19 | 3.84 |
| 23.88 | 0.16 | 3.73 |
| 24.63 | 0.13 | 3.62 |
| 25.03 | 0.16 | 3.56 |
| 25.78 | 0.16 | 3.46 |
| 26.43 | 0.13 | 3.37 |
| 26.73 | 0.10 | 3.34 |
| 27.07 | 0.16 | 3.29 |
| 27.58 | 0.10 | 3.23 |
| 28.08 | 0.13 | 3.18 |
| 28.72 | 0.19 | 3.11 |
| 29.38 | 0.16 | 3.04 |
| 29.69 | 0.16 | 3.01 |
| 31.21 | 0.13 | 2.87 |
| 31.52 | 0.13 | 2.84 |
| 31.96 | 0.10 | 2.80 |
| 32.52 | 0.13 | 2.75 |
| 33.60 | 0.19 | 2.67 |
| 34.10 | 0.19 | 2.63 |

Figure 8:
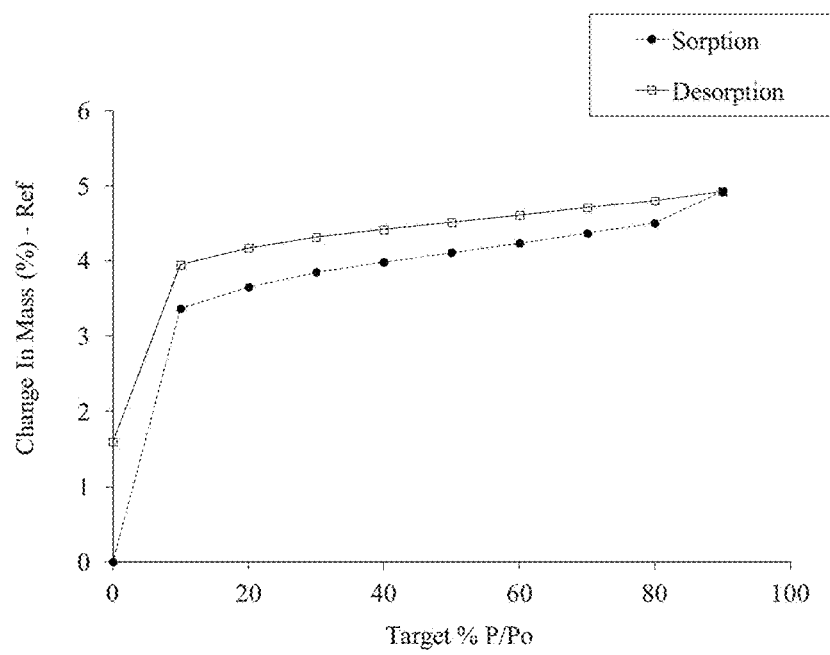
FIG. 8 is a graph depicting the dynamic vapor sorption (DVS) data for the dimethanesulfonate salt (crystalline Form D) of AMG 900.

The X-ray powder diffraction (XRPD) pattern data for crystalline AMG 900 bismesylte (dimethatesulfonate Salt crystalline Form D is set forth in FIG. 7, and dynamic vapor sorption (DVS) data for the Dimethatesulfonate Salt (Form D) is set forth in FIG. 8.

Relationship Between the AMG 900 Bismesylate Salt Crystalline Form a, Crystalline Form B, Crystalline Form C and Crystalline Form D AMG 900 bismesylate salt crystalline From A was identified as a dihydrate; AMG 900 bismesylate salt crystalline From B was identified as a dihydrate; AMG 900 bismesylate salt crystalline From C was identified as a monohydrate; and AMG 900 bismesylate salt crystalline From D was identified as a monohydrate. The AMG 900 bis-mesylate dihydrate crystalline form B appeared to be the most stable form of the four crystalline forms. Both monohydrate forms C & D convert to the dihydrate form B with an increase in humidity, and particularly at relative humidity at or greater than 50%. The dihydrate form A converts to form B over time at room temperature in a capped vial. The bis-mesylate dihydrate form B itself is stable to humidity changes above 10% RH (See DVS isotherm shown in FIG. 5). This indicates that form B is stable under the conditions tested.

Example 8

Preparation of Bismesylate (Dimethanesulfonate) Salt Crystalline Form E of AMG 900

Bismesylate salt crystalline Form B of AMG 900 was heated to about 110° C. and afforded monohydrate bismesylate salt crystalline form E of AMG 900.

Melting Point for the Dimethanesulfonate Salt (Form E): Undefined. Form E when heated continuously desolvates then melts as dimethanesulfonate salt Form F.

TABLE 7

AMG 900 Bismesylate (dimethatesulfonate) Salt
Crystalline Form E XRPD pattern data

| Pos. [°2Th.] | FWHM [°2Th.] | d-spacing [Å] |
|---|---|---|
| 6.85 | 0.52 | 12.91 |
| 7.66 | 0.10 | 11.54 |
| 8.31 | 0.10 | 10.64 |

TABLE 7-continued

AMG 900 Bismesylate (dimethatesulfonate) Salt
Crystalline Form E XRPD pattern data

| Pos. [°2Th.] | FWHM [°2Th.] | d-spacing [Å] |
|---|---|---|
| 9.02 | 0.10 | 9.80 |
| 10.55 | 0.10 | 8.39 |
| 12.84 | 0.06 | 6.89 |
| 13.12 | 0.10 | 6.75 |
| 13.90 | 0.13 | 6.37 |
| 14.50 | 0.10 | 6.11 |
| 14.74 | 0.06 | 6.01 |
| 14.97 | 0.10 | 5.92 |
| 15.71 | 0.13 | 5.64 |
| 16.14 | 0.16 | 5.49 |
| 16.64 | 0.13 | 5.33 |
| 17.23 | 0.19 | 5.15 |
| 18.11 | 0.13 | 4.90 |
| 18.46 | 0.13 | 4.81 |
| 19.39 | 0.10 | 4.58 |
| 19.85 | 0.06 | 4.47 |
| 20.04 | 0.10 | 4.43 |
| 20.42 | 0.16 | 4.35 |
| 20.81 | 0.10 | 4.27 |
| 21.15 | 0.06 | 4.20 |
| 21.35 | 0.13 | 4.16 |
| 22.06 | 0.13 | 4.03 |
| 22.49 | 0.10 | 3.95 |
| 22.98 | 0.23 | 3.87 |
| 23.44 | 0.13 | 3.80 |
| 24.02 | 0.19 | 3.70 |
| 24.43 | 0.10 | 3.64 |
| 24.75 | 0.16 | 3.60 |
| 25.07 | 0.13 | 3.55 |
| 25.84 | 0.13 | 3.45 |
| 26.66 | 0.16 | 3.34 |
| 26.98 | 0.13 | 3.30 |
| 27.42 | 0.16 | 3.25 |
| 27.98 | 0.16 | 3.19 |
| 28.34 | 0.13 | 3.15 |
| 28.76 | 0.13 | 3.10 |
| 29.08 | 0.10 | 3.07 |
| 29.50 | 0.23 | 3.03 |
| 30.24 | 0.13 | 2.96 |
| 31.69 | 0.19 | 2.82 |
| 32.48 | 0.19 | 2.76 |
| 33.54 | 0.26 | 2.67 |
| 34.35 | 0.19 | 2.61 |

I(rel)% is the percent relative intensity based on the largest peak.

The X-ray powder diffraction (XRPD) data for the AMG 900 bismesylate (dimethatesulfonate) Salt crystalline Form E is set forth in FIG. 9 (analyzed at 110° C.). Form E was found to be unstable. If left at room temperature in conditions of normal humidity, Form E converts back to crystalline Form B.

Example 9

Preparation of Bismesylate (Dimethanesulfonate) Salt Crystalline Form F of AMG 900

Bismesylate salt crystalline Form B of AMG 900 was heated to about 170° C. and afforded monohydrate bismesylate salt crystalline form F of AMG 900.

Melting Point for the Dimethanesulfonate Salt (Form F): Onset about 163-174° C.

TABLE 8

AMG 900 Bismesylate (dimethatesulfonate) Salt
crystalline Form F XRPD pattern data

| Pos. [°2Th.] | FWHM [°2Th.] | d-spacing [Å] |
|---|---|---|
| 5.21 | 0.39 | 16.98 |
| 7.01 | 0.52 | 12.61 |
| 8.17 | 0.10 | 10.82 |
| 8.62 | 0.10 | 10.26 |
| 9.15 | 0.13 | 9.67 |
| 10.23 | 0.10 | 8.65 |
| 10.72 | 0.10 | 8.26 |
| 12.04 | 0.10 | 7.35 |
| 13.10 | 0.06 | 6.76 |
| 13.32 | 0.10 | 6.65 |
| 13.73 | 0.13 | 6.45 |
| 14.09 | 0.13 | 6.28 |
| 14.59 | 0.13 | 6.07 |
| 15.06 | 0.13 | 5.88 |
| 15.40 | 0.10 | 5.75 |
| 15.79 | 0.10 | 5.61 |
| 16.35 | 0.13 | 5.42 |
| 17.14 | 0.10 | 5.17 |
| 17.35 | 0.10 | 5.11 |
| 18.31 | 0.19 | 4.84 |
| 18.74 | 0.13 | 4.73 |
| 19.82 | 0.16 | 4.48 |
| 19.98 | 0.06 | 4.44 |
| 20.45 | 0.10 | 4.34 |
| 20.73 | 0.06 | 4.29 |
| 21.02 | 0.13 | 4.23 |
| 21.44 | 0.10 | 4.15 |
| 21.74 | 0.16 | 4.09 |
| 22.49 | 0.13 | 3.95 |
| 23.48 | 0.13 | 3.79 |
| 24.06 | 0.13 | 3.70 |
| 24.61 | 0.13 | 3.62 |
| 25.02 | 0.19 | 3.56 |
| 25.49 | 0.10 | 3.49 |
| 26.14 | 0.13 | 3.41 |
| 26.46 | 0.13 | 3.37 |
| 26.78 | 0.10 | 3.33 |
| 27.61 | 0.16 | 3.23 |
| 28.62 | 0.19 | 3.12 |
| 29.52 | 0.19 | 3.03 |
| 30.27 | 0.16 | 2.95 |
| 30.98 | 0.19 | 2.89 |
| 32.76 | 0.13 | 2.73 |
| 33.76 | 0.19 | 2.65 |
| 34.63 | 0.23 | 2.59 |

The X-ray powder diffraction (XRPD) data for AMG 900 bismesylate (dimethatesulfonate) salt crystalline Form F is set forth in FIG. 10 (analyzed at 170° C.).

Example 10

Preparation of Bismesylate (Dimethanesulfonate) Salt crystalline Form G of AMG 900

Bismesylate salt crystalline Form B of AMG 900 was heated to about 210° C. and afforded monohydrate bismesylate salt crystalline form F of AMG 900.

Melting Point for the Dimethanesulfonate Salt (Form G): Onset about 218-223° C.

TABLE 9

AMG 900 Bismesylate (Dimethatesulfonate) Salt
Crystalline Form G XRPD pattern data

| Pos. [°2Th.] | FWHM [°2Th.] | d-spacing [Å] |
|---|---|---|
| 6.83 | 0.65 | 12.95 |
| 15.94 | 0.10 | 5.56 |

TABLE 9-continued

AMG 900 Bismesylate (Dimethatesulfonate) Salt Crystalline Form G XRPD pattern data

| Pos. [°2Th.] | FWHM [°2Th.] | d-spacing [Å] |
|---|---|---|
| 16.93 | 0.13 | 5.24 |
| 17.69 | 0.06 | 5.01 |
| 17.94 | 0.13 | 4.95 |
| 18.72 | 0.13 | 4.74 |
| 18.99 | 0.10 | 4.67 |
| 19.34 | 0.10 | 4.59 |
| 19.47 | 0.10 | 4.56 |
| 20.55 | 0.10 | 4.32 |
| 21.25 | 0.16 | 4.18 |
| 22.20 | 0.13 | 4.00 |
| 22.65 | 0.10 | 3.93 |
| 23.09 | 0.10 | 3.85 |
| 23.81 | 0.13 | 3.74 |
| 23.97 | 0.10 | 3.71 |
| 25.16 | 0.10 | 3.54 |
| 25.34 | 0.10 | 3.51 |
| 25.79 | 0.13 | 3.45 |
| 27.30 | 0.13 | 3.27 |
| 27.75 | 0.16 | 3.22 |
| 28.21 | 0.10 | 3.16 |
| 29.41 | 0.16 | 3.04 |
| 29.83 | 0.16 | 3.00 |
| 30.25 | 0.26 | 2.95 |
| 30.99 | 0.19 | 2.89 |
| 31.56 | 0.16 | 2.84 |
| 32.79 | 0.13 | 2.73 |
| 33.38 | 0.10 | 2.68 |
| 34.79 | 0.39 | 2.58 |

The X-ray powder diffraction (XRPD) data for the AMG 900 bismesylte (dimethatesulfonate) Salt crystalline Form G is set forth in FIG. 11 (analyzed at 210° C.).

Example 11

Preparation of Hydrochloride Salt Crystalline Form A of AMG 900

To about 40 mg of AMG 900 free base crystalline Form A was added about 4 mL of 0.1N HCl to form a slurry. The slurry was dispersed in a sonic bath for about 1 minute, and the resulting solids were isolated by filtration. These solids were taken up in MeCN at room temperature and the resulting slurry was stirred for about 24 hr. The slurry was filtered to isolate the titled product material.
Melting Point for the Hydrochloride Salt (Form A): Undefined

TABLE 10

AMG 900 Hydrochloride Salt (Form A) XRPD pattern data

| Pos. [°2Th.] | FWHM [°2Th.] | d-spacing [Å] |
|---|---|---|
| 6.72 | 0.10 | 13.15 |
| 8.93 | 0.10 | 9.90 |
| 9.16 | 0.10 | 9.66 |
| 11.40 | 0.10 | 7.76 |
| 12.41 | 0.13 | 7.13 |
| 13.03 | 0.13 | 6.79 |
| 13.34 | 0.06 | 6.64 |
| 13.59 | 0.10 | 6.52 |
| 14.12 | 0.13 | 6.27 |
| 14.59 | 0.13 | 6.07 |
| 14.90 | 0.16 | 5.95 |
| 15.76 | 0.10 | 5.62 |
| 16.51 | 0.10 | 5.37 |
| 16.91 | 0.13 | 5.24 |
| 18.10 | 0.10 | 4.90 |
| 18.66 | 0.10 | 4.75 |
| 19.07 | 0.13 | 4.65 |
| 19.84 | 0.13 | 4.48 |
| 20.24 | 0.10 | 4.39 |
| 21.18 | 0.13 | 4.19 |
| 21.55 | 0.13 | 4.12 |
| 21.76 | 0.06 | 4.08 |
| 23.22 | 0.10 | 3.83 |
| 24.06 | 0.13 | 3.70 |
| 24.42 | 0.10 | 3.65 |
| 24.78 | 0.19 | 3.59 |
| 25.33 | 0.10 | 3.52 |
| 25.84 | 0.19 | 3.45 |
| 26.40 | 0.16 | 3.38 |
| 27.24 | 0.10 | 3.27 |
| 27.60 | 0.16 | 3.23 |
| 28.45 | 0.10 | 3.14 |
| 29.89 | 0.10 | 2.99 |
| 30.13 | 0.10 | 2.97 |
| 30.64 | 0.16 | 2.92 |
| 31.09 | 0.13 | 2.88 |
| 31.55 | 0.13 | 2.84 |
| 31.94 | 0.16 | 2.80 |
| 32.41 | 0.16 | 2.76 |
| 33.41 | 0.13 | 2.68 |
| 33.98 | 0.10 | 2.64 |
| 34.67 | 0.19 | 2.59 |

The X-ray powder diffraction (XRPD) data for AMG 900 hydrochloride salt (crystalline Form A) is set forth in FIG. 12.

Example 12

Preparation of Hydrochloride Salt Crystalline Form B of AMG 900

To about 43 mg of AMG 900 free base crystalline Form A was added about 4 mL of 0.1N HCl to form a slurry. The slurry was dispersed in a sonic bath and stirred overnight at room temperature. The slurry was filtered to isolate the titled product material.
NMR Data for AMG 900 hydrochloride salt (crystalline Form B)
$^1$H NMR (400 MHz, DMSO-$d_6$) δ ppm 2.11-2.17 (m, 1H) 2.30 (dt, J=3.64, 1.85 Hz, 3H) 3.86 (d, J=13.20 Hz, 1H) 7.15-7.36 (m, 2H) 7.50 (d, J=8.90 Hz, 1H) 8.02-8.08 (m, 1H) 8.20-8.25 (m, 1H)
Melting Point for the Hydrochloride Salt (Form B): Undefined

TABLE 11

AMG 900 Hydrochloride Salt Crystalline Form B XRPD pattern data

| Pos. [°2Th.] | FWHM [°2Th.] | d-spacing [Å] |
|---|---|---|
| 8.49 | 0.10 | 10.41 |
| 8.74 | 0.13 | 10.12 |
| 10.91 | 0.13 | 8.11 |
| 11.36 | 0.16 | 7.79 |
| 12.63 | 0.19 | 7.01 |
| 13.82 | 0.13 | 6.41 |
| 14.52 | 0.26 | 6.10 |
| 15.09 | 0.16 | 5.87 |
| 15.54 | 0.16 | 5.70 |
| 15.88 | 0.13 | 5.58 |
| 17.99 | 0.13 | 4.93 |

TABLE 11-continued

AMG 900 Hydrochloride Salt Crystalline Form B
XRPD pattern data

| Pos. [°2Th.] | FWHM [°2Th.] | d-spacing [Å] |
|---|---|---|
| 18.31 | 0.19 | 4.84 |
| 19.73 | 0.23 | 4.50 |
| 20.59 | 0.19 | 4.31 |
| 21.19 | 0.16 | 4.19 |
| 21.53 | 0.10 | 4.13 |
| 22.06 | 0.19 | 4.03 |
| 23.29 | 0.16 | 3.82 |
| 25.25 | 0.16 | 3.53 |
| 25.90 | 0.19 | 3.44 |
| 26.43 | 0.23 | 3.37 |
| 27.07 | 0.26 | 3.29 |
| 27.72 | 0.19 | 3.22 |
| 28.71 | 0.32 | 3.11 |
| 29.74 | 0.23 | 3.00 |
| 30.19 | 0.13 | 2.96 |
| 31.13 | 0.32 | 2.87 |
| 31.91 | 0.16 | 2.80 |
| 32.39 | 0.23 | 2.76 |
| 33.19 | 0.26 | 2.70 |
| 34.43 | 0.39 | 2.60 |

The X-ray powder diffraction (XRPD) data for AMG 900 hydrochloride salt (Form B) is set forth in FIG. 13.

Example 13

Preparation of Hydrochloride Salt Crystalline Form C of AMG 900

To about 63 mg of AMG 900 free base crystalline Form A in water at pH 1.5 was added 4 mL of 0.1N HCl to form a slurry. The slurry was stirred overnight at room temperature, then filtered to isolate the titled product material.
Melting Point for the Hydrochloride Salt (Form C): Undefined

TABLE 12

AMG 900 Hydrochloride Salt Crystalline Form C
XRPD pattern data

| Pos. [°2Th.] | FWHM [°2Th.] | d-spacing [Å] |
|---|---|---|
| 7.23 | 0.10 | 12.23 |
| 8.17 | 0.10 | 10.82 |
| 9.32 | 0.10 | 9.49 |
| 10.47 | 0.13 | 8.45 |
| 11.51 | 0.10 | 7.69 |
| 12.29 | 0.10 | 7.20 |
| 15.98 | 0.10 | 5.55 |
| 16.36 | 0.10 | 5.42 |
| 16.78 | 0.10 | 5.28 |
| 17.03 | 0.10 | 5.21 |
| 17.77 | 0.10 | 4.99 |
| 18.15 | 0.10 | 4.89 |
| 18.88 | 0.13 | 4.70 |
| 19.47 | 0.13 | 4.56 |
| 20.22 | 0.10 | 4.39 |
| 21.00 | 0.10 | 4.23 |
| 22.73 | 0.19 | 3.91 |
| 23.70 | 0.13 | 3.75 |
| 24.62 | 0.13 | 3.62 |
| 25.31 | 0.13 | 3.52 |
| 25.91 | 0.13 | 3.44 |
| 26.48 | 0.10 | 3.37 |
| 26.75 | 0.10 | 3.33 |
| 26.97 | 0.13 | 3.31 |
| 27.44 | 0.10 | 3.25 |
| 29.03 | 0.10 | 3.08 |
| 31.00 | 0.10 | 2.88 |

TABLE 12-continued

AMG 900 Hydrochloride Salt Crystalline Form C
XRPD pattern data

| Pos. [°2Th.] | FWHM [°2Th.] | d-spacing [Å] |
|---|---|---|
| 31.71 | 0.13 | 2.82 |
| 32.87 | 0.32 | 2.73 |
| 33.31 | 0.13 | 2.69 |
| 33.94 | 0.10 | 2.64 |
| 34.75 | 0.39 | 2.58 |

The X-ray powder diffraction (XRPD) data for AMG 900 hydrochloride salt crystalline Form C is set forth in FIG. 14.

Example 14

Preparation of Hydrochloride Salt Crystalline Form D of AMG 900

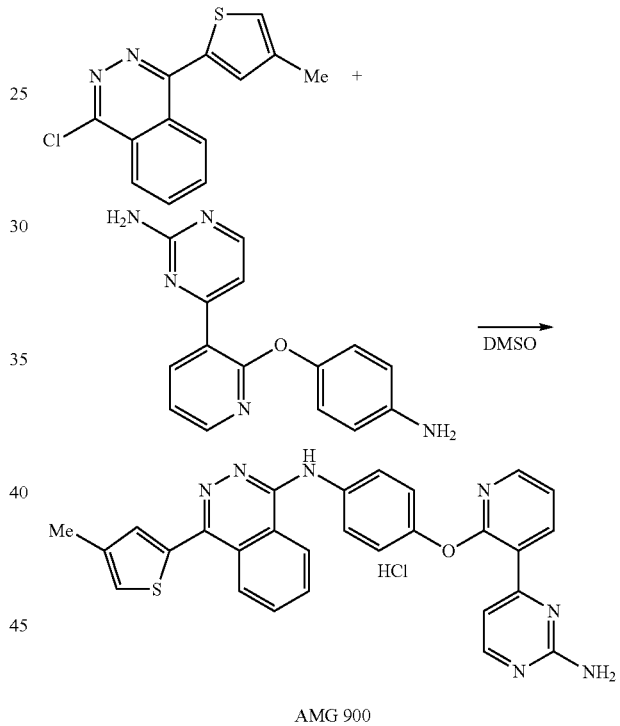

AMG 900

Chlorophthalazine (7.47 grams, 28.6 mmol) and aniline 2 (8.0 grams, 28.6 mmol) were combined in a round bottom flask and to the mixture was added dimethylsulfoxide (86.4 mL). The reaction was purged with nitrogen gas, then heated to 80° C. for 3 hours. The reaction was cooled to 70° C. and water (35 mL) was added to it. Over a period of about 30 minutes, a layer of solid material formed at the bottom of the reaction mixture. The slurry was maintained for 1 hour at 70° C. then cooled to 20° C. and left to stir overnight. The slurry was re-heated to 70° C. and to it was added 29 mL of water, and the reaction was held for 1 hour at 70° C. then cooled to 20° C. and filtered. The filter cake was washed with water then dried on a frit overnight under nitrogen gas. 13.26 grams of a solid state crystalline AMG 900 hydrochloride salt Form D was isolated. The first batch crystalline product was recrystallized by dissolving 12.5 grams in dimethylsulfoxide (19 mL) at 55° C. To this solution was added ethanol (55 mL) to give a thick seedbed of crystalline material at the bottom of the reaction. The mixture was heated to 70° C. and to it was added ethanol (51 mL). The mixture was then cooled to 20° C. and stirred overnight. The resulting solids were filtered and washed with ethanol to give the product, solid state crystalline AMG 900 hydrochloride salt Form D. Some amount of the second batch was again recrystallized by dissolving 10 grams in dimethylsulfoxide (50 mL) at 80° C. then adding water (75 mL) and holding the reaction at 70° C. for 1 hour. The slurry was cooled to 20° C., filtered and the filter cake was washed with water then dried in a vacuum oven to give 8.42 grams of batch C. The recrystallization procedure was again conducted on 6.6 grams of batch C by stirring in dimethylsulfoxide at 20° C. overnight, then filtered to remove solids (crop D).

NMR Data for AMG 900 Hydrochloride Salt Crystalline Form D: $^1$H NMR (400 MHz, DMSO-$d_6$) δ ppm 9.02 (m, 1H), 8.50 (m, 1H), 8.41 (m, 2H), 8.29 (m, 1H), 8.21 (m, 2H), 7.74 (d, 2H), 7.61 (s, 1H), 7.46, (s, 1H), 7.35 (m, 4H), 2.35, (s, 3H).
Melting Point for AMG 900 Hydrochloride Salt Crystalline Form D: Onset about 253° C.

TABLE 13

AMG 900 Hydrochloride Salt (Crystalline Form D) XRPD pattern data

| Pos. [°2Th.] | FWHM [°2Th.] | d-spacing [Å] |
|---|---|---|
| 9.56 | 0.13 | 9.25 |
| 10.26 | 0.13 | 8.62 |
| 11.30 | 0.13 | 7.83 |
| 11.79 | 0.10 | 7.50 |
| 12.31 | 0.13 | 7.19 |
| 12.72 | 0.16 | 6.96 |
| 13.63 | 0.13 | 6.50 |
| 14.00 | 0.13 | 6.32 |
| 15.17 | 0.13 | 5.84 |
| 15.52 | 0.13 | 5.71 |
| 15.93 | 0.13 | 5.56 |
| 17.12 | 0.13 | 5.18 |
| 17.61 | 0.10 | 5.04 |
| 18.25 | 0.13 | 4.86 |
| 18.56 | 0.13 | 4.78 |
| 19.17 | 0.26 | 4.63 |
| 19.93 | 0.16 | 4.45 |
| 20.61 | 0.19 | 4.31 |
| 20.88 | 0.13 | 4.25 |
| 21.56 | 0.13 | 4.12 |
| 21.85 | 0.13 | 4.07 |
| 22.45 | 0.16 | 3.96 |
| 22.99 | 0.10 | 3.87 |
| 23.42 | 0.13 | 3.80 |
| 24.00 | 0.16 | 3.71 |
| 24.48 | 0.13 | 3.64 |
| 24.93 | 0.13 | 3.57 |
| 25.33 | 0.13 | 3.52 |
| 25.61 | 0.10 | 3.48 |
| 25.85 | 0.06 | 3.45 |
| 26.07 | 0.13 | 3.42 |
| 26.50 | 0.16 | 3.36 |
| 27.42 | 0.23 | 3.25 |
| 28.03 | 0.19 | 3.18 |
| 28.52 | 0.06 | 3.13 |
| 28.74 | 0.10 | 3.11 |
| 29.13 | 0.13 | 3.07 |
| 29.42 | 0.13 | 3.04 |
| 29.75 | 0.13 | 3.00 |
| 30.24 | 0.16 | 2.96 |
| 30.72 | 0.13 | 2.91 |
| 30.95 | 0.10 | 2.89 |
| 31.56 | 0.13 | 2.83 |
| 31.82 | 0.13 | 2.81 |
| 32.21 | 0.13 | 2.78 |

TABLE 13-continued

AMG 900 Hydrochloride Salt (Crystalline Form D) XRPD pattern data

| Pos. [°2Th.] | FWHM [°2Th.] | d-spacing [Å] |
|---|---|---|
| 32.75 | 0.19 | 2.73 |
| 33.54 | 0.19 | 2.67 |
| 34.50 | 0.13 | 2.60 |
| 34.80 | 0.13 | 2.58 |

The X-ray powder diffraction (XRPD) data for the AMG 900 hydrochloride salt crystalline Form D is set forth in FIG. 15.

Example 15

Preparation of Hydrochloride Salt Crystalline Form E of AMG 900

About 471.61 mg of AMG 900 free base crystalline Form A was weighed into a 20 mL scintillation vial then charged about 10 mL of 3N methanolic HCl and with a teflon coated stir bar. The vial was capped and the mixture was stirred at 50° C., covered with foil and then stirred over the weekend. Most of the solvent evaporated over the weekend leaving a moist pale brown solid. The solids were left to evaporate to dryness in the hood.

Melting Point for the Hydrochloride Salt (Form E): Undefined

TABLE 14

AMG 900 Hydrochloride Salt Crystalline Form E XRPD pattern data

| Pos. [°2Th.] | FWHM [°2Th.] | d-spacing [Å] |
|---|---|---|
| 8.35 | 0.16 | 10.59 |
| 12.52 | 0.10 | 7.07 |
| 14.21 | 0.10 | 6.23 |
| 14.51 | 0.13 | 6.10 |
| 15.07 | 0.19 | 5.88 |
| 16.36 | 0.10 | 5.42 |
| 17.05 | 0.10 | 5.20 |
| 17.95 | 0.13 | 4.94 |
| 18.30 | 0.10 | 4.85 |
| 18.48 | 0.13 | 4.80 |
| 19.61 | 0.13 | 4.53 |
| 19.97 | 0.10 | 4.45 |
| 20.27 | 0.13 | 4.38 |
| 20.70 | 0.13 | 4.29 |
| 22.26 | 0.13 | 3.99 |
| 22.68 | 0.13 | 3.92 |
| 23.32 | 0.19 | 3.82 |
| 24.74 | 0.13 | 3.60 |
| 25.64 | 0.10 | 3.47 |
| 25.87 | 0.13 | 3.44 |
| 26.33 | 0.13 | 3.39 |
| 26.86 | 0.10 | 3.32 |
| 27.68 | 0.13 | 3.22 |
| 28.19 | 0.10 | 3.17 |
| 28.60 | 0.10 | 3.12 |
| 29.21 | 0.19 | 3.06 |
| 29.85 | 0.16 | 2.99 |
| 30.88 | 0.13 | 2.90 |
| 31.13 | 0.10 | 2.87 |
| 31.45 | 0.16 | 2.84 |
| 32.00 | 0.26 | 2.80 |
| 32.60 | 0.16 | 2.75 |
| 33.60 | 0.13 | 2.67 |
| 34.34 | 0.16 | 2.61 |
| 34.75 | 0.13 | 2.58 |

Figure 16:
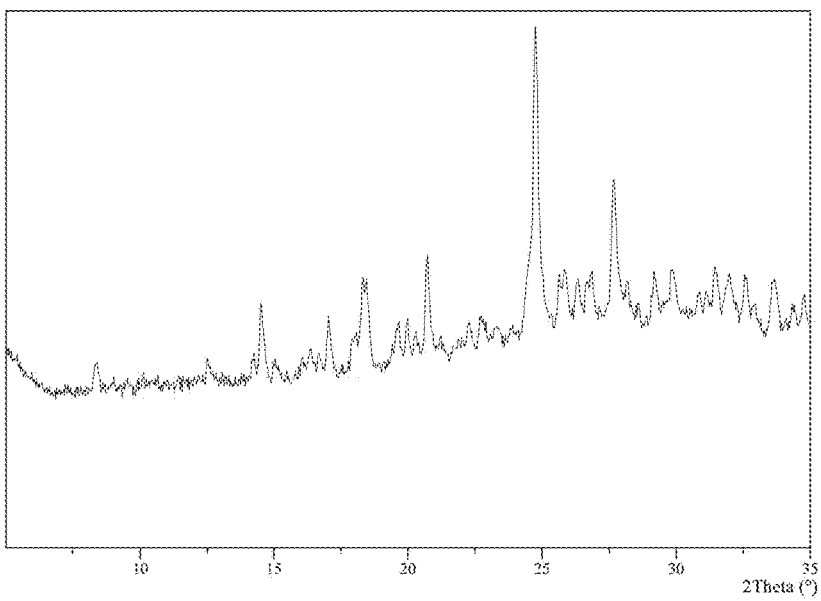
FIG. 16 is a graph depicting the X-ray powder diffraction (XRPD) pattern for the hydrochloride salt (crystalline Form E) of AMG 900.

The X-ray powder diffraction (XRPD) data for the AMG 900 hydrochloride salt crystalline Form E is set forth in FIG. 16.

Example 16

Preparation of Besylate (Benzenesulfonate) Salt Crystalline Form A of AMG 900

To a slurry of AMG 900 (0.5 grams) in N,N-dimethylformamide (1.5 mL, 0.99 mmol) was added benzenesulfonic acid (0.16 grams, 0.99 mmol) to give a homogeneous solution. Tert-butyl methyl ether (1.5 mL) was added to the mixture and it was heated to 70° C. More tert-butyl methyl ether (4.5 mL) was added to the heated mixture to give a slurry. The slurry was cooled to 20° C., then filtered and the fi9lter cake was washed with tert-butyl methyl ether. The resulting solids were dried under a stream of nitrogen gas overnight to give AMG 900 besylate (benzenesulfonate) salt crystalline Form A. NMR Data for the AMG 900 Besylate (Benzenesulfonate) Salt Crystalline Form A:

$^1$H NMR (400 MHz, DMSO-$d_6$) δ ppm 8.85 (m, 1H), 8.53 (m, 1H), 8.41 (m, 2H) 8.41 (m, 2H), 8.30 (dd, 1H), 8.25 (m, 2H), 7.72 (m, 2H), 7.63 (d, 1H), 7.60 (m, 2H), 7.49 (m, 1H), 7.38 (m 4H), 7.31 (m, 4H), 2.35 (s, 3H).
Melting Point for the Besylate Salt (Form A): Undefined

TABLE 15

AMG 900 Besylate (Benzenesulfonate) Salt Crystalline Form A XRPD pattern data

| Pos. [°2Th.] | FWHM [°2Th.] | d-spacing [Å] |
| --- | --- | --- |
| 7.16 | 0.13 | 12.35 |
| 7.98 | 0.19 | 11.09 |
| 8.65 | 0.19 | 10.23 |
| 9.87 | 0.19 | 8.96 |
| 11.55 | 0.13 | 7.66 |
| 12.23 | 0.16 | 7.24 |
| 13.20 | 0.23 | 6.71 |
| 13.89 | 0.10 | 6.38 |
| 15.74 | 0.13 | 5.63 |
| 16.48 | 0.26 | 5.38 |
| 17.21 | 0.23 | 5.15 |
| 17.83 | 0.13 | 4.98 |
| 19.26 | 0.10 | 4.61 |
| 19.69 | 0.19 | 4.51 |
| 20.17 | 0.16 | 4.40 |
| 21.52 | 0.13 | 4.13 |
| 23.22 | 0.16 | 3.83 |
| 24.65 | 0.19 | 3.61 |
| 25.19 | 0.10 | 3.54 |
| 26.03 | 0.39 | 3.42 |
| 27.29 | 0.19 | 3.27 |

The X-ray powder diffraction (XRPD) data for the AMG 900 besylate (benzenesulfonate) salt crystalline Form A is set forth in FIG. 17.

Example 17

Preparation of Tosylate (Toluenesulfonate) Salt Crystalline Form A of AMG 900

To a solution of AMG 900 free base crystalline Form A (1.1 grams, 2.18 mmol) in N,N-dimethylformamide (5.5 mL) was added toluenesulfonic acid monohydrate (0.42 grams, 2.18 mmol). To the mixture was added tert-butyl methyl ether (12 mL) and N,N-dimethylformamide (0.5 mL), and the resulting slurry was stirred overnight at 20° C. The mixture was filtered and the filter cake was washed with tert-butyl methyl ether. The resulting solids were dried under nitrogen gas to provide 1.1 grams of AMG 900 tosylate salt crystalline Form A.

NMR Data for AMG 900 Tosylate Salt Crystalline Form A: $^1$H NMR (400 MHz, DMSO-$d_6$) δ ppm 8.83 (m, 1H), 8.50 (m, 1H), 8.40 (m, 2H), 8.29 (dd, 1H), 8.23 (m, 2H), 7.73 (m, 2H), 7.62 (m, 1H), 7.48 (m, 3H), 7.36 (m, 4H), 7.10 (m, 2H), 2.35 (m, 3H), 2.28 (s, 3H).

Melting Point for the AMG 900 Tosylate Salt (Form A): Undefined

TABLE 16

AMG 900 Tosylate (Toluenesulfonate) Salt Crystalline Form A XRPD pattern data

| Pos. [°2Th.] | FWHM [°2Th.] | d-spacing [Å] |
| --- | --- | --- |
| 6.26 | 0.16 | 14.13 |
| 8.60 | 0.13 | 10.28 |
| 10.10 | 0.13 | 8.76 |
| 11.35 | 0.13 | 7.80 |
| 12.49 | 0.16 | 7.09 |
| 12.96 | 0.10 | 6.83 |
| 13.51 | 0.16 | 6.55 |
| 14.19 | 0.19 | 6.24 |
| 14.64 | 0.10 | 6.05 |
| 14.98 | 0.13 | 5.92 |
| 15.62 | 0.13 | 5.67 |
| 16.19 | 0.13 | 5.47 |
| 16.60 | 0.06 | 5.34 |
| 16.83 | 0.13 | 5.27 |
| 17.25 | 0.13 | 5.14 |
| 18.05 | 0.13 | 4.92 |
| 18.85 | 0.13 | 4.71 |
| 19.11 | 0.10 | 4.64 |
| 19.60 | 0.16 | 4.53 |
| 20.36 | 0.13 | 4.36 |
| 20.87 | 0.10 | 4.26 |
| 21.30 | 0.16 | 4.17 |
| 21.67 | 0.13 | 4.10 |
| 22.38 | 0.16 | 3.97 |
| 22.78 | 0.16 | 3.90 |
| 23.23 | 0.13 | 3.83 |
| 24.03 | 0.13 | 3.70 |
| 24.57 | 0.10 | 3.62 |
| 24.85 | 0.13 | 3.58 |
| 25.16 | 0.10 | 3.54 |
| 25.74 | 0.13 | 3.46 |
| 26.29 | 0.13 | 3.39 |
| 27.06 | 0.13 | 3.29 |
| 27.65 | 0.16 | 3.23 |
| 29.13 | 0.16 | 3.07 |
| 29.68 | 0.13 | 3.01 |
| 30.26 | 0.10 | 2.95 |
| 30.55 | 0.13 | 2.93 |
| 31.35 | 0.16 | 2.85 |
| 31.73 | 0.13 | 2.82 |
| 33.47 | 0.13 | 2.68 |
| 33.91 | 0.13 | 2.64 |
| 34.44 | 0.19 | 2.60 |

The X-ray powder diffraction (XRPD) data for AMG 900 tosylate salt crystalline Form A is set forth in FIG. 18.

Example 18

Preparation of Acetate Salt Crystalline Form A of AMG 900

AMG 900 free base crystalline Form A (0.66 grams) was added to acetic acid (1.7 mL) and the mixture was heated to about 80° C. to give a homogeneous solution. The solution was cooled to 20° C. to give a slurry, to which 2-propanol (1.5 mL) was added to give a thick slurry. The slurry was heated to about 80° C. and the remaining 2-propanol (3.4 mL) was added over about 1 hour. The mixture was cooled to about 20° C. and allowed to stir overnight. The product was isolated by filtration and the filter cake was washed with 2-propanol then dried under nitrogen gas to afford AMG 900 acetate salt crystalline Form A.

NMR Data for crystalline AMG 900 Acetate Salt Crystalline Form A: $^1$H NMR (400 MHz, DMSO-$d_6$) δ ppm 11.97 (bs, 1H), 9.36 (bs, 1H), 8.66 (d, 1H), 8.39 (m, 3H), 8.23 (dd, 1H), 8.04 (m, 2H), 7.94 (d, 2H), 7.51 (s, 1H), 7.28 (m, 3H), 7.19 (d, 2H), 6.75 (bs, 2H), 2.33 (s, 3H), 1.91 (s, 3H).
Melting Point for the Acetate Salt (Form A): Undefined

TABLE 17

AMG 900 Acetate Salt Crystalline Form A XRPD pattern data

| Pos. [°2Th.] | FWHM [°2Th.] | d-spacing [Å] |
|---|---|---|
| 7.39 | 0.13 | 11.96 |
| 9.35 | 0.16 | 9.45 |
| 11.47 | 0.16 | 7.71 |
| 12.03 | 0.10 | 7.35 |
| 13.42 | 0.19 | 6.60 |
| 14.39 | 0.13 | 6.16 |
| 15.80 | 0.10 | 5.61 |
| 16.69 | 0.19 | 5.31 |
| 17.61 | 0.16 | 5.04 |
| 18.51 | 0.16 | 4.79 |
| 18.98 | 0.16 | 4.67 |
| 21.08 | 0.23 | 4.21 |
| 21.73 | 0.19 | 4.09 |
| 23.00 | 0.16 | 3.87 |
| 23.31 | 0.13 | 3.82 |
| 24.40 | 0.10 | 3.65 |
| 25.24 | 0.13 | 3.53 |
| 26.60 | 0.19 | 3.35 |
| 27.73 | 0.19 | 3.22 |
| 29.76 | 0.26 | 3.00 |
| 30.55 | 0.10 | 2.93 |
| 31.53 | 0.39 | 2.84 |
| 34.79 | 0.16 | 2.58 |

The X-ray powder diffraction (XRPD) data for the AMG 900 acetate salt crystalline Form A is set forth in FIG. 19.

Example 19

Preparation of Sulfate Salt Crystalline Form A of AMG 900

A solution of 200 mg H$_2$SO$_4$ diluted to 10 mL with DMSO was prepared. About 1 mL of the H$_2$SO$_4$-DMSO solution (approx 20 mg) was added to a vial charged with 100 mg AMG 900. The mixture became a solution. 2 mL of 2-propanol was added to the solution. 0.2 additional mL of 2-propanol was added to the solution and the solution became cloudy. The cloudy solution was sonicated until crystalline materials began to precipitate. The mixture was heated to redissolve the precipitated solids, then maintained at about 60° C. in an oil bath. Solids began to crash out of solution after about 15 minutes. The mixture was continuously heated at 60° C. in the oil bath for about 3 hours, then it was cooled to RT. The mixture was centrifuged to obtain the titled solid state product. The supernatant was assayed and found to contain about 5 mg/ml the AMG 900 salt. The rest of the salt slurry was filtered on a medium glass frit to give 69 mg of the titled product as a yellow solid.

NMR Data for AMG 900 Sulfate Salt crystalline Form A: $^1$H NMR (400 MHz, DMSO-$d_6$) δ ppm 8.84 (m, 1H), 8.51 (m, 1H), 8.40 (m, 2H), 8.29 (dd, 1H), 8.24 (m, 2H), 7.73 (d, 2H), 7.62 (d, 1H), 7.47 (s, 1H), 7.36 (m, 4H), 2.35 (s, 3H). (residual solvents not reported)
Melting Point for the Sulfate Salt (Form A): Undefined

TABLE 18

AMG 900 Sulfate Salt Crystalline Form A XRPD pattern data

| Pos. [°2Th.] | FWHM [°2Th.] | d-spacing [Å] |
|---|---|---|
| 8.19 | 0.16 | 10.80 |
| 8.70 | 0.19 | 10.16 |
| 9.39 | 0.16 | 9.42 |
| 10.91 | 0.19 | 8.11 |
| 12.24 | 0.16 | 7.23 |
| 13.99 | 0.16 | 6.33 |
| 14.72 | 0.13 | 6.02 |
| 15.31 | 0.16 | 5.79 |
| 16.05 | 0.13 | 5.52 |
| 16.33 | 0.13 | 5.43 |
| 16.85 | 0.19 | 5.26 |
| 17.37 | 0.19 | 5.11 |
| 18.70 | 0.23 | 4.75 |
| 19.10 | 0.16 | 4.65 |
| 19.55 | 0.13 | 4.54 |
| 20.21 | 0.19 | 4.39 |
| 20.67 | 0.13 | 4.30 |
| 21.03 | 0.10 | 4.22 |
| 21.53 | 0.13 | 4.13 |
| 21.78 | 0.13 | 4.08 |
| 22.48 | 0.13 | 3.95 |
| 22.84 | 0.16 | 3.89 |
| 23.84 | 0.19 | 3.73 |
| 24.57 | 0.16 | 3.62 |
| 24.97 | 0.19 | 3.57 |
| 25.66 | 0.16 | 3.47 |
| 26.06 | 0.19 | 3.42 |
| 26.78 | 0.19 | 3.33 |
| 27.10 | 0.13 | 3.29 |
| 27.42 | 0.10 | 3.25 |
| 28.02 | 0.13 | 3.18 |
| 28.36 | 0.16 | 3.15 |
| 28.96 | 0.16 | 3.08 |
| 29.44 | 0.16 | 3.03 |
| 30.51 | 0.29 | 2.93 |
| 31.93 | 0.16 | 2.80 |
| 32.43 | 0.13 | 2.76 |
| 33.28 | 0.16 | 2.69 |
| 34.16 | 0.26 | 2.62 |

The X-ray powder diffraction (XRPD) data for the AMG 900 sulfate salt crystalline Form A is set forth in FIG. 20.

Example 20

Preparation of Sulfate Salt Crystalline Form B of AMG 900

To a 25 ml RB flask was added 250 mg AMG 900 then 2.4 mL of the H$_2$SO$_4$-DMSO solution (~20 mg of H$_2$SO$_4$/mL solution; see example 19). The mixture became a solution. An additional 2.4 mL of 2-propanol was added to the solution and it was then seeded with. Sulfate salt crystalline Form B material (where seed material is not available, a small aliquot was removed from the crystallization solution and sonicated. The aliquot spontaneously crystallized to provide sulfate salt crystalline Form B material, which can be used as the seed material referred to herein). The resulting mixture became a slurry, which was briefly sonicated. An additional 2.4 mL of 2-propanol was slowly added over 2 hours via syringe pump. A very small crystalline material precipitated from the mixture. The mixture was heated in an 80° C. oil bath beginning for about 50 minutes and allowed to cool slowly in bath. The mixture was stirred at room temperature overnight, the resulting solids were slowly filtered and washed with 2-propanol. The filter cake was dried on a frit over nitrogen gas to provide 0.273 grams of the titled product (crop A). 100 mg of AMG 900 sulfate salt crop A was charged into a vial. Added 1.0 mL ethanol (200 proof) to the vial and the vial was heated at 60° C. in an oil bath for about 2 hrs. An aliquot of the reaction was centrifuged to give solid the titled product, which is characterized below.

NMR Data for the AMG 900 Sulfate Salt Crystalline Form B: $^1$H NMR (400 MHz, DMSO-$d_6$) δ ppm 8.84 (m, 1H), 8.51 (m, 1H), 8.41 (m, 2H), 8.30 (dd, 1H), 8.23 (m, 2H), 7.74 (m, 2H), 7.61 (d, 1H), 7.47 (m, 1H), 7.37 (m, 4H), 2.35 (d, 3H), (residual solvents peaks not reported).
Melting Point for the Sulfate Salt (Form B): Undefined

TABLE 19

AMG 900 Sulfate Salt Crystalline Form B XRPD pattern data

| Pos. [°2Th.] | FWHM [°2Th.] | d-spacing [Å] |
|---|---|---|
| 8.16 | 0.32 | 10.84 |
| 8.82 | 0.19 | 10.02 |
| 9.40 | 0.13 | 9.41 |
| 10.80 | 0.19 | 8.19 |
| 11.32 | 0.13 | 7.82 |
| 11.92 | 0.19 | 7.42 |
| 12.60 | 0.19 | 7.03 |
| 13.56 | 0.10 | 6.53 |
| 13.97 | 0.16 | 6.34 |
| 14.72 | 0.19 | 6.02 |
| 15.32 | 0.16 | 5.78 |
| 16.21 | 0.16 | 5.47 |
| 17.09 | 0.13 | 5.19 |
| 17.26 | 0.16 | 5.14 |
| 17.66 | 0.13 | 5.02 |
| 18.62 | 0.13 | 4.77 |
| 19.29 | 0.16 | 4.60 |
| 19.58 | 0.13 | 4.53 |
| 20.01 | 0.10 | 4.44 |
| 20.24 | 0.10 | 4.39 |
| 20.60 | 0.16 | 4.31 |
| 21.01 | 0.16 | 4.23 |
| 22.31 | 0.16 | 3.99 |
| 22.72 | 0.13 | 3.91 |
| 23.41 | 0.13 | 3.80 |
| 23.85 | 0.19 | 3.73 |
| 24.56 | 0.16 | 3.63 |
| 25.30 | 0.19 | 3.52 |
| 26.03 | 0.16 | 3.42 |
| 26.58 | 0.19 | 3.35 |
| 27.49 | 0.19 | 3.24 |
| 28.65 | 0.19 | 3.12 |
| 29.63 | 0.19 | 3.02 |

The X-ray powder diffraction (XRPD) data for the AMG 900 sulfate salt crystalline Form B is set forth in FIG. 21.

Example 21

Preparation of Sulfate Salt Crystalline Form C of AMG 900

250 mg of AMG 900 was charged into a single neck RB flask, to which 2.0 mL AcOH was added to give a homogeneous solution. The reaction solution was immersed in a 60° C. oil bath. A separate solution was prepared by diluting 50 mg $H_2SO_4$ in 2 mL of AcOH. The $H_2SO_4$—AcOH solution was added to the heated reaction solution of AMG 900 freebase in AcOH. As last of the acid solution was added a heavy precipitate formed in the reaction mixture. The reaction was heated at an oil bath temperature of about 100° C. The reaction slurry remained thick. An additional 1 mL of AcOH was added and the reaction was maintained in the 100° C. oil bath for about 30 minutes, then allowed to cool to RT. After a couple of hours, the mixture was filtered and the filter cake was dried on a frit under a stream of nitrogen gas, to provide to the titled compound as a tan solid. The supernatant was assayed and found to contain the AMG 900 salt at about 19 mg/mL. NMR Data for the Sulfate Salt Crystalline Form C: $^1$H NMR (400 MHz, DMSO-$d_6$) δ ppm 8.87 (m, 1H), 8.53 (m, 1H), 8.42 (m, 2H), 8.32 (dd, 1H), 8.27 (m, 2H), 7.70 (m, 2H), 7.63 (d, 1H), 7.50 (m, 1H), 7.44 (d, 1H), 7.38 (m, 3H), 2.36 (d, 3H), (residual solvent not reported).
Melting Point for the Sulfate Salt (Form C): Undefined

TABLE 20

AMG 900 Sulfate Salt Crystalline Form C XRPD pattern data

| Pos. [°2Th.] | FWHM [°2Th.] | d-spacing [Å] |
|---|---|---|
| 6.53 | 0.19 | 13.54 |
| 7.43 | 0.10 | 11.90 |
| 8.81 | 0.16 | 10.03 |
| 10.78 | 0.32 | 8.21 |
| 13.03 | 0.19 | 6.79 |
| 13.97 | 0.19 | 6.34 |
| 14.22 | 0.19 | 6.23 |
| 15.27 | 0.19 | 5.80 |
| 16.17 | 0.16 | 5.48 |
| 17.27 | 0.10 | 5.14 |
| 17.46 | 0.32 | 5.08 |
| 18.49 | 0.32 | 4.80 |
| 19.06 | 0.19 | 4.66 |
| 20.58 | 0.23 | 4.32 |
| 21.56 | 0.32 | 4.12 |
| 22.27 | 0.29 | 3.99 |
| 23.65 | 0.16 | 3.76 |
| 23.97 | 0.19 | 3.71 |
| 25.43 | 0.19 | 3.50 |
| 25.63 | 0.10 | 3.48 |
| 25.93 | 0.19 | 3.44 |
| 26.54 | 0.29 | 3.36 |
| 27.25 | 0.19 | 3.27 |
| 28.18 | 0.45 | 3.17 |
| 29.44 | 0.19 | 3.03 |

The X-ray powder diffraction (XRPD) data for the Sulfate Salt crystalline Form C is set forth in FIG. 22.

Example 22

Preparation of Sulfate Salt Crystalline Form D of AMG 900

The AMG 900 sulfate salt crystalline from A converted to AMG 900 sulfate salt crystalline Form D after being left for about 24 hrs at room temperature.
Melting Point for the Sulfate Salt (Form D): Undefined

TABLE 21

AMG 900 Sulfate Salt Crystalline Form D XRPD pattern data

| Pos. [°2Th.] | FWHM [°2Th.] | d-spacing [Å] |
|---|---|---|
| 7.35 | 0.39 | 12.03 |
| 8.31 | 0.13 | 10.64 |
| 10.98 | 0.23 | 8.06 |
| 11.97 | 0.16 | 7.39 |
| 12.42 | 0.19 | 7.13 |
| 14.05 | 0.19 | 6.31 |
| 15.13 | 0.23 | 5.85 |
| 17.40 | 0.13 | 5.10 |
| 18.90 | 0.26 | 4.69 |
| 19.57 | 0.13 | 4.54 |

TABLE 21-continued

AMG 900 Sulfate Salt Crystalline Form D XRPD pattern data

| Pos. [°2Th.] | FWHM [°2Th.] | d-spacing [Å] |
|---|---|---|
| 20.37 | 0.19 | 4.36 |
| 21.09 | 0.13 | 4.21 |
| 21.94 | 0.23 | 4.05 |
| 23.13 | 0.19 | 3.85 |
| 23.79 | 0.13 | 3.74 |
| 23.93 | 0.13 | 3.72 |
| 24.52 | 0.13 | 3.63 |
| 25.03 | 0.19 | 3.56 |
| 25.74 | 0.19 | 3.46 |
| 26.86 | 0.23 | 3.32 |
| 27.53 | 0.29 | 3.24 |
| 29.49 | 0.16 | 3.03 |

The X-ray powder diffraction (XRPD) data for the sulfate salt crystalline Form D is set forth in FIG. 23.

Example 23

Preparation of Sulfate Salt Crystalline Form E of AMG 900

The title AMG 900 sulfate salt crystalline Form E was prepared by heating sulfate salt crystalline Form C to about 127° C. at which temperature it desolvated, and then was allowed to cool to room temperature and afforded the titled crystalline form E.
Melting Point for the Sulfate Salt (Form E): Undefined

TABLE 22

AMG 900 Sulfate Salt Crystalline Form E XRPD pattern data

| Pos. [°2Th.] | FWHM [°2Th.] | d-spacing [Å] |
|---|---|---|
| 7.99 | 0.16 | 11.06 |
| 9.89 | 0.13 | 8.94 |
| 11.15 | 0.19 | 7.94 |
| 12.60 | 0.13 | 7.03 |
| 13.79 | 0.10 | 6.42 |
| 14.27 | 0.16 | 6.21 |
| 14.80 | 0.19 | 5.98 |
| 16.01 | 0.26 | 5.54 |
| 16.78 | 0.32 | 5.28 |
| 18.96 | 0.16 | 4.68 |
| 19.94 | 0.16 | 4.45 |
| 21.13 | 0.16 | 4.20 |
| 22.27 | 0.23 | 3.99 |
| 23.22 | 0.19 | 3.83 |
| 23.76 | 0.16 | 3.75 |
| 24.48 | 0.26 | 3.64 |
| 25.18 | 0.19 | 3.54 |
| 25.54 | 0.13 | 3.49 |
| 26.33 | 0.23 | 3.39 |

The X-ray powder diffraction (XRPD) data for the AMG 900 sulfate salt crystalline Form E is set forth in FIG. 24.

Example 24

Preparation of Fumarate Salt Crystalline Form A of AMG 900

To a mixture of 4.8 mg fumaric acid and 10.00 mg of AMG 900 free base crystalline Form A was added 1 mL EtOAc, and the resulting mixture was dispersed by a sonic bath to form a slurry. The slurry was then stirred at 50° C. for about 24 hr. The titled product solids were isolated by filtering the slurry and drying the filtered solids.

NMR Data for AMG 900 Fumarate Salt crystalline Form A
$^1$H NMR (400 MHz, DMSO-$d_6$) δ ppm 2.35 (d, J=0.88 Hz, 3H) 6.63 (s, 1H), 6.72 (s, 2H) 7.17-7.23 (m(para), 2H) 7.27-7.35 (m, 3H) 7.52 (d, J=0.98 Hz, 1H) 7.92-7.99 (m(para), J=8.90 Hz, 2H) 8.05 (td, J=7.63, 1.27 Hz, 2H) 8.24 (dd, J=4.79, 2.05 Hz, 1H) 8.34-8.46 (m, 3H) 8.65-8.70 (m, 1H) 9.35 (s, 1H) 13.10 (br. s., 1H)
Melting Point for AMG 900 Fumarate Salt Crystalline Form A: Onset about 211-213° C.

TABLE 23

AMG 900 Fumarate Salt Crystalline Form A XRPD pattern data

| Pos. [°2Th.] | FWHM [°2Th.] | d-spacing [Å] |
|---|---|---|
| 6.95 | 0.16 | 12.72 |
| 7.33 | 0.16 | 12.06 |
| 7.65 | 0.16 | 11.55 |
| 8.70 | 0.23 | 10.17 |
| 9.91 | 0.13 | 8.92 |
| 11.29 | 0.16 | 7.84 |
| 12.87 | 0.19 | 6.88 |
| 13.50 | 0.16 | 6.56 |
| 13.86 | 0.16 | 6.39 |
| 14.47 | 0.10 | 6.12 |
| 14.62 | 0.13 | 6.06 |
| 16.12 | 0.23 | 5.50 |
| 17.32 | 0.23 | 5.12 |
| 17.80 | 0.23 | 4.98 |
| 18.54 | 0.23 | 4.79 |
| 19.90 | 0.19 | 4.46 |
| 20.44 | 0.16 | 4.34 |
| 21.37 | 0.19 | 4.16 |
| 22.02 | 0.23 | 4.04 |
| 22.76 | 0.16 | 3.91 |
| 23.60 | 0.16 | 3.77 |
| 24.09 | 0.23 | 3.69 |
| 24.69 | 0.16 | 3.61 |
| 25.14 | 0.26 | 3.54 |
| 25.71 | 0.26 | 3.47 |
| 26.04 | 0.13 | 3.42 |
| 26.87 | 0.10 | 3.32 |
| 27.57 | 0.13 | 3.24 |
| 28.25 | 0.23 | 3.16 |
| 28.80 | 0.16 | 3.10 |
| 29.12 | 0.19 | 3.07 |
| 29.50 | 0.26 | 3.03 |
| 30.31 | 0.32 | 2.95 |
| 31.48 | 0.26 | 2.84 |
| 32.10 | 0.19 | 2.79 |
| 34.37 | 0.32 | 2.61 |

The X-ray powder diffraction (XRPD) data for the AMG 900 fumarate salt crystalline Form A is set forth in FIG. 25.

Example 25

Preparation of Maleate Salt Crystalline Form A of AMG 900

To 6.68 mg of maleic acid (EM Science) and 10.00 mg of AMG 900 free base crystalline Form A was added 1 mL EtOAc. The resulting mixture was dispersed by sonic bath for about 1 hr, resulting in a slurried material. The slurry was filtered and the solids were air dried to afford the titled product as the maleate salt partially crystalline Form A material. The maleate salt did not produce a completely crystalline material under the conditions employed in the present invention.
NMR Data for the AMG 900 Maleate Salt partially crystalline Form A
$^1$H NMR (400 MHz, DMSO-$d_6$) δ ppm 2.35 (d, J=0.68 Hz, 3H) 6.23 (s, 1H) 6.77 (br. s., 1H) 7.20-7.25 (m, 1H)

7.29-7.36 (m, 2H) 7.54 (d, J=1.17 Hz, 1H) 7.90 (d, J=8.80 Hz, 1H) 8.05-8.13 (m, 1H) 8.25 (dd, J=4.79, 1.96 Hz, 1H) 8.35-8.47 (m, 2H) 8.70 (d, J=7.24 Hz, 1H)

Melting Point for the Maleate Salt (Partial Crystal Form A): Undefined

TABLE 24

AMG 900 Maleate Salt partially Crystalline Form A XRPD pattern data

| Pos. [°2Th.] | FWHM [°2Th.] | d-spacing [Å] |
|---|---|---|
| 6.09 | 0.26 | 14.50 |
| 7.33 | 0.19 | 12.05 |
| 8.19 | 0.23 | 10.79 |
| 9.10 | 0.19 | 9.72 |
| 9.44 | 0.78 | 9.37 |
| 12.26 | 0.19 | 7.22 |
| 13.43 | 0.52 | 6.59 |
| 14.94 | 0.52 | 5.93 |
| 16.39 | 0.13 | 5.41 |
| 17.87 | 0.39 | 4.96 |
| 18.60 | 0.39 | 4.77 |
| 19.45 | 0.39 | 4.56 |
| 24.33 | 0.32 | 3.66 |
| 26.09 | 0.78 | 3.42 |

Figure 26:
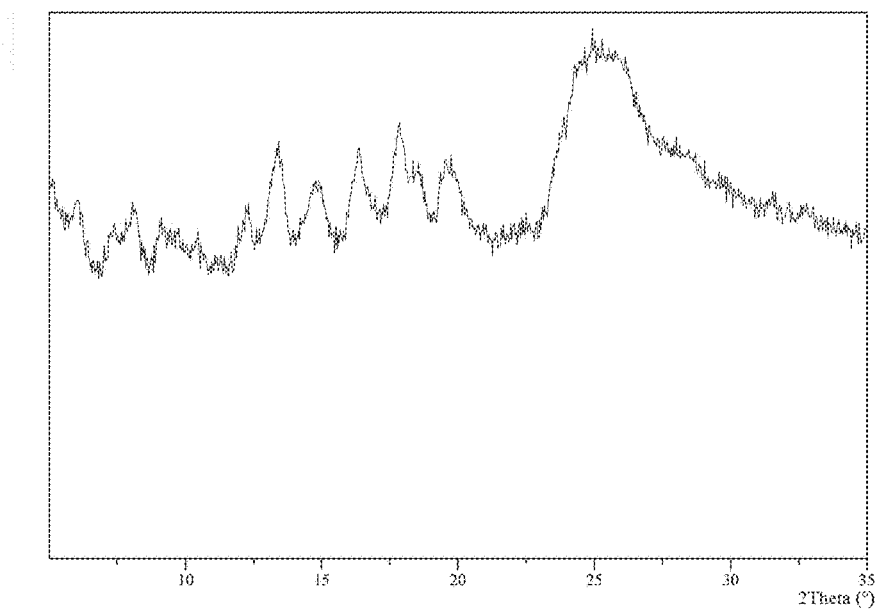
FIG. 26 is a graph depicting the X-ray powder diffraction (XRPD) pattern for the maleate salt partially crystalline Form A of AMG 900.

The X-ray powder diffraction (XRPD) data for the AMG 900 maleate salt crystalline Form A is set forth in FIG. 26.

Example 26

Preparation of Mono-Urea Salt Crystalline Form A of AMG 900

To a mixture of 2.31 mg of urea (Fluka) and 10.00 mg of AMG 900 free base crystalline Form A was added 1 mL EtOAc. The resulting mixture was sonicated for about 1 hr to form a slurry. The slurry was then stirred at 50° C. for about 24 hr, then filtered to afford the titled product material.

NMR Data for the AMG 900 Monourea Salt Crystalline Form A: $^1$H NMR (400 MHz, DMSO-$d_6$) δ ppm 2.35 (d, J=0.78 Hz, 3H) 7.16-7.23 (m, 2H) 7.26-7.35 (m, 3H) 7.52 (d, J=1.08 Hz, 1H) 7.91-7.99 (m, 2H) 8.05 (quind, J=7.35, 1.42 Hz, 2H) 8.24 (dd, J=4.79, 2.05 Hz, 1H) 8.35 (s, 1H) 8.39 (dd, J=7.53, 1.96 Hz, 1H) 8.41-8.46 (m, 1H) 8.61-8.74 (m, 1H) 9.35 (s, 1H)

Melting Point for the AMG 900 Monourea Salt Crystalline Form A: Onset about 204° C.

TABLE 25

AMG 900 Mono-Urea Salt Crystalline Form A XRPD pattern data

| Pos. [°2Th.] | FWHM [°2Th.] | d-spacing [Å] |
|---|---|---|
| 5.34 | 0.16 | 16.56 |
| 10.16 | 0.13 | 8.71 |
| 10.66 | 0.19 | 8.30 |
| 11.33 | 0.16 | 7.81 |
| 12.06 | 0.16 | 7.34 |
| 12.62 | 0.23 | 7.01 |
| 13.71 | 0.16 | 6.46 |
| 14.04 | 0.10 | 6.31 |
| 15.69 | 0.10 | 5.65 |
| 16.14 | 0.13 | 5.49 |
| 17.79 | 0.52 | 4.98 |
| 19.16 | 0.16 | 4.63 |
| 19.50 | 0.13 | 4.55 |
| 20.00 | 0.13 | 4.44 |
| 21.00 | 0.16 | 4.23 |
| 21.33 | 0.10 | 4.17 |
| 21.78 | 0.19 | 4.08 |
| 22.49 | 0.13 | 3.95 |

TABLE 25-continued

AMG 900 Mono-Urea Salt Crystalline Form A XRPD pattern data

| Pos. [°2Th.] | FWHM [°2Th.] | d-spacing [Å] |
|---|---|---|
| 22.83 | 0.16 | 3.89 |
| 23.22 | 0.13 | 3.83 |
| 23.93 | 0.13 | 3.72 |
| 24.25 | 0.16 | 3.67 |
| 25.41 | 0.16 | 3.51 |
| 26.67 | 0.16 | 3.34 |
| 27.17 | 0.13 | 3.28 |
| 27.62 | 0.16 | 3.23 |
| 28.04 | 0.19 | 3.18 |
| 28.26 | 0.13 | 3.16 |
| 29.12 | 0.23 | 3.07 |
| 29.66 | 0.13 | 3.01 |
| 29.90 | 0.13 | 2.99 |
| 30.23 | 0.10 | 2.96 |
| 31.12 | 0.16 | 2.87 |
| 31.63 | 0.16 | 2.83 |
| 32.08 | 0.13 | 2.79 |
| 32.76 | 0.13 | 2.73 |
| 33.68 | 0.23 | 2.66 |
| 34.47 | 0.23 | 2.60 |

The X-ray powder diffraction (XRPD) data for the Monourea Salt (Form A) is set forth in FIG. 27.

Example 27

Preparation of DiUrea Salt Crystalline Form A of AMG 900

To a mixture of 26.4 mg urea (Fluka) and 100.00 mg AMG 900 free base crystalline Form A was added 10 mL EtOAc. The resulting mixture was sonicated for about 2 minutes, upon which a slurry formed. The slurry was stirred at 50° C. for about 24 hr, and filtered to afford the titled compound.

NMR Data for AMG 900 Diurea Salt Crystalline Form A: $^1$H NMR (400 MHz, DMSO-$d_6$) δ ppm 2.35 (d, J=0.78 Hz, 3H) 5.38 (br. S. 8H) 6.72 (s, 2H) 7.17-7.22 (m(para), 2H) 7.27-7.35 (m, 3H) 7.52 (d, J=1.17 Hz, 1H) 7.93-7.98 (m(para), 2H) 8.01-8.10 (m, 2H) 8.24 (dd, J=4.79, 1.96 Hz, 1H) 8.34-8.46 (m, 3H) 8.65-8.69 (m, 1H) 9.35 (s, 1H)

Melting Point for the AMG 900 Diurea Salt Crystalline Form A: Onset about 214-215° C.

TABLE 26

AMG 900 Di-Urea Salt Crystalline Form A XRPD pattern data

| Pos. [°2Th.] | FWHM [°2Th.] | d-spacing [Å] |
|---|---|---|
| 6.32 | 0.13 | 13.98 |
| 8.23 | 0.13 | 10.75 |
| 9.83 | 0.16 | 9.00 |
| 12.28 | 0.13 | 7.21 |
| 13.15 | 0.29 | 6.73 |
| 13.54 | 0.13 | 6.54 |
| 14.11 | 0.13 | 6.28 |
| 14.47 | 0.13 | 6.12 |
| 15.42 | 0.13 | 5.75 |
| 15.94 | 0.13 | 5.56 |
| 16.42 | 0.13 | 5.40 |
| 17.36 | 0.10 | 5.11 |
| 17.73 | 0.32 | 5.00 |
| 18.75 | 0.10 | 4.73 |
| 18.95 | 0.16 | 4.68 |
| 19.31 | 0.06 | 4.60 |
| 19.51 | 0.13 | 4.55 |
| 20.31 | 0.19 | 4.37 |
| 21.02 | 0.16 | 4.23 |

TABLE 26-continued

AMG 900 Di-Urea Salt Crystalline Form A XRPD pattern data

| Pos. [°2Th.] | FWHM [°2Th.] | d-spacing [Å] |
|---|---|---|
| 21.31 | 0.10 | 4.17 |
| 22.20 | 0.16 | 4.01 |
| 22.39 | 0.13 | 3.97 |
| 22.80 | 0.13 | 3.90 |
| 23.10 | 0.16 | 3.85 |
| 23.82 | 0.13 | 3.74 |
| 24.26 | 0.16 | 3.67 |
| 24.73 | 0.16 | 3.60 |
| 25.35 | 0.13 | 3.51 |
| 25.81 | 0.13 | 3.45 |
| 26.39 | 0.16 | 3.38 |
| 26.93 | 0.19 | 3.31 |
| 27.50 | 0.19 | 3.24 |
| 29.00 | 0.19 | 3.08 |
| 29.67 | 0.13 | 3.01 |

The X-ray powder diffraction (XRPD) data for the AMG 900 Diurea Salt crystalline Form A is set forth in FIG. 28.

Solubility of Different Salt-Crystal Forms of AMG 900

Figure 29:
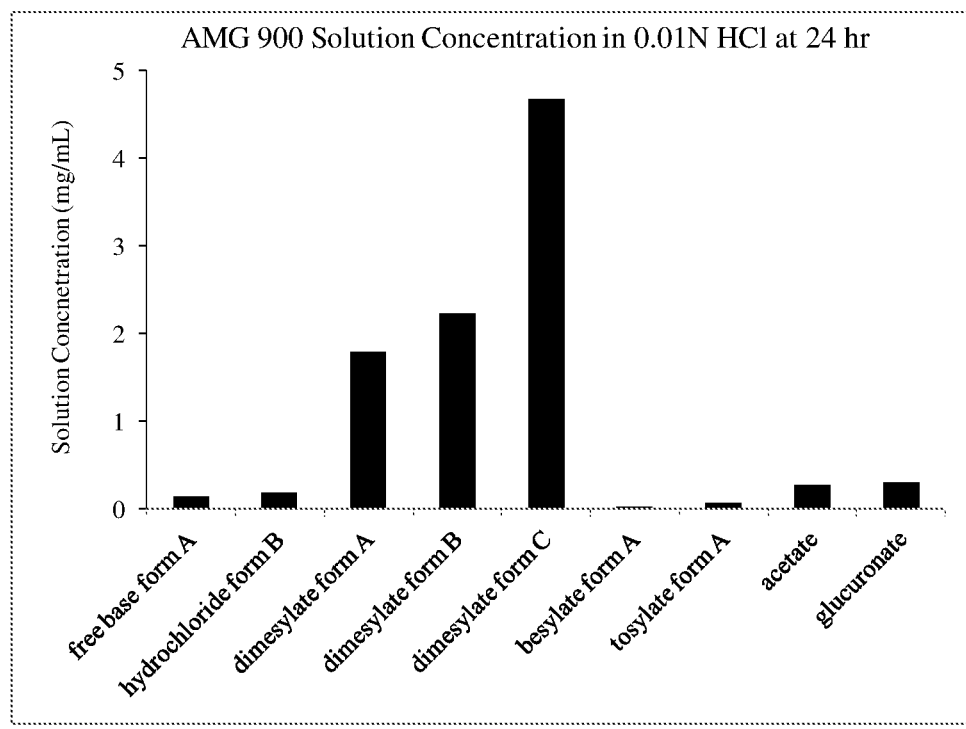
FIG. 29 is a graph depicting the solution concentrations of the bismesylate dihydrate salt crystalline Form B of AMG 900.

The solubility of different salt/solvent/crystal forms of AMG 900 was measured in 0.01N HCl over a period of 24 hrs (simulating the stomach/intestinal environment). The solution concentration of AMG 900 after 24 hrs, as a slurry is shown in FIG. 29. All mesylate salts, including the bismesylate dihydrate form A, the bismesylate dihydrate form B, the bismesylate monohydrate form C and the bismesylate monohydrate form D, showed a significant improvement in solubility over the AMG 900 free base crystalline form A. The solubility of the AMG 900 bismesylate dihydrate crystalline form B was also measured in various aqueous media and solvents for 24 hrs (see Table 27 below), and from a stability perspective, it was found to remain unchanged (stable) except when slurried in aqueous pH 7 and pH 12 where it converted to the free base form C hydrate.

TABLE 27

| Media | Solubility 24 hr (mg/ml) |
|---|---|
| pH 0.5 MSA | 0.676 |
| pH 1.0 MSA | >7.4 |

TABLE 27-continued

| Media | Solubility 24 hr (mg/ml) |
|---|---|
| pH 1.5 MSA | 3.4 |
| pH 2.0 MSA | 1.620 |
| pH 7.0 Phosphate | <0.001 |
| pH 12.0 Phosphate | <0.001 |
| Ethanol | >12 |
| Acetone | 0.020 |
| Ethyl Acetate | <0.001 |
| Acetonitrile (ACN) | 0.383 |
| Dichloroethane (DCE) | 0.008 |
| Methanol | >12 |
| Methanol/Water (9:1) | >12 |
| Isopropyl alcohol | >0.001 |
| Methyl ethyl keone | <0.001 |
| THF | 0.012 |
| DMF | >12 |

AMG 900 bismesylate dihydrate form B was found to remain chemically (no degradation detected by HPLC) and physically stable (by XRPD<TGA and DSC) up to 12 weeks when stored under the accelerated conditions of temperature and humidity of 25° C./60% relative humidity, 40° C./60% RH, 40° C./75% RH and 60° C./Amb. AMG 900 bismesylate dihydrate form B was found to remain chemically and physically stable under proteolytic conditions (1×ICH dose for UV and visible light).

The invention also includes pharmaceutical compositions comprising a crystalline solid state form of a pharmaceutically acceptable salt of AMG 900 and a pharmaceutically acceptable excipient, carrier or diluent. By way of example one such pharmaceutical composition is described in Example 28 below.

The AMG 900 drug product is formulated as powder blends containing AMG 900 bis-mesylate dihydrate filled into white opaque capsules for oral administration. Each capsule contains 1 mg, 5 mg or 25 mg of AMG 900 free base equivalent. A size 2 capsule is used for the 1 mg strength and a size 0 capsule is used for both 5 mg and 25 mg strengths. The capsules are packaged in high-density polyethylene bottles (HDPE) with child-resistant closure (CRC) caps. The bottles are heat-induction sealed. Qualitative and quantitative compositions are provided in Example 28.

Example 28

TABLE 28

(immediately below) describes how persons of ordinary skilled in the art may prepare a gelatin capsule of AMG 900 in dosage strengths of 1-mg, 5-mgs and 25-mgs.

| | Strength | | | | | | |
|---|---|---|---|---|---|---|---|
| | 1 mg | | 5 mg | | 25 mg | | |
| Component | Quantity/capsule | % (w/w) | Quantity/capsule | % (w/w) | Quantity/capsule | % (w/w) | Function |
| AMG 900 bis-mesylate dihydrate (free base anhydrous equivalent)[a] | 1.50 (1.00) | 1.02 | 7.49 (5.00) | 3.05 | 37.43 (25.00) | 9.15 | Active |
| Microcrystalline cellulose, NF (Avicel PH102) | 110.80 | 75.23 | 179.68 | 73.2 | 274.51 | 67.1 | Filler |
| Mannitol, NF (Mannogem EZ) | 23.56 | 16.00 | 39.27 | 16.0 | 65.46 | 16.0 | Filler |
| Sodium starch glycolate, NF (Explotab) | 8.84 | 6.00 | 14.73 | 6.00 | 24.55 | 6.00 | Disintegrant |

TABLE 28-continued (immediately below) describes how persons of ordinary skilled in the art may prepare a gelatin capsule of AMG 900 in dosage strengths of 1-mg, 5-mgs and 25-mgs.

| Component | Strength | | | | | | Function |
|---|---|---|---|---|---|---|---|
| | 1 mg | | 5 mg | | 25 mg | | |
| | Quantity/capsule | % (w/w) | Quantity/capsule | % (w/w) | Quantity/capsule | % (w/w) | |
| Colloidal silicon dioxide, NF (Cab-O-Sil M5P) | 1.47 | 1.00 | 2.45 | 1.00 | 4.09 | 1.00 | Anti-adherent |
| Magnesium stearate, NF (non-bovine) | 1.10 | 0.75 | 1.84 | 0.75 | 3.07 | 0.75 | Lubricant |
| Total | 147.28 | 100 | 245.46 | 100 | 409.10 | 100 | |

[a]AMG 900 free base purity = 66.8% (lot 0010018397, Certificate of Analysis PRDS 001410). Molecular weights of the AMG 900 bis-mesylate dihydrate and the free base anhydrous are 731.82 and 503.58, respectively. Therefore, the anhydrous free base accounts for 68.8% of the bis-mesylate dihydrate.

Each of the 1-mg and 25-mg capsule were found to be stable when stored for one month at 25° C./60% RH and 40° C./75% RH. In addition, the capsule contents showed no significant change in appearance, and no change in chemical assay and no additional impurities were identified.

INDICATIONS

The present invention provides a compound, AMG 900, a pan Aurora kinase A, B and C inhibitor, which possesses the ability to treat various types of cancer, including cancer that has relapsed, or become refractory to traditional, standard of care anti-cancer agents or cancer fighting therapeutics. Aurora kinases are enzymes of the serine/threonine kinase family of proteins, which play an important role in play a part in cell cycling, and in particular in protein phosphorylation during the mitotic phase of the cell cycle. Therefore, activation and/or over expression of Aurora kinase proteins is common in proliferating or oncolytic cells.

There are three known members of the Aurora kinase family, Aurora A, Aurora B and Aurora C, also commonly referred to as Aurora 2, Aurora 1, and Aurora 3, respectively. The specific function of each Aurora kinase member in mammalian cell cycle has been studied. Aurora-A is localized to the centrosome during interphase and is important for centrosome maturation and to maintain separation during spindle assembly. Aurora-B localizes to the kinetochore in the G2 phase of the cell cycle until metaphase, and relocates to the midbody after anaphase. Aurora-C was thought to function only in meiosis, but more recently has been found to be more closely related to Aurora-B, showing some overlapping functions and similar localization patterns in mitosis. Each aurora kinase appears to share a common structure, including a highly conserved catalytic domain and a very short N-terminal domain that varies in size. (See R. Giet and C. Prigent, J. Cell. Sci., 112:3591-3601 (1999)).

Aurora kinases appear to be viable targets for the treatment of cancer. Aurora kinases are overexpressed in various types of cancers, including colon, breast, lung, pancrease, prostate, bladder, head, neck, cervix, and ovarion cancers. The Aurora-A gene is part of an amplicon found in a subset of breast, colon, ovarian, liver, gastric and pancreatic tumors. Aurora-B has also been found to be overexpressed in most major tumor types. Overexpression of Aurora-B in rodent fibroblasts induces transformation, suggesting that Aurora-B is oncogenic. More recently, Aurora-B mRNA expression has been linked to chromosomal instability in human breast cancer. (Y. Miyoshi et al., Int. J. Cancer, 92:370-373 (2001)).

Further, inhibition of one or more of the Aurora kinases by several parties has been shown to inhibit cell proliferation and trigger apoptosis in several tumor cell lines. Particularly, inhibition of Aurora has been found to arrest cell cycling and promote programmed cell death via apoptosis. Accordingly, there has been a strong interest in finding inhibitors of Aurora kinase proteins.

Thus, the present invention provides uses of the new crystalline forms of AMG 900 salts in treating cancer. AMG 900, as an active pharmaceutical ingredient, was shown to possess aurora kinase inhibitory characteristics. Specifically AMG 900 potently inhibited the kinase activity of all 3 aurora kinases (aurora kinase A, $IC_{50}$=0.005 μM; aurora kinase B, $IC_{50}$=0.004 μM; and aurora kinase C, $IC_{50}$=0.001 μM) with selectivity against other kinases. In HeLa cells, AMG 900 inhibited autophosphorylation of aurora kinases A and B and p-Histone H3 in a dose-dependent manner (Table 29). AMG 900 exhibited a time-dependent increase in potency in Jurkat cells. The $IC_{50}$ for p-Histone H3 was 0.066 μM when Jurkat cells were analyzed 1 hour after the beginning of treatment compared with 0.004 μM after 24 hours of treatment.

TABLE 29

Summary of AMG 900 Aurora Biochemical $IC_{50}$ Values in HeLa Cells

| Pre-treatment | Assay Format | Aurora Biomarker | Treatment Time | $IC_{50}$ (μM) | SD (μM) |
|---|---|---|---|---|---|
| HeLa Asynchronous | High-content cell imaging* | p-Histone H3 | 1 hour | 0.059 | 0.015 |
| HeLa Mitotic fraction | Flow cytometry** | p-Aurora A | 1.25 hours | 0.118 | 0.026 |
| | | p-Histone H3 | 1.25 hours | 0.238 | 0.045 |

*Cellomics Arrayscan VTi high-content cell imaging analysis. Mean $IC_{50}$ value (n = 13)
**Flow cytometry-based analysis. HeLa cells were synchronized in mitosis with nocodazole for 12 hours, harvested and treated with dimethyl sulfoxide or AMG 900. Treated cells were subdivided in half and immuno-stained with p-Aurora A and p-Histone H3 antibodies. Mean $IC_{50}$ value (n = 2, independent experiments)

The biological potencies, ie. the inhibitory potency on aurora kinases and therapeutic uses related thereto, of AMG 900 are also described on pages 83 and 157-161 of PCT publication WO0207087276, which specification is hereby incorporated herein in its entirety. More importantly, AMG 900 possesses the ability to treat cancerous tumors in-vivo in PCT publication WO2011031842 and WO2013149026, both specifications of which are hereby incorporated herein in their entireties.

The present invention further provides use of a crystalline form of a pharmaceutically acceptable salt of AMG 900 to treat various types of cancer, including cancer that has relapsed, or become refractory to traditional, standard of care chemotherapeutic agents, including antimitotic agents, such as taxanes (paclitaxel and docetaxel) and vinca alkaloids. In addition, AMG 900 has the ability to treat cancers that are resistant to other Aurora kinase inhibiting agents, including but not limited to AZD 1152, VX-680 and PHA-739358. These beneficial uses of AMG 900 are described in PCT publication no WO2011031842, the specification pages 5, 6 and 11-38 of which are hereby incorporated by reference in their entireties. Generally, such tumors develop resistance as a result of previous and/or prolonged treatment with anti-cancer agents. Accordingly, in one embodiment of the invention, there is provided a method of treating cancer in a subject, the method comprising administering to a subject in need thereof an effective dosage amount of a crystalline form of AMG 900, or a pharmaceutically acceptable salt thereof, according to any one of embodiments 1-25 as described herein.

In embodiment 61, the invention provides a method of treating a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma or a hematopoietic tumor of myeloid lineage selected from acute and chronic myelogenous leukemias, myelodysplastic syndrome and promyelocytic leukemia or a combination thereof in a subject in need thereof, the method comprising administering to the subject an effective dosage amount of a crystalline form of a pharmaceutically acceptable salt of AMG 900, according to any one of embodiments 1-40, as described herein.

In embodiment 62, the invention provides use of the crystalline form of a pharmaceutically acceptable salt of AMG 900 according to embodiment 61 wherein the hematopoietic tumor of myeloid lineage selected from acute and chronic myelogenous leukemias, myelodysplastic syndrome and promyelocytic leukemia or a combination thereof.

In embodiment 63, the invention provides use of the crystalline form of a pharmaceutically acceptable salt of AMG 900 according to embodiment 61 wherein the hematopoietic tumor is selected from acute myelogenous leukemias (AML), chronic myelogenous leukemia (CML) and myelodysplastic syndrome (MDS).

In embodiment 64, the invention provides use of the crystalline form of a pharmaceutically acceptable salt of AMG 900 according to embodiment 63 wherein the hematopoietic tumor is selected from acute myelogenous leukemias (AML) and chronic myelogenous leukemia (CML).

In embodiment 65, the invention provides use of the crystalline form of a pharmaceutically acceptable salt of AMG 900 according to embodiment 61 wherein the hematopoietic tumor is acute myelogenous leukemias (AML).

In embodiment 66, the invention provides use of the crystalline form of a pharmaceutically acceptable salt of AMG 900 according to embodiment 61 wherein the hematopoietic tumor is chronic myelogenous leukemia (CML).

In embodiment 66, the invention provides a crystalline form of a pharmaceutically acceptable salt of AMG 900 according to any one of embodiments 1-40 for use in the treatment of a solid tumor selected from cancer of the bladder, breast, colon, kidney, liver, lung, small cell lung cancer, esophagus, gall-bladder, ovary, pancreas, stomach, cervix, thyroid, prostate and skin.

In embodiment 67, the invention provides a crystalline form of a pharmaceutically acceptable salt of AMG 900 according to any one of embodiments 1-40 for use in the treatment of a solid tumor cancer selected from cancer of the bladder, breast, colon, kidney, liver, lung, non-small cell lung, head and neck, esophageal, gastric, ovary, pancreas, stomach, cervix, thyroid and prostate or for use in the treatment of a hematologic cancer selected from lymphoma or leukemia.

In embodiment 68, the invention provides use, of the crystalline form of a pharmaceutically acceptable salt of AMG 900, according to claim 67 wherein the cancer is prostate cancer, ovarian cancer, breast cancer, cholangiocarcinoma, acute myeloid leukemia, chronic myeloid leukemia or a combination thereof.

In embodiment 69, the invention provides use, of the crystalline form of a pharmaceutically acceptable salt of AMG 900, according to any one of embodiments 66-68 wherein the cancer is prostate cancer, ovarian cancer, breast cancer, cholangiocarcinoma, acute myeloid leukemia, chronic myeloid leukemia or a combination thereof.

In embodiment 70, the invention provides use, of the crystalline form of a pharmaceutically acceptable salt of AMG 900, according to any one of embodiments 66-68 wherein the cancer is prostate cancer, ovarian cancer, triple negative breast cancer, acute myeloid leukemia, chronic myeloid leukemia or a combination thereof.

In embodiment 71, the invention provides use, of the crystalline form of a pharmaceutically acceptable salt of AMG 900, according to any one of embodiments 66-68 wherein the cancer is prostate cancer, ovarian cancer or triple negative breast cancer, or a combination thereof.

In embodiment 72, the invention provides use, of the crystalline form of a pharmaceutically acceptable salt of AMG 900, according to any one of embodiments 66-68 wherein the cancer is prostate cancer.

In embodiment 73, the invention provides use, of the crystalline form of a pharmaceutically acceptable salt of AMG 900, according to any one of embodiments 66-68 wherein the cancer is ovarian cancer.

In embodiment 74, the invention provides use, of the crystalline form of a pharmaceutically acceptable salt of AMG 900, according to any one of embodiments 66-68 wherein the cancer is breast cancer.

In embodiment 75, the invention provides use, of the crystalline form of a pharmaceutically acceptable salt of AMG 900, according to any one of embodiments 66-68 wherein the cancer acute myeloid leukemia.

In embodiment 76, the invention provides use, of the crystalline form of a pharmaceutically acceptable salt of AMG 900, according to any one of embodiments 66-68 wherein the cancer is chronic myeloid leukemia.

In embodiment 77, the invention provides use according to any one of embodiments 62-76 wherein the crystalline form of a pharmaceutically acceptable salt of AMG 900 is a crystalline Form A, B, C, D, E, F or G of a bismesylate salt of AMG 900.

In embodiment 78, the invention provides use according to any one of embodiments 62-76 wherein the crystalline form of a pharmaceutically acceptable salt of AMG 900 is the crystalline Form B of a bismesylate salt of AMG 900.

In embodiment 78a, the invention provides use according to any one of embodiments 62-76 wherein the crystalline form of a pharmaceutically acceptable salt of AMG 900 is the crystalline Form B of a bismesylate dihydrate salt of AMG 900.

In embodiment 79, the invention provides a crystalline form of a pharmaceutically acceptable salt of AMG 900 according to any one of embodiments 1-40 for use treatment of a subject's cancer that was previously treated with an anti-cancer agent, including for example, a chemotherapeutic agent.

In embodiment 80, the invention provides the use of embodiment 79 wherein the chemotherapeutic agent is an antimitotic agent or an anthracycline.

In yet embodiment 81, the invention provides the use of any one of embodiments 79 and 80 wherein the chemotherapeutic agent is an agent selected from the group consisting of taxol, docetaxel, vincristine, vinblastine, vindesine, and vinorelbine, daunorubicin, doxorubicin, idarubicin, epirubicin, and mitoxantrone.

In embodiment 82, the invention provides the use of embodiment 79 wherein the anti-cancer agent is AZD1152, PHA-739358, MK-0457 or a combination thereof.

As such, AMG 900 may be used to treat cellular proliferation disorders, including uncontrolled cell growth and aberrant cell cycle regulation, which also have been previously treated with taxanes standard-of-care therapies.

To this end, the crystalline forms of the various pharmaceutically acceptable salts of AMG 900 provided by the invention, including those disclosed herein, are useful for, but not limited to, the prevention or treatment of cancer including, for example, various solid and hematologically derived tumors, such as carcinomas, including, without limitation, cancer of the bladder, breast, colon, kidney, liver, lung (including small cell lung cancer), esophagus, gallbladder, ovary, pancreas, stomach, cervix, thyroid, prostate, uterus and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias (AML and CML), myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma), where such cancers have relapsed or become refractory. Cancers, such as prostate cancer, ovarian cancer, lung cancer, breast cancer, cholangiocarcinoma or other types of cancer, which have become refractory to anti-cancer treatment, such as with hormones, may also be treated with AMG 900.

In embodiment 83, the invention provides a method of treating one or more cancers selected from the group consisting of uterine cancer, breast cancer, lung cancer including non-small cell lung cancer, colon cancer, prostate cancer, skin cancer, kidney cancer, liver cancer, leukemias including promyelocytic leukemia, chronic myeloid leukemia and T-cell leukemia, multiple myeloma, ovarian cancer and bone marrow cancer in a subject, the method comprising administering to the subject an effective dosage amount of a bismesylate crystalline Form B salt of AMG 900, wherein the subject's cancer has previously been treated with and become refractory to one or more chemotherapeutic agents selected from the group consisting of doxorubicin, daunorubicin, dactinomycin, colchicine, vinblastine, vincristine, paclitaxel, docetaxel, etoposide and mitoxantrone.

In embodiment 84, the invention provides a method of treating one or more cancers selected from the group consisting of cancer of the bladder, breast, colon, kidney, liver, lung, non-small cell lung, head and neck, esophageal, gastric, ovarian, pancreas, stomach, cervix, thyroid and prostate or a lymphoma or leukemia in a subject, the method comprising administering to the subject an effective dosage amount of a bismesylate crystalline Form B salt of AMG 900.

In embodiment 85, the invention provides a bismesylate crystalline Form B salt of AMG 900 in a dose effective amount useful for treating advanced solid tumors, including without limitations, tumors of the bladder, breast, colon, kidney, liver, lung, non-small cell lung, head and neck, esophageal, gastric, ovarian, pancreas, stomach, cervix, thyroid and prostate.

In embodiment 85a, the invention provides a bismesylate dihydrate crystalline Form B salt of AMG 900 in a dose effective amount useful for treating advanced solid tumors, including without limitations, tumors of the bladder, breast, colon, kidney, liver, lung, non-small cell lung, head and neck, esophageal, gastric, ovarian, pancreas, stomach, cervix, thyroid and prostate.

The invention also provides a method for the treatment of solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

In embodiment 86, the invention provides a method of treating a solid tumor, including non-small cell lung cancer, breast cancer, and prostate cancer in a subject, the method comprising administering a bismesylate crystalline Form B salt of AMG 900 in a dosage regimen to the subject, the dosage regimen comprising administering to the subject a dose of the bismesylate crystalline form B AMG 900 ranging from about 1 mg to about 50 mg.

In embodiment 87, the dosage amount of the bismesylate crystalline form B AMG 900 administered to the subject in embodiment 86 ranges from about 1.5 mg to about 45 mg.

In embodiment 88, the dose of the bismesylate crystalline form B AMG 900 administered to the subject in any one of embodiments 86 and 87 ranges from about 5 mg to about 45 mg.

In embodiment 89, the dose of the bismesylate crystalline form B AMG 900 administered to the subject in any one of embodiments 86-88 ranges from about 10 mg to about 40 mg.

In embodiment 90, the dose of the bismesylate crystalline form B AMG 900 administered to the subject in any one of embodiments 86-89 ranges from about 15 mg to about 40 mg.

In embodiment 91, the dose of the bismesylate crystalline form B AMG 900 administered to the subject in any one of embodiments 86-90 ranges from about 16 mg to about 35 mg.

In embodiment 92, the dose of AMG 900 administered to the subject in any one of embodiments 86-91 ranges from about 16 mg to about 24 mg.

In embodiment 93, the dose of AMG 900 administered to the subject in any one of embodiments 86-91 ranges from about 16 mg to about 30 mg.

In embodiment 94, the dose of AMG 900 administered to the subject in any one of embodiments 86-93 is about 16 mg.

In embodiment 95, the dose of AMG 900 administered to the subject in any one of embodiments 86-92 is about 24 mg.

In embodiment 96, the dose of AMG 900 administered to the subject in embodiment 86 ranges from about 5 mg to about 100 mg.

In embodiment 97, the invention provides the method described embodiment 86, wherein the dosage regimen comprises orally administering the dose of AMG 900 to the subject once daily for 3, 4, 5, 6, 7, 8, 9 or 10 consecutive days or the patient is "on" AMG 900 once daily for 3, 4, 5, 6, 7, 8, 9 or 10 consecutive days.

In embodiment 98, the invention provides a method according to any one of embodiments 86 and 97, wherein the regimen further comprises non-treatment of AMG 900 for a period ranging from 6 days to 20 days immediately following the once daily consecutive day treatment of AMG 900, or the patient is "off" of AMG 900 dosing for a period ranging from 6 days to 20 days immediately following the once daily consecutive day treatment.

In embodiment 99, the invention provides a method according to any one of embodiments 86 and 97, wherein the dosage regimen comprises orally administering the dose of AMG 900 to the subject once daily for 4, 5, 6 or 7 consecutive days followed immediately by non-treatment of AMG 900 for a period ranging from 6 days to 20 days, or even orally administering the dose of AMG 900 to the subject once daily for 4 or 7 consecutive days followed immediately by non-treatment of AMG 900 for a period ranging from 6 days or 15 days.

The invention further provides additional embodiments of varying dosing regimen or dosing schedules are described herein below.

Tumor Response Results

AMG 900 has exhibited positive responses in various solid tumor types in the human Ph I clinical trial at doses prescribed in accordance with the "on-off" dosage schedule described above.

As shown in FIGS. 30A, 30B, 31A, 31B, 32A, 32B, 33A, 33B, 34A and 34B, AMG 900 displayed a surprising property of being able to reduce or decrease the physical size of a solid tumor in both the ovary as well as in the endometrial lining of the uterus wall. This anti cancer activity was observed with low dosages of bismesylate crystalline Form B salt of AMG 900, as low as a once daily 8 mg dose. Importantly, MTD's and DLT's were not observed until doses of bismesylate crystalline Form B salt of AMG 900 were much greater than 8 mg, thus allowing higher doses of bismesylate crystalline Form B salt of AMG 900 and/or varied dosage regimens to provide meaningful and significant anti-cancer benefits to patients.

Figure 30A:
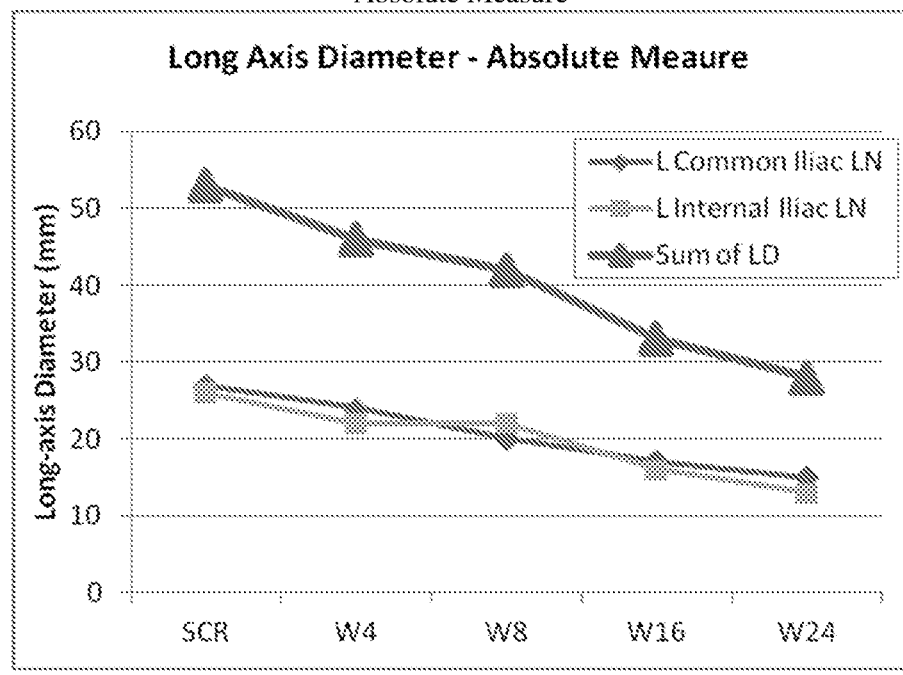
FIGS. 30A and 30B depicts the positive effects of orally administered AMG 900 bismesylate dihydrate salt crystalline form B on a patient with stage IV solid endometrial cancerous tumor as measured by its long axis diameter.
Figure 30B:
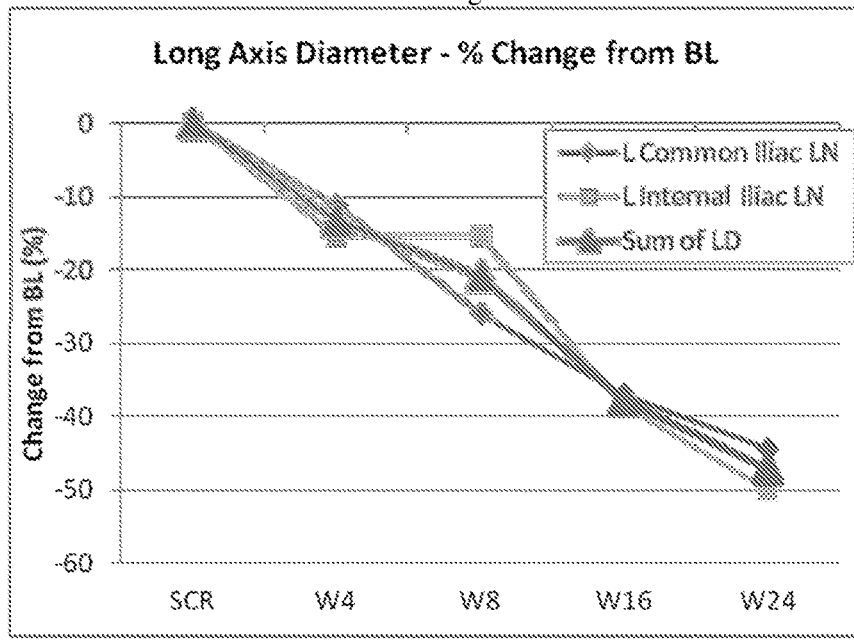

As shown in FIGS. 30A and 30B, and particularly illustrated in FIG. 30B, an bismesylate crystalline Form B salt of AMG 900 dosage regiment comprising of dosing AMG 900 at a dose of about 30 mg once daily for four (4) consecutive days ("on" treatment) and then non-treatment for 10 consecutive days ("off" treatment), followed by "on" once daily treatment again for four (4) consecutive days followed again by "off" treatment for 10 consecutive days, and so on and so off for 24 weeks, had a positive response in a patient with advanced solid endometrial cancerous tumor at week no. 24. Specifically, FIG. 30A illustrates diametric measurements along the long axis of the tumor dosed with 30 mg+GCSF once daily over a period of two (12) cycles, ie., 24 weeks (168 days). The figure reveals, as measured by CT and calculated using RECIST 1.0, that the long axis diameter was decreased by approximately 50% at week 24 (see FIG. 30B) versus the base line diameter of the same tumor on day 1. This is clear evidence of clinical benefit of AMG 900 at dose of 30 mg over a specified dosing regimen.

Figure 31A:
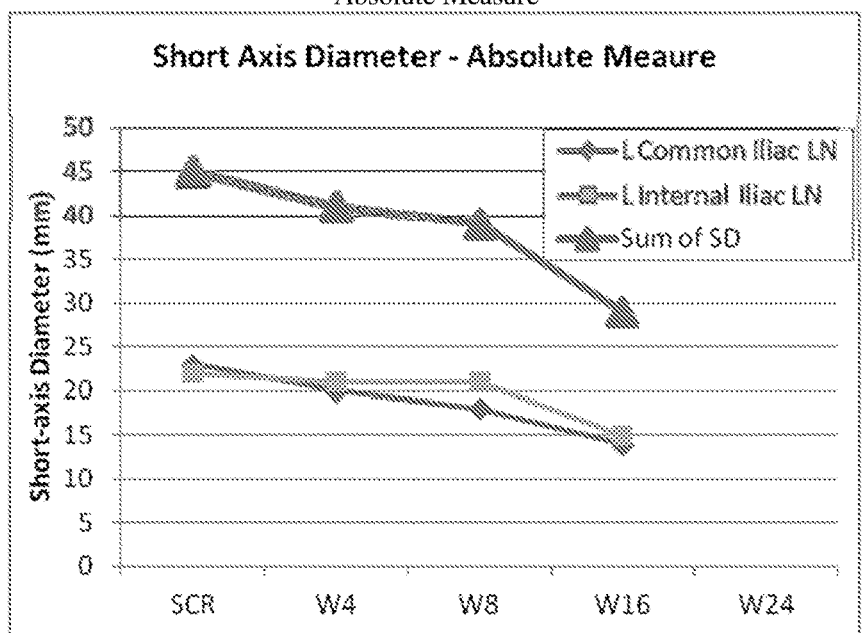
FIGS. 31A and 31B depicts the positive effects of orally administered AMG 900 bismesylate dihydrate salt crystalline form B on a patient with stage IV solid endometrial cancerous tumor as measured by its short axis diameter.
Figure 31B:
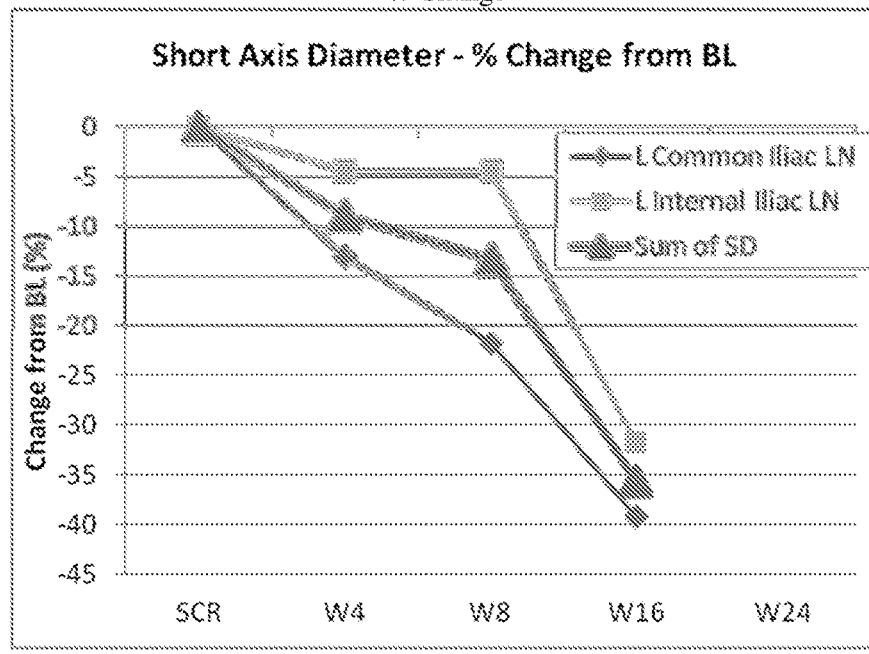

FIGS. 31A and 31B confirm the finding of FIGS. 30A and 30B. FIGS. 31A and 31B are measurements of the same endometrial solid tumor depicted in FIGS. 30A and 30B, but with its size shown as measured alone the short axis by CT and calculated using RECIST 1.1. As shown in FIG. 30B, the short axis diameter at week 16 was reduced by up to 40% after eight (8) cycles of treatment with 30 mg once daily dose of AMG 900.

Figure 32A:
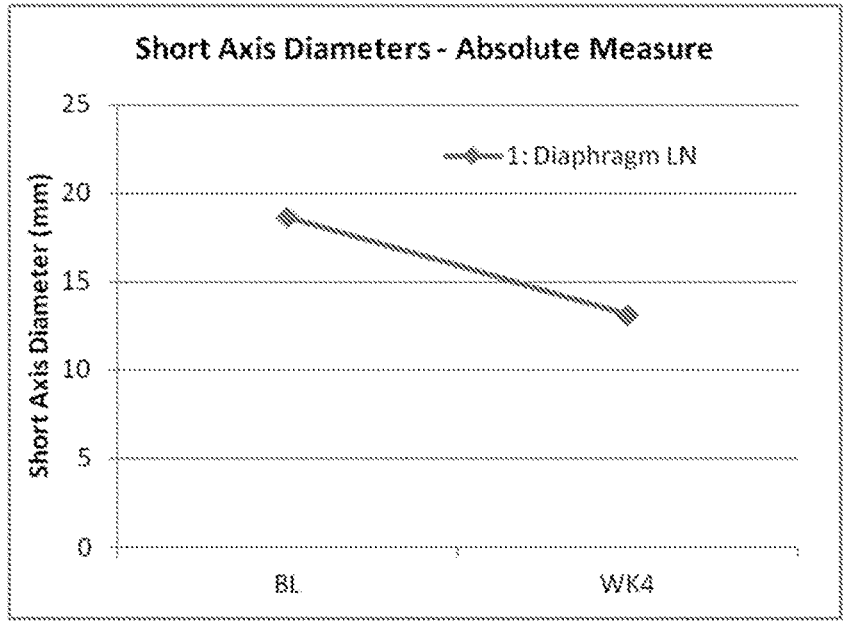
FIGS. 32A and 32B depicts the positive effects of orally administered AMG 900 bismesylate dihydrate salt crystalline form B on a patient with stage IV-B solid ovarian cancerous tumor as measured by its short axis diameter.
Figure 32B:
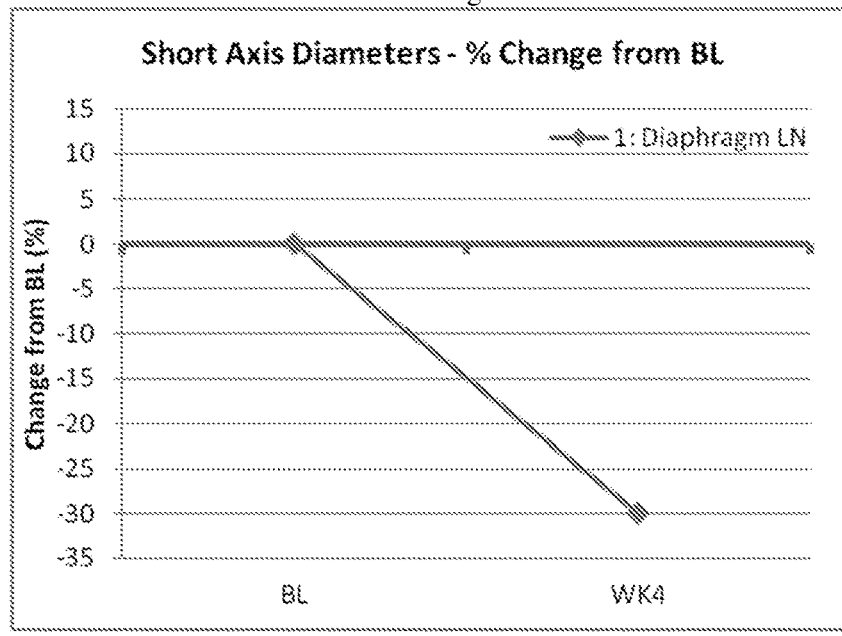

As shown in FIGS. 32A and 32B, and particularly illustrated in FIG. 32B, an bismesylate crystalline Form B salt of AMG 900 dosage regiment comprising of dosing the bismesylate crystalline Form B salt of AMG 900 at a dose ranging from about 16 mg to about 30 mg once daily for four (4) consecutive days ("on" treatment) and then non-treatment for 10 consecutive days ("off" treatment), followed by "on" once daily treatment again for four (4) consecutive days followed again by "off" treatment for 10 consecutive days, and so on and so off, had a positive response in a patient with advanced solid ovarian cancerous tumor at week no. 4. Specifically, FIG. 32A illustrates diametric measurements along the short axis of the tumor dosed with 30 mg once daily over a period of two (2) cycles, ie., 4 week (28 days). The figure reveal, as measured by RECIST 1.1, that the short axis diameter had reduced by approximately 30% (see FIG. 32B) versus the base line diameter of the same tumor on day 1. This is clear evidence of clinical benefit of bismesylate crystalline Form B salt of AMG 900 at 30 mg.

Figure 33A:
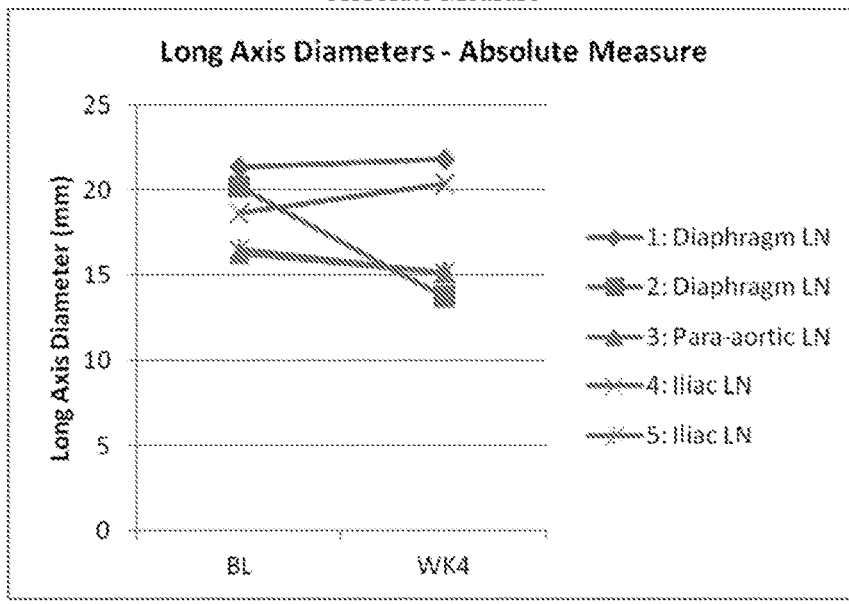
FIGS. 33A and 33B depicts the positive effects of orally administered AMG 900 bismesylate dihydrate salt crystalline form B on a patient with stage IV-B solid ovarian cancerous tumor as measured by its long axis diameter per a central read.
Figure 33B:
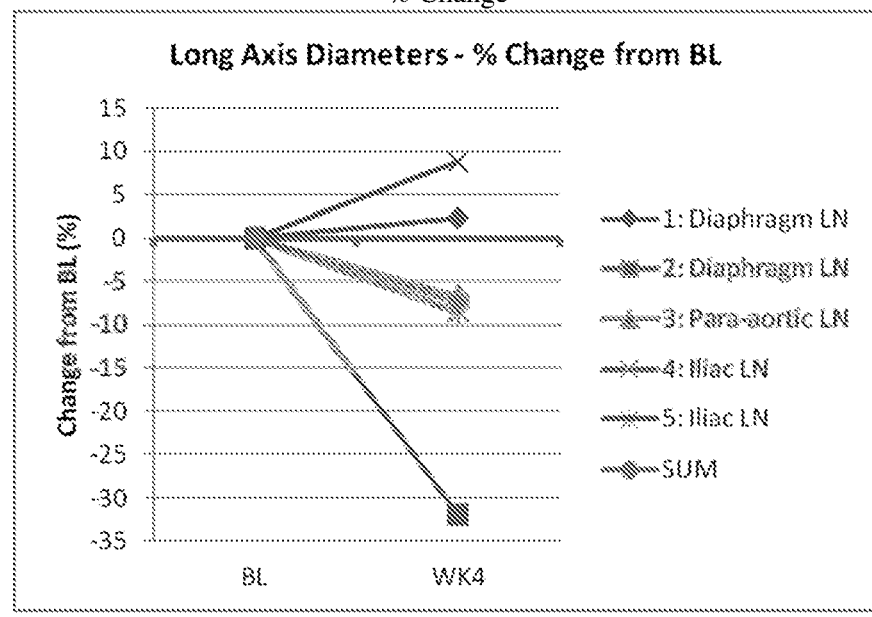

FIGS. 33A and 33B confirm the finding of FIGS. 32A and 32B. FIGS. 33A and 33B are measurements of the same ovarian tumor depicted in FIGS. 32A and 32B, but with its size shown as measured alone the long axis by RECIST 1.0. As shown in FIG. 34-b, the long axis diameter at week 4 had reduced by between 30 and 35% after two (2) cycles of treatment with 30 mg once daily doses of bismesylate crystalline Form B salt of AMG 900.

Figure 34A:
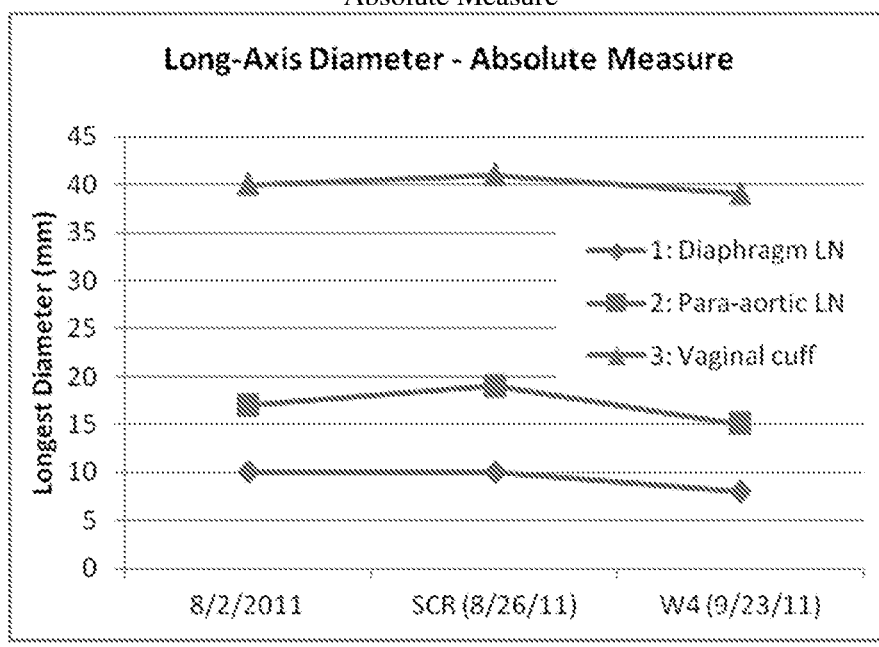
FIGS. 34A and 34B depicts the positive effects of orally administered AMG 900 bismesylate dihydrate salt crystalline form B on a patient with a stage IV-B solid ovarian cancerous tumor as measured by its long axis diameter per a local read.
Figure 34B:
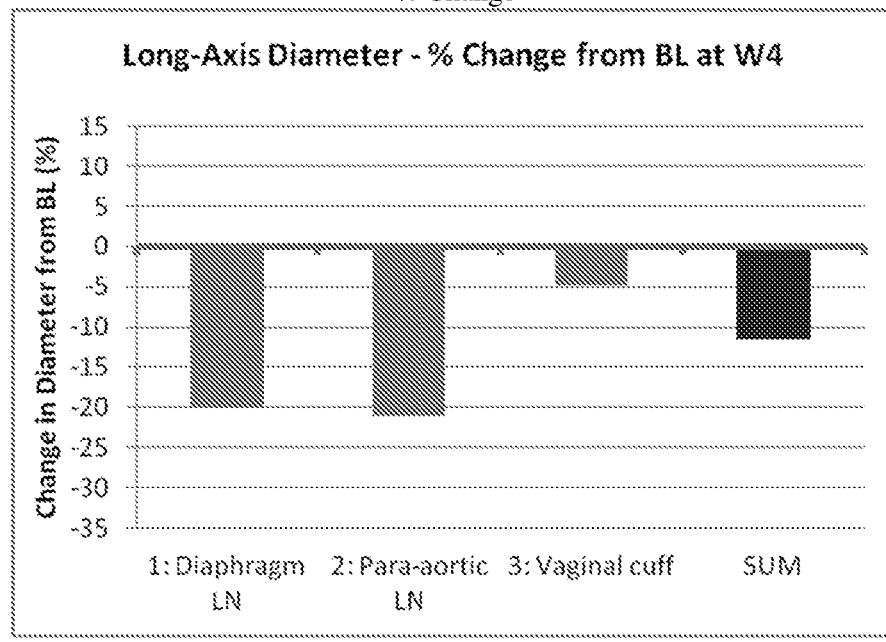

FIGS. 34A and 34B illustrate that other membranes and linings of the subject's ovarian tumors also exhibited positive responses with 4-day on-10 day off, 2-cycle treatment with bismesylate crystalline Form B salt of AMG 900 at a once daily dose of 30 mg/kg. More specifically, the cancerous portions of the vaginal cuff, para-aortic and diaphragm areas of the uterus decreased from about 10% to about 25% when compared with base line.

Further to substantiate the positive effects of AMG 900 on ovarian cancer, a 66-year old platinum-sensitive ovarian cancer patient, who had 3 prior platinum treatment regimens (last PFS, 21 months) and had cyclical grade 4 neutropenia, was dosed bismesylate crystalline Form B salt of AMG 900 at 16 mg once daily pursuant the 4-day on-10 day off regimen/cycle described above. The once daily dose was reduced to 8 mg for cycles 4-15, then increased to 12 mg at cycle 16. At the end of cycle 16, the tumor exhibited a positive response with a 16% decrease in SLD (sum of long axis diameters) on CT and a 45% decrease in CA-125. This further verifies the positive effects of bismesylate crystalline Form B salt of AMG 900, when dosed according to a specified cycle, on solid cancerous tumors.

Additional cancer subjects of the first-in-human Ph I trial were treated with AMG 900 in accordance with the dose escalation schedule protocol and the dosage cycle described above, and exhibited results wherein the tumors were stabilized. More specifically, patients having gastroesophogeal cancer, lung cancer, breast cancer, colon cancer, paraganglioma and medullary thyroid cancer, each in the form of an advanced solid tumor, all exhibited stabilization in growth of the tumors and/or decreases in size ranging from about 5% to about 10% of the tumor. The sizes were measured, and decreases determined, by the methods described herein. This is further evidence of the use of AMG 900 in treating various forms of cancer.

In the following embodiments 101-169 of the present invention the term "AMG 900" as used in the embodiment is intended to refer to "AMG 900 bismesylate salt crystalline form B." In some of these embodiments, it is listed as such, while in others it is recited as AMG 900. The present invention further provides a method of treating cancer in a subject comprising administering to the subject a dosage regimen comprising a once daily dose of AMG 900 bismesylate salt crystalline form B ranging from about 1 mg to about 50 mg (embodiment 101).

In embodiment 102, the invention provides the method of embodiment 101, wherein the dosage regimen comprises orally administering the once daily dose of AMG 900 bismesylate salt crystalline form B to the subject for 3, 4, 5, 6, 7, 8, 9 or 10 consecutive days.

In embodiment 103, the invention provides the method of any one of embodiments 101 and 102, wherein the dosage regimen comprises orally administering the once daily dose of AMG 900 bismesylate salt crystalline form B to the subject for 3, 4, 5, 6 or 7 consecutive days.

In embodiment 104, the invention provides the method of any one of embodiments 101-103, wherein the dosage regimen comprises orally administering the once daily dose of AMG 900 bismesylate salt crystalline form B to the subject for 4, 5, 6 or 7 consecutive days.

In embodiment 105, the invention provides the method of any one of embodiments 101-104, wherein the dosage regimen comprises orally administering the once daily dose of AMG 900 bismesylate salt crystalline form B to the subject for 4 consecutive days.

In embodiment 106, the invention provides the method of any one of embodiments 101-104, wherein the dosage regimen comprises orally administering the once daily dose of AMG 900 bismesylate salt crystalline form B to the subject for 7 consecutive days.

In embodiment 107, the invention provides the method of any one of embodiments 101-106, wherein the dosage regimen further comprises non-treatment of AMG 900 bismesylate salt crystalline form B for a period ranging from 6 to 20 consecutive days immediately following the once daily consecutive day treatment of AMG 900 bismesylate salt crystalline form B.

In embodiment 108, the invention provides the method of any one of embodiments 101-107, wherein the dosage regimen further comprises non-treatment of AMG 900 bismesylate salt crystalline form B for a period ranging from 10 to 20 consecutive days immediately following the once daily consecutive day treatment of AMG 900 bismesylate salt crystalline form B.

In embodiment 109, the invention provides the method of any one of embodiments 101-108, wherein the dosage regimen further comprises non-treatment of AMG 900 bismesylate salt crystalline form B for a period ranging from 10 to 12 consecutive days immediately following the once daily consecutive day treatment of AMG 900 bismesylate salt crystalline form B.

In embodiment 110, the invention provides the method of any one of embodiments 101-109, wherein the dosage regimen further comprises non-treatment of AMG 900 bismesylate salt crystalline form B for a period of 10 consecutive days immediately following the once daily consecutive day treatment of AMG 900 bismesylate salt crystalline form B.

In embodiment 111, the invention provides the method of any one of embodiments 101-110, wherein the dosage regimen comprises orally administering the once daily dose of AMG 900 bismesylate salt crystalline form B to the subject for 4, 5, 6 or 7 consecutive days followed immediately by non-treatment of AMG 900 bismesylate salt crystalline form B for a period ranging from 6 to 20 consecutive days.

In embodiment 112, the invention provides the method of any one of embodiments 101-111, wherein the dosage regimen comprises orally administering the once daily dose of AMG 900 bismesylate salt crystalline form B to the subject for 4 or 7 consecutive days followed immediately by non-treatment of AMG 900 bismesylate salt crystalline form B for a period ranging from 6 to 15 consecutive days.

In embodiment 113, the invention provides the method of any one of embodiments 101-112, wherein the dosage regimen comprises orally administering the once daily dose of AMG 900 bismesylate salt crystalline form B to the subject for 4 consecutive days followed immediately by non-treatment of AMG 900 bismesylate salt crystalline form B for a period of 10 consecutive days.

In embodiment 114, the invention provides the method of any one of embodiments 101-113, wherein the dosage regimen comprises orally administering AMG 900 bismesylate salt crystalline form B to the subject in a once daily dose or dosage amount ranging from about 8 mg to about 40 mg for 4 consecutive days followed immediately by non-treatment of AMG 900 bismesylate salt crystalline form B for a period of 10 consecutive days.

In embodiment 115, the invention provides the method of any one of embodiments 101-114, wherein the dosage regimen comprises orally administering AMG 900 bismesylate salt crystalline form B to the subject in a once daily dose or dosage amount ranging from about 16 mg to about 40 mg for 4 consecutive days followed immediately by non-treatment of AMG 900 bismesylate salt crystalline form B for a period of 10 consecutive days.

In embodiment 116, the invention provides the method of any one of embodiments 101-115, wherein the dosage regimen comprises orally administering AMG 900 bismesylate salt crystalline form B to the subject in a once daily dose ranging from about 16 mg to about 30 mg for 4 consecutive days followed immediately by non-treatment of AMG 900 bismesylate salt crystalline form B for a period of 10 consecutive days.

In embodiment 117, the invention provides the method of any one of embodiments 101-116 wherein the cancer is one or more of (a) a solid or hematologically derived tumor selected from (a) cancer of the bladder, breast, colon, kidney, liver, lung, small cell lung cancer, esophagus, gall-bladder, ovary, endometrium, pancreas, stomach, uterus, cervix, thyroid, brain, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, and (f) a melanoma, seminoma, teratocarcinoma, osteosarcoma, xenoderoma pigmentosum, keratoctanthoma, thyroid follicular cancer or Kaposi's sarcoma.

In embodiment 118, the invention provides the method of any one of embodiments 101-117 wherein the cancer is one or more of a solid tumor selected from cancer of the bladder, breast, colon, kidney, liver, lung, non-small cell lung, head and neck, esophageal, gastric, ovary, endometrium, pancreas, stomach, uterus, cervix, thyroid, brain and prostate or a lymphoma or leukemia, or a combination thereof.

In embodiment 119, the invention provides the method of any one of embodiments 101-117 wherein the cancer is a solid cancer tumor of the prostate, ovary, endometrium, breast, bladder, colon, kidney, liver, lung, esophagus, pancreas, stomach, uterus, cervix, thyroid, brain or skin, or a combination thereof.

In embodiment 120, the invention provides the method of any one of embodiments 101-119 wherein the dosage amount of AMG 900, or a pharmaceutically acceptable salt thereof, is in the range of about 1.5 mg to about 45 mg.

In embodiment 121, the invention provides the method of any one of embodiments 101-120 wherein the dosage amount of AMG 900 or a pharmaceutically acceptable salt thereof, is in the range of about 5 mg to about 45 mg.

In embodiment 122, the invention provides the method of any one of embodiments 101-121 wherein the dosage amount of AMG 900 or a pharmaceutically acceptable salt thereof, is in the range of about 10 mg to about 40 mg.

In embodiment 123, the invention provides the method of any one of embodiments 101-122 wherein the dosage amount of AMG 900 or a pharmaceutically acceptable salt thereof, is in the range of about 15 mg to about 40 mg.

In embodiment 124, the invention provides the method of any one of embodiments 101-123 wherein the dosage amount of AMG 900 or a pharmaceutically acceptable salt thereof, is in the range of about 16 mg to about 35 mg.

In embodiment 125, the invention provides the method of slowing the rate of growth of a solid tumor in a subject, the method comprising administering AMG 900, or a pharmaceutically acceptable salt thereof, to the subject in a dosage regimen comprising a dose of AMG 900 ranging from about 10 mg to about 45 mg.

In embodiment 126, the invention provides the method of any one of embodiments 101-124 wherein the dosage regimen comprises administering AMG 900, or a pharmaceutically acceptable salt thereof, in combination with a second anti-cancer agent.

In embodiment 127, the invention provides the method of embodiment 126 wherein the second anti-cancer agent is an HDAC inhibiting agent.

In embodiment 128, the invention provides the method of embodiment 127 wherein AMG 900 and the HDAC inhibiting agent are administered sequentially or co-administered simultaneously.

In embodiment 129, the invention provides the method of any one of embodiments 116-128 wherein the AMG 900, or a pharmaceutically acceptable salt thereof, and the HDAC inhibiting agent are co-administered in a single dosage formulation.

In embodiment 130, the invention provides the method of any one of embodiments 116-129 wherein the AMG 900, or a pharmaceutically acceptable salt thereof, and the HDAC inhibiting agent are co-administered as separate dosage formulations.

In embodiment 131, the invention provides the method of any one of embodiments 127-130 wherein the HDAC inhibiting agent is Vorinostat, Romidepsin, Panobinostat (LBH589), valproic acid, Belinostat (PXD101), Mocetinostat (MGCD103), Abexinostat (PCI-24781), Entinostat (MS-275), SB939, Resminostat (4SC-210), Givinostat (ITF2357), CUDC-101, AR-42, CHR-2845, CHR-3996, 4SC-202, CG200745, ACY-1215 or Sulforphane.

In embodiment 132, the invention provides the method of any one of embodiments 101-117 wherein the dosage regimen comprises administering AMG 900, or a pharmaceutically acceptable salt thereof, in combination with GCSF.

In embodiment 134, the invention provides the method of any one of embodiments 101-132 wherein the dosage regimen further comprises administering GCSF in an amount ranging from about 5 mcg/kg to about 200 mcg/kg by weight of the subject.

In embodiment 135, the invention provides the method of any one of embodiments 101-134 wherein the subject is a human.

In embodiment 136, the invention provides the method of embodiment 126 wherein the second anti-cancer agent is selected from methotrexate; tamoxifen; fluorouracil; 5-fluorouracil; hydroxyurea; mercaptopurine; cisplatin; carboplatin; daunorubicin; doxorubicin; etoposide; vinblastine; vincristine; paclitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a combination thereof.

Administering AMG 900 to a subject may be optimal if done so on an empty stomach. Thus, and as provided herein, embodiment 37 of the present invention further provides use of AMG 900 to treat cancer wherein the dosage regimen of any of embodiments 101-136 further comprises administering to the subject AMG 900, or a pharmaceutically acceptable salt thereof, to the subject at a time when the subject has not eaten food for a minimum of one hour immediately prior to administering the dose of AMG 900.

In embodiment 138, the dosage regimen of any one of embodiments 101-137 herein above may further comprise fasting the subject for at least one hour after administering the dose of AMG 900, or a pharmaceutically acceptable salt thereof, to the subject.

In embodiment 139, the dosage regimen of any one of embodiments 101-138 herein above may comprise fasting the subject for at least one hour immediately prior to and immediately after administering the dose of AMG 900, or a pharmaceutically acceptable salt thereof, to the subject.

In embodiment 140, the invention provides the method of any one of embodiments 101-115, wherein the dosage regimen comprises orally administering AMG 900 to the subject in a once daily dose ranging from about 20 mg to about 30 mg for 4 consecutive days followed immediately by non-treatment of AMG 900 for a period of 10 consecutive days.

In embodiment 141, the invention provides the method of any one of embodiments 101-115, wherein the dosage regimen comprises orally administering AMG 900 to the subject in a once daily dose ranging from about 20 mg to about 25 mg for 4 consecutive days followed immediately by non-treatment of AMG 900 for a period of 10 consecutive days.

In embodiment 142, the invention provides the method of any one of embodiments 101-115, wherein the dosage regimen comprises orally administering AMG 900 to the subject in a once daily dosage amount ranging from about 24 mg to about 25 mg for 4 consecutive days followed immediately by non-treatment of AMG 900 for a period of 10 consecutive days.

In embodiment 143, the invention provides the method of any one of embodiments 101-116 wherein the cancer is (a) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma or (b) a hematopoietic tumor of myeloid lineage selected from acute and chronic myelogenous leukemias, myelodysplastic syndrome and promyelocytic leukemia.

In embodiment 144, the invention provides the method of any one of embodiments 117-119, wherein the dosage regimen comprises orally administering AMG 900 to the subject in a once daily dose ranging from about 20 mg to about 30 mg for 4 consecutive days followed immediately by non-treatment of AMG 900 for a period of 10 consecutive days.

In embodiment 145, the invention provides the method of any one of embodiments 117-119, wherein the dosage regimen comprises orally administering AMG 900 to the subject in a once daily dose ranging from about 20 mg to about 25 mg for 4 consecutive days followed immediately by non-treatment of AMG 900 for a period of 10 consecutive days.

In embodiment 146, the invention provides the method of any one of embodiments 117-119, wherein the dosage regimen comprises orally administering AMG 900 to the subject in a once daily dosage amount ranging from about 24 mg to about 25 mg for 4 consecutive days followed immediately by non-treatment of AMG 900 for a period of 10 consecutive days.

In embodiment 147, the invention provides the method of any one of embodiments 117 and 143, wherein the dosage regimen comprises orally administering AMG 900 to the subject in a once daily dose ranging from about 10 mg to about 80 mg for 7 consecutive days followed immediately by non-treatment of AMG 900 for a period of 7 consecutive days.

In embodiment 148, the invention provides the method of any one of embodiments 117 and 143, wherein the dosage regimen comprises orally administering AMG 900 to the subject in a once daily dose ranging from about 20 mg to about 40 mg for 7 consecutive days followed immediately by non-treatment of AMG 900 for a period of 7 consecutive days.

In embodiment 149, the invention provides the method of any one of embodiments 117 and 143, wherein the dosage regimen comprises orally administering AMG 900 to the subject in a once daily dosage amount ranging from about 25 mg to about 35 mg for 7 consecutive days followed immediately by non-treatment of AMG 900 for a period of 7 consecutive days.

In embodiment 150, the invention provides use of AMG 900, or a pharmaceutically acceptable salt thereof, to treat cancer in a human, wherein AMG 900, or a pharmaceutically acceptable salt thereof, is administered to the human in a dosage regimen comprising a once daily dose ranging from about 5 mg to about 80 mg.

In embodiment 151, the invention provides use of embodiment 150, wherein AMG 900, or a pharmaceutically acceptable salt thereof, is administered in a once daily dose ranging from about 5 mg to about 45 mg.

In embodiment 152, the invention provides use of any one of embodiments 150-151, wherein AMG 900 is administered in a once daily dose ranging from about 10 mg to about 40 mg.

In embodiment 153, the invention provides use of any one of embodiments 150-152, wherein AMG 900, or a pharmaceutically acceptable salt thereof, is administered in a once daily dose ranging from about 16 mg to about 35 mg.

In embodiment 154, the invention provides use of any one of embodiments 150-153, wherein AMG 900, or a pharmaceutically acceptable salt thereof, is administered in a once daily dose ranging from about 20 mg to about 25 mg.

In embodiment 155, the invention provides use of any one of embodiments 150-154, wherein AMG 900, or a pharmaceutically acceptable salt thereof, is administered in a once daily dose of about 24 mg.

In embodiment 156, the invention provides use of embodiment 150, wherein AMG 900, or a pharmaceutically acceptable salt thereof, is administered in a once daily dose ranging from about 40 mg to about 80 mg.

In embodiment 157, the invention provides use of any one of embodiments 150-156, wherein the dosage regimen further comprises orally administering the dose of AMG 900, or a pharmaceutically acceptable salt thereof, to the human for 3, 4, 5, 6, 7, 8, 9 or 10 consecutive days.

In embodiment 158, the invention provides use of any one of embodiments 150-157, wherein AMG 900, or a pharmaceutically acceptable salt thereof, is orally administered to the human for 3, 4, 5, 6 or 7 consecutive days.

In embodiment 159, the invention provides use of any one of embodiments 150-158, wherein AMG 900, or a pharmaceutically acceptable salt thereof, is orally administered to the human for 4, 5, 6 or 7 consecutive days.

In embodiment 160, the invention provides use of any one of embodiments 150-159, wherein AMG 900, or a pharmaceutically acceptable salt thereof, is orally administered to the human for 4 consecutive days.

In embodiment 161, the invention provides use of any one of embodiments 50-159, wherein AMG 900, or a pharmaceutically acceptable salt thereof, is orally administered to the human for 7 consecutive days.

In embodiment 162, the invention provides use of any one of embodiments 157-161, wherein the dosage regimen further comprises non-treatment of AMG 900, or a pharmaceutically acceptable salt thereof, for a period ranging from 6 to 20 consecutive days immediately following the once daily consecutive day treatment with AMG 900.

In embodiment 163, the invention provides use of any one of embodiments 150-162, wherein AMG 900, or a pharmaceutically acceptable salt thereof, is orally administered to the human for 4, 5, 6 or 7 consecutive days followed immediately by non-treatment of AMG 900, or a pharmaceutically acceptable salt thereof, for a period ranging from 6 to 20 consecutive days.

In embodiment 164, the invention provides use of any one of embodiments 150-163, wherein AMG 900, or a pharmaceutically acceptable salt thereof, is orally administered to the human for 4 or 7 consecutive days followed immediately by non-treatment of AMG 900, or a pharmaceutically acceptable salt thereof, for a period ranging from 6 or 15 consecutive days.

In embodiment 165, the invention provides use of any one of embodiments 150-164, wherein the dosage regimen further comprises administering AMG 900, or a pharmaceutically acceptable salt thereof, in combination with GCSF.

In embodiment 166, the invention provides use of embodiment 165, wherein the GCSF is administered in an amount ranging from about 5 mcg/kg to about 200 mcg/kg by weight of the human.

In embodiment 167, the invention provides use of any one of embodiments 165-166, wherein AMG 900, or a pharmaceutically acceptable salt thereof, is administered in a once daily dose ranging from about 20 mg to about 40 mg in combination with GCSF administered in an amount ranging from about 5 mcg/kg to about 200 mcg/kg by weight of the human.

In embodiment 168, the invention provides use of any one of embodiments 165-167 wherein AMG 900, or a pharmaceutically acceptable salt thereof, is administered in a once daily dose ranging from about 30 mg to about 40 mg in combination with GCSF administered in an amount ranging from about 5 mcg/kg to about 200 mcg/kg by weight of the human.

In embodiment 169, the invention provides use of any one of embodiments 150-169, wherein the dosage regimen further comprises fasting the human for at least one hour immediately prior to administering AMG 900, or a pharmaceutically acceptable salt thereof, and for at least another 2 hours immediately after administering AMG 900, or a pharmaceutically acceptable salt thereof.

In embodiment 170, the invention provides a method of treating a cancer selected from the group consisting of ovarian cancer, breast cancer, non-small cell lung cancer and endometrial cancer, the method comprising administering to a subject in need of such treatment an effective dosage amount of crystalline form B bismesylate salt of AMG 900.

In embodiment 171, the invention provides a method of treating a cancer selected from the group consisting of ovarian cancer, breast cancer, non-small cell lung cancer and endometrial cancer, the method comprising instructing a subject in need of such treatment to administer an effective dosage amount of crystalline form B bismesylate salt of AMG 900.

In embodiment 172, the invention provides a method of treating a cancer selected from the group consisting of ovarian cancer, breast cancer, non-small cell lung cancer and endometrial cancer, the method comprising prescribing, instructing or directing a subject in need of such treatment, or selling to a subject in need of such treatment, to administer an effective dosage amount of crystalline form B bismesylate salt of AMG 900.

In embodiment 173, the invention provides a method of treating a cancer selected from the group consisting of ovarian cancer, breast cancer, non-small cell lung cancer and endometrial cancer, the method comprising substituting, for a subject in need of such treatment, a first pharmaceutical composition including an effective dosage amount of crystalline form B bismesylate salt of AMG 900 with a second pharmaceutical composition that is bioequivalent to the first pharmaceutical composition In embodiment 174, the invention provides use of crystalline form B bismesylate salt of AMG 900 for treating a cancer selected from the group consisting of ovarian cancer, breast cancer, non-small cell lung cancer and endometrial cancer.

In embodiment 175, the invention provides crystalline form B bismesylate salt of AMG 900 for use in treating a cancer selected from the group consisting of ovarian cancer, breast cancer, non-small cell lung cancer and endometrial cancer.

In embodiment 176, the invention provides methods and uses of any one of embodiments 170-174, wherein the cancer is ovarian cancer.

In embodiment 177, the invention provides methods and uses of any one of embodiments 170-174, wherein the cancer is breast cancer.

In embodiment 178, the invention provides methods and uses of any one of embodiments 170-174, wherein the cancer is non-small cell lung cancer.

In embodiment 179, the invention provides methods and uses of any one of embodiments 170-174, wherein the cancer is endometrial cancer.

In embodiment 180, the invention provides methods and uses of any one of embodiments 170-179, wherein the effective dosage amount of crystalline form B bismesylate salt of AMG 900 is a range from about 10 mg to about 40 mg.

In embodiment 181, the invention provides methods and uses of embodiments 170-179, wherein the effective dosage amount of crystalline form B bismesylate salt of AMG 900 is a range from about 16 mg to about 35 mg.

In embodiment 182, the invention provides methods and uses of embodiments 170-181, wherein the effective dosage amount of crystalline form B bismesylate salt of AMG 900 is a range from about 10 mg to about 40 mg.

In embodiment 183, the invention provides methods and uses of embodiments 170-182, wherein the methods and uses further comprise orally administering or instructing the oral administration of, the crystalline form B bismesylate salt of AMG 900 once daily for 4 consecutive days followed by non-administration for 10 consecutive days.

In embodiment 184, the invention provides methods and uses of embodiments 170-182, wherein the methods and uses further comprise orally administering or instructing the oral administration of, the crystalline form B bismesylate salt of AMG 900 once daily for 7 consecutive days followed by non-administration for 7 consecutive days.

In embodiment 185, the invention provides methods and uses of embodiments 170-184, wherein the methods and uses further comprise orally administering or instructing the oral administration of, the crystalline form B bismesylate salt of AMG 900 in combination with an a regulatory approved amount of a taxanes.

In embodiment 186, the invention provides the method of embodiment 185, wherein the taxanes is selected from the groups consisting of paclitaxel and docetaxel.

Besides being useful for human treatment, the compound is also useful for veterinary treatment of companion animals, exotic animals and farm animals, including mammals, rodents, and the like. For example, animals including horses, dogs, and cats may be similarly treated with AMG 900 for cancers refractory to standard-of-care cancer chemotherapy treatments.

FORMULATIONS

Crystalline salts of AMG 900 may be administered to the cancer subject as a pharmaceutical composition or medicament, comprising the compound (which is the active pharmaceutical ingredient or API of the invention), N-(4-((3-(2-amino-4-pyrimidinyl)-2-pyridinyl)oxy)phenyl)-4-(4-methyl-2-thienyl)-1-phthalazinamine, in association with one or more non-toxic, pharmaceutically-acceptable carriers, diluents and/or adjuvants (collectively referred to herein as "excipient" materials). The crystalline drug substance, that is a pharmaceutically acceptable salt of AMG 900, can be processed in accordance with conventional methods of pharmacy to produce the medicinal and pharmaceutical compositions for administration to patients, including humans and other mammals.

The pharmaceutical composition may be administered to the subject by any suitable route, adapted to such a route, and in a dose effective for the refractory cancer treatment intended. The composition, or API, may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of the API (AMG 900) which is administered and the dosage regimen for treating the refractory cancer condition depends on a variety of factors, including the age, weight, sex and medical condition of the subject, the type of disease, the severity of the cancer, the route and frequency of administration, and the physical and chemical properties of AMG 900 or its particular form, including the specific salt form. Thus, a dosage regimen may vary. A daily dose of about 0.01 to 500 mg/kg, advantageously between about 0.01 and about 50 mg/kg, more advantageously about 0.1 and about 30 mg/kg and even more advantageously between about 0.1 mg/kg and about 25 mg/kg body weight may be appropriate. In one embodiment, the invention provides a method of treating cancer in a subject, the method comprising administering to the subject AMG 900 or a pharmaceutically acceptable salt thereof in an effective dosage amount in the range from about 0.5 mg/kg to about 25 mg/kg, wherein the subject's cancer is refractory to treatment with an anti-mitotic agent. In another embodiment, the invention provides a method of treating cancer in a subject, the method comprising administering to the subject AMG 900 or a pharmaceutically acceptable salt thereof in an effective dosage amount in the range from about 1.0 mg/kg to about 20 mg/kg, wherein the subject's cancer is refractory to treatment with standard of care chemotherapeutic agent, including an anti-mitotic agent. In yet another embodiment, the invention provides a method of treating cancer in a subject, the method comprising administering to the subject AMG 900 or a pharmaceutically acceptable salt thereof in an effective dosage amount in the range from about 3.0 mg/kg to about 15 mg/kg, wherein the subject's cancer is refractory to treatment with an anti-mitotic agent. The daily dose can be administered in one to four doses per day.

For therapeutic purposes, AMG 900 may be combined with one or more adjuvants or "excipients" appropriate to the indicated route of administration. If administered on a per dose basis, AMG 900 may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, AMG 900 and the excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the API(s).

In the case of psoriasis and other skin conditions, it may be preferable to apply a topical preparation of the AMG 900 to the affected area two to four times a day. Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of the active ingredient is 0.1 mg to 150 mg administered one to four, preferably one or two times daily. For topical administration, the API may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, AMG 900 may be employed with either paraffinic or a water-miscible ointment base. Alternatively, it may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

AMG 900 can also be administered by transdermal device. Preferably transdermal administration will be accomplished using a patch either of the reservoir and porous membrane type or of a solid matrix variety. In either case, AMG 900 is delivered continuously from the reservoir or microcapsules through a membrane into the active agent permeable adhesive, which is in contact with the skin or mucosa of the recipient. If AMG 900 is absorbed through the skin, a controlled and predetermined flow of AMG 900 is administered to the recipient. In the case of microcapsules, the encapsulating agent may also function as the membrane.

The oily phase of the emulsions may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s)

make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the API in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for AMG 900. AMG 900 is preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. For example AMG 900 may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. AMG 900 may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectible solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

COMBINATIONS

While crystalline salts of AMG 900 (the invention) can be dosed or administered as the sole active pharmaceutical agent, it can also be used in combination with one or more chemotherapeutic and/or antimitotic agents. For instance, in one embodiment, the invention provides crystalline salts of AMG 900 administered in combination with a taxanes, such as paclitacel or docetaxcel. When administered as a combination, AMG 900 can be formulated as separate compositions that are administered simultaneously or sequentially at different times, or AMG 900 can be given as a single composition.

The phrase "co-therapy" (or "combination-therapy"), in defining the use of AMG 900 of the present invention and another chemotherapeutic agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of AMG 900 may be in conjunction with additional chemotherapeutic agent, including antimitotic therapies, known to those skilled in the art in the prevention or treatment of cancer. The invention is not limited in the sequence of administration, i.e, AMG 900 may be administered either prior to, simultaneous with or after administration of the known anticancer or anti-mitotic agent.

The foregoing is merely illustrative of the invention and is not intended to limit the invention to the disclosed uses. Variations and changes, which are routine to one skilled in the art, are intended to be within the scope and nature of the invention, which are defined in the appended claims. All mentioned references, patents, applications and publications, are hereby incorporated by reference in their entirety, as if here written.

What is claimed is:

1. A crystalline form A of a mesylate salt of AMG 900 having the formula

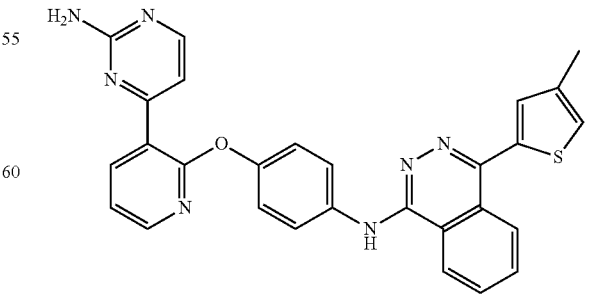

AMG 900 characterized by an X-ray powder diffraction (XRPD) diagram comprising peaks at the following angles of refraction 2theta: 9.89+/−0.16°, 12.96+/−0.10°, 16.52+/−0.10°, 17.84+/−0.16°, 20.05+/−0.10° and 21.55+/−0.19°.

2. A crystalline form A of a mesylate salt of the AMG 900 according to claim 1, characterized as providing an X-ray powder diffraction pattern substantially as shown in FIG. 1.

3. A crystalline form of a bismesylate salt of AMG 900 having the formula

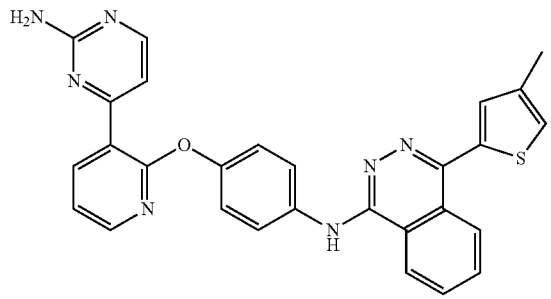

AMG 900 said form selected from Form A (dihydrate), Form B (dihydrate), Form C (monohydrate) or Form D (monohydrate).

4. A crystalline form A of a bismesylate dihydrate salt of AMG 900 according to claim 3, characterized by an X-ray powder diffraction (XRPD) diagram comprising peaks at the following angles of refraction 2theta: 5.60+/−0.10°, 8.07+/−0.10°, 11.17+/−0.13°, 16.76+/−0.13° and 17.52+/−0.13°.

5. A crystalline Form B of the bismesylate dihydrate salt of AMG 900 according to claim 3, characterized by an X-ray powder diffraction (XRPD) diagram comprising peaks at the following angles of refraction 2theta: 7.44+/−0.13°, 9.28+/−0.13°, 12.66+/−0.10°, 16.90+/−0.13° and 24.93+/−0.19°, and wherein the strongest peak in the X-ray diffraction diagram is observed at an angle of refraction 2theta of 24.93+/−0.19°.

6. A crystalline Form B of a bismesylate salt of the AMG 900 according to claim 5, characterized as providing an X-ray powder diffraction pattern substantially as shown in FIG. 3.

7. A crystalline form C of a bismesylate monohydrate salt of AMG 900 according to claim 3 characterized by an X-ray powder diffraction (XRPD) diagram comprising peaks at the following angles of refraction 2theta: 8.29+/−0.10°, 8.55+/−0.10°, 12.96+/−0.10° and 16.51+/−0.23°.

8. A crystalline form D of a bismesylate monohydrate salt of AMG 900 according to claim 3 characterized by an X-ray powder diffraction (XRPD) diagram comprising peaks at the following angles of refraction 2theta: 6.88+/−0.16°, 8.89+/−0.13°, 9.59+/−0.13°, 13.46+/−0.13° and 13.80+/−0.13°.

9. A pharmaceutical composition comprising a therapeutically effective dosage amount of a crystalline form of AMG 900 according to claim 1 and a pharmaceutically acceptable excipient, carrier or diluent.

10. A pharmaceutical composition comprising a therapeutically effective dosage amount of a crystalline form of AMG 900 according to claim 4 and a pharmaceutically acceptable excipient, carrier or diluent.

11. A pharmaceutical composition comprising a therapeutically effective dosage amount of a crystalline form of AMG 900 according to claim 5 and a pharmaceutically acceptable excipient, carrier or diluent.

12. A pharmaceutical composition comprising a therapeutically effective dosage amount of a crystalline form of AMG 900 according to claim 7 and a pharmaceutically acceptable excipient, carrier or diluent.

13. A pharmaceutical composition comprising a therapeutically effective dosage amount of a crystalline form of AMG 900 according to claim 8 and a pharmaceutically acceptable excipient, carrier or diluent.

* * * * *